(12) United States Patent
Hattori et al.

(10) Patent No.: US 7,417,060 B2
(45) Date of Patent: Aug. 26, 2008

(54) AMINOALCOHOL DERIVATIVES

(75) Inventors: Kouji Hattori, Osaka (JP); Susumu Toda, Osaka (JP); Masashi Imanishi, Osaka (JP); Shinji Ito, Osaka (JP); Kenichi Washizuka, Osaka (JP); Takanobu Araki, Osaka (JP); Minoru Sakurai, Osaka (JP); Daisuke Tanabe, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 526 days.

(21) Appl. No.: 11/016,886

(22) Filed: Dec. 21, 2004

(65) Prior Publication Data
US 2005/0137236 A1 Jun. 23, 2005

(30) Foreign Application Priority Data
Dec. 23, 2003 (AU) .............................. 2003907111

(51) Int. Cl.
A61K 31/44 (2006.01)
A61K 31/195 (2006.01)

(52) U.S. Cl. .................. 514/357; 514/567; 546/334; 562/433

(58) Field of Classification Search .................. 560/19, 560/20, 21; 564/161; 514/534, 553, 567, 514/617
See application file for complete search history.

(56) References Cited

U.S. PATENT DOCUMENTS

| | | | |
|---|---|---|---|
| 5,232,946 A * | 8/1993 | Hurnaus et al. .............. | 514/546 |
| 5,977,124 A | 11/1999 | Dow | |
| 7,037,938 B2 * | 5/2006 | Hattori et al. ............... | 514/534 |
| 2004/0006143 A1 | 1/2004 | Hattori et al. | |
| 2004/0106653 A1 | 6/2004 | Sakurai et al. | |
| 2005/0137236 A1 | 6/2005 | Hattori et al. | |

FOREIGN PATENT DOCUMENTS

| | | |
|---|---|---|
| EP | 0 543 662 | 5/1993 |
| WO | 90/06299 | 6/1990 |
| WO | 99/65877 | 12/1999 |
| WO | 02/32897 | 4/2002 |
| WO | 03/076397 | 9/2003 |
| WO | 2004/002939 | 1/2004 |
| WO | 2004/072016 | 8/2004 |

OTHER PUBLICATIONS

U.S. Appl. No. 11/304,632, filed Dec. 16, 2005, Hattori et al.
U.S. Appl. No. 11/547,847, filed Oct. 6, 2006, Hattori et al.

* cited by examiner

Primary Examiner—Zinna N Davis
(74) Attorney, Agent, or Firm—Oblon, Spivak, McClelland, Maier & Neustadt, P.C.

(57) ABSTRACT

The present invention relates to a compound formula[I]:

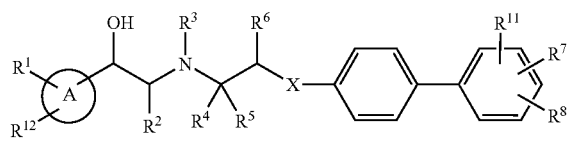

wherein

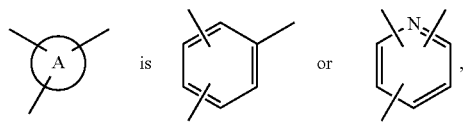

X is bond, —$CH_2$—, —O— or —NH—,
$R^1$ and $R^{12}$ are each independently hydrogen, halogen, lower alkyl, etc.,
$R^2$ is hydrogen or optionally substituted lower alkyl,
$R^3$ is hydrogen or an amino protective group,
$R^4$, $R^5$ and $R^6$ are each independently hydrogen or optionally substituted lower alkyl,
$R^7$ is -Z-$R^{13}$, in which
  Z is bond, etc., and
  $R^{13}$ is carboxy, lower alkoxycarbonyl, (lower alkylsulfonyl)carbamoyl or lower alkanoylsulfamoyl,
$R^8$ is —Y—$R^9$, in which
  Y is bond, —$CH_2$—, —O—, —S—, etc., and
  $R^9$ is hydrogen, lower alkyl, cyclo(lower)alkyl, etc., and
$R^{11}$ is hydrogen, lower alkyl, lower alkoxy, etc., or a salt thereof.

The compound [I] of the present invention and pharmaceutically acceptable salts thereof are useful for the prophylactic and/or therapeutic treatment of pollakiurea or urinary incontinence.

16 Claims, No Drawings

AMINOALCOHOL DERIVATIVES

CROSS REFERENCES TO RELATED APPLICATIONS

This application claims priority to Australian Patent Application No. 2003907111, filed on Dec. 23, 2003.

FIELD OF THE INVENTION

This invention relates to new aminoalcohol derivatives and salts thereof which are beta-3 ($\beta_3$) adrenergic receptor agonists and useful as a medicament.

BACKGROUND OF THE INVENTION

International Publication No. WO 90/06299, published Jun. 14, 1990, describes derivatives of phenylethanolamines as having an effect on the metabolism, preferably reduction of the blood sugar level and body fat, International Publication No. WO 02/32897, published Apr. 25, 2002, describes derivatives of alpha-aryl ethanolamines useful as $\beta_3$ adrenergic receptor agonists, and International Publication No. WO 2004/002939, published Jan. 8, 2004, describes aminoalcohol derivatives useful as $\beta_3$ adrenergic receptor agonists.

DISCLOSURE OF THE INVENTION

This invention relates to new aminoalcohol derivatives which are $\beta_3$ adrenergic receptor agonists and salts thereof.

More particularly, it relates to new aminoalcohol derivatives and salts thereof which are useful for the treatment and/or prevention of gastro-intestinal disorders, ulcer, overactive bladder, micturiation disorders, pancreatitis, obesity, diabetes, etc., to processes for the preparation thereof, to a pharmaceutical composition comprising the same and to a method of using the same therapeutically in the treatment and/or prevention of the aforesaid disorders in a human being or an animal.

One object of this invention is to provide new and useful aminoalcohol derivatives and salts thereof which are useful for the treatment and/or prevention of the aforesaid disorders.

Another object of this invention is to provide processes for the preparation of said aminoalcohol derivatives and salts thereof.

A further object of this invention is to provide a pharmaceutical composition comprising, as an active ingredient, said aminoalcohol derivatives and salts thereof.

Still further object of this invention is to provide a therapeutical method for the treatment and/or prevention of the aforesaid diseases in a human being or an animal, using said aminoalcohol derivatives and salts thereof.

The object aminoalcohol derivatives of this invention are new and can be represented by compound of the following formula [I]:

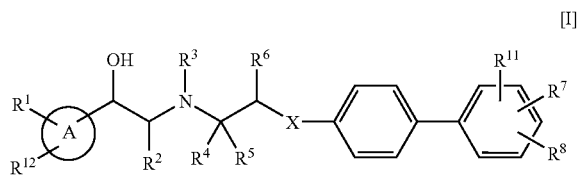

wherein

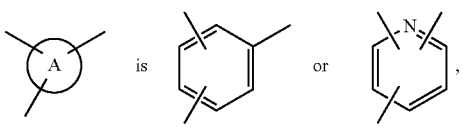

X is bond, —$CH_2$—, —O— or —NH—,
$R^1$ and $R^{12}$ are each independently hydrogen, halogen, lower alkyl, hydroxy, lower alkoxy, benzyloxy, nitro, amino or (lower alkylsulfonyl)amino,
$R^2$ is hydrogen or optionally substituted lower alkyl,
$R^3$ is hydrogen or an amino protective group,
$R^4$, $R^5$ and $R^6$ are each independently hydrogen or optionally substituted lower alkyl,
$R^7$ is -Z-$R^{13}$, in which
  Z is bond, —$(CH_2)_n$— (in which n is 1, 2, 3 or 4) or —$OCH_2$—, and
  $R^{13}$ is carboxy, lower alkoxycarbonyl, (lower alkylsulfonyl)carbamoyl or lower alkanoylsulfamoyl,
$R^8$ is —Y—$R^9$, in which
  Y is bond, —$CH_2$—, —O—, —S—, —SO—, —$SO_2$—, —NH— or

(in which $R^{10}$ is lower alkyl, cyclo(lower)alkyl or aryl), and
  $R^9$ is hydrogen, lower alkyl, cyclo(lower)alkyl, mono(or di or tri)halo(lower)alkyl, lower alkanoyl, lower alkenyl, lower alkoxy(lower)alkyl, nitro, aryl or a heterocyclic group, and
$R^{11}$ is hydrogen, lower alkyl, lower alkoxy, amino or mono(or di)lower(alkyl)amino, provided that when $R^7$ is carboxy or lower alkoxycarbonyl, then
(i) $R^2$ is lower alkyl,
(ii) $R^4$ is substituted lower alkyl,
(iii) $R^6$ is optionally substituted lower alkyl, or
(iv) $R^1$ and $R^{12}$ are each hydrogen, $R^2$ is hydrogen,
  $R^4$, $R^5$ and $R^6$ are each hydrogen, and
  $R^8$ is cyclo(lower)alkyl, methylthio, ethylthio, methylsulfonyl, ethylsulfonyl, lower alkoxy(lower)alkylthio, amino, mono(or di)(lower)alkylamino, lower alkanoylamino, cyclo(lower)alkylamino, mono(or di or tri)halo(lower)alkyl, lower alkenyl, lower alkoxy(lower)alkyl, tetrahydropyranyloxy, thienyl, pyridyl or pyridyloxy, or a salt thereof.

According to this invention, the object compounds can be prepared by processes which are illustrated in the following schemes.

Process 1

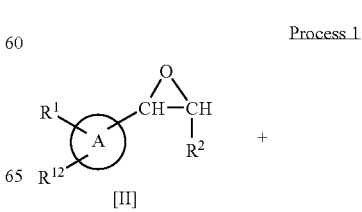

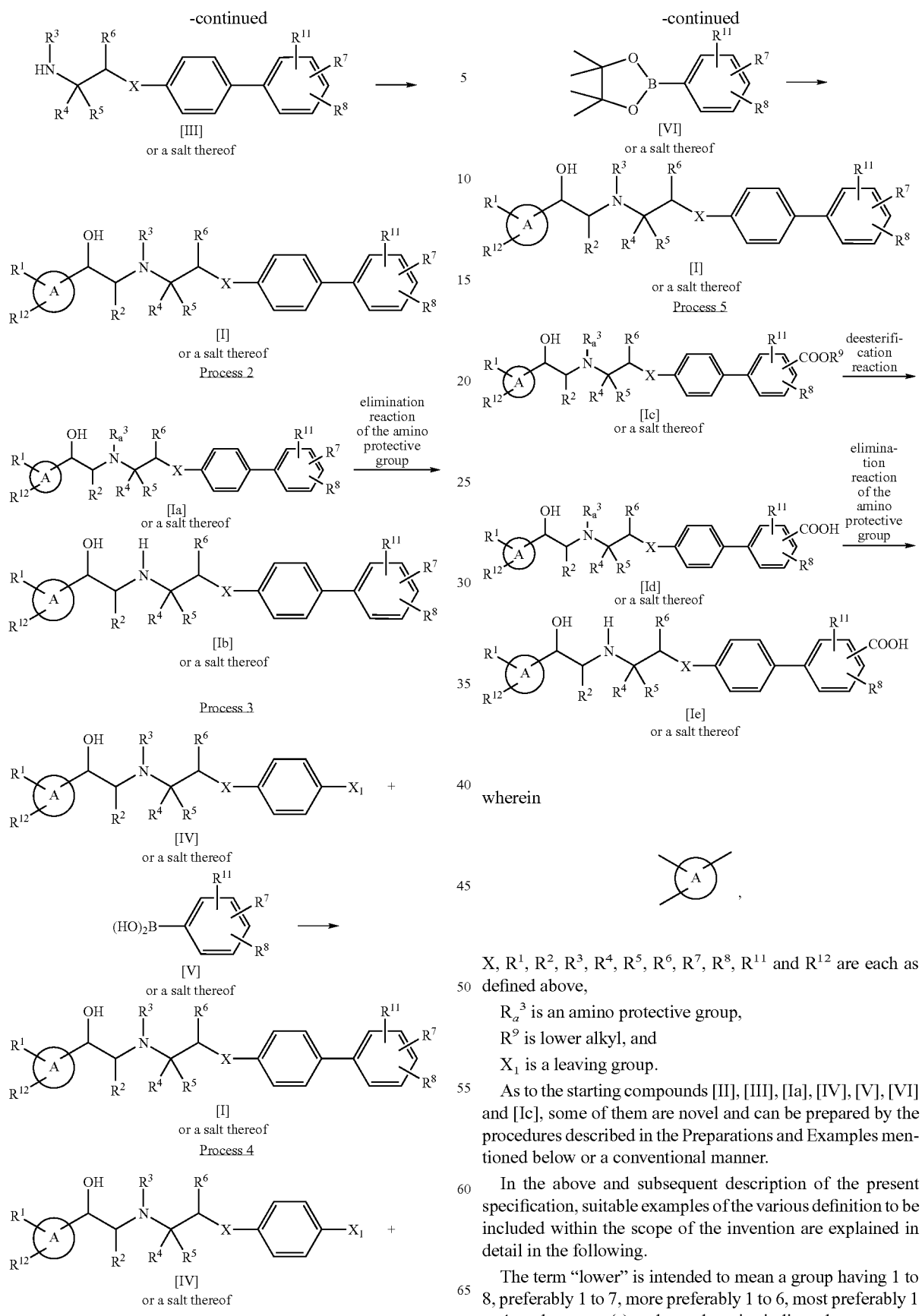

wherein

X, $R^1$, $R^2$, $R^3$, $R^4$, $R^5$, $R^6$, $R^7$, $R^8$, $R^{11}$ and $R^{12}$ are each as defined above, $R_a^3$ is an amino protective group, $R^9$ is lower alkyl, and $X_1$ is a leaving group.

As to the starting compounds [II], [III], [Ia], [IV], [V], [VI] and [Ic], some of them are novel and can be prepared by the procedures described in the Preparations and Examples mentioned below or a conventional manner.

In the above and subsequent description of the present specification, suitable examples of the various definition to be included within the scope of the invention are explained in detail in the following.

The term "lower" is intended to mean a group having 1 to 8, preferably 1 to 7, more preferably 1 to 6, most preferably 1 to 4, carbon atom(s), unless otherwise indicated.

Suitable "lower alkyl" and "lower alkyl" moiety in the terms of "(lower alkylsulfonyl)carbamoyl", "mono(or di)lower(alkyl)amino", "(lower alkylsulfonyl)amino", etc. may include straight or branched one having 1 to 8, preferably 1 to 7, more preferably 1 to 6 carbon atom(s), such as methyl, ethyl, propyl, isopropyl, butyl, isobutyl, sec-butyl, tert-butyl, pentyl, 1-methylpentyl, tert-pentyl, neo-pentyl, hexyl, isohexyl, heptyl, isoheptyl, octyl, isooctyl and the like.

Suitable "lower alkoxy" moiety in the terms of "lower alkoxycarbonyl", "lower alkoxy(lower)alkyl", etc. may include methoxy, ethoxy, propoxy, isopropoxy, butoxy, isobutoxy, tert-butoxy, pentyloxy, tert-pentyloxy, hexyloxy and the like, in which preferable one is methoxy or ethoxy.

Suitable "lower alkanoyl" moiety in the term of "lower alkanoylsulfamoyl" may include formyl, acetyl, propanoyl, butanoyl, 2-methylpropanoyl, pentanoyl, 2,2-dimethylpropanoyl, hexanoyl and the like.

Suitable "cyclo(lower)alkyl" may include cyclopropyl, cyclobutyl, cyclopentyl, cyclohexyl, cycloheptyl, cyclooctyl and the like, in which preferable one is cyclo($C_3$-$C_7$)alkyl, and most preferable one is cyclopentyl or cyclohexyl.

Suitable "mono(or di or tri)halo(lower)alkyl" may include chloromethyl, dichloromethyl, trichloromethyl, bromomethyl, dibromomethyl, tribromomethyl, fluoromethyl, difluoromethyl, trifluoromethyl, 1 or 2-chloroethyl, 1 or 2-bromoethyl, 1 or 2-fluoroethyl, 1,1-difluoroethyl, 2,2-difluoroethyl, 2,2,2-trifluoroethyl, 3-fluoropropyl and the like.

Suitable "lower alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, 1-(or 2-)methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl and the like, in which more preferable example may be $C_2$-$C_4$ alkenyl.

Suitable "halogen" may be fluoro, chloro, bromo and iodo, in which preferable one is chloro.

Suitable "aryl" may include phenyl, naphthyl, indenyl, anthryl and the like, in which preferable one is $C_6$-$C_{10}$ aryl, and more preferable one is phenyl.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;

saturated 3 to 7-membered heteromonocyclic group containing 1 to 4 nitrogen atoms [e.g. pyrrolidinyl, imidazolidinyl, piperidyl, piperazinyl, homopiperazinyl, etc.];

unsaturated condensed heterocyclic group containing 1 to 5 nitrogen atoms, for example, indolyl, isoindolyl, indolizinyl, benzimidazolyl, quinolyl, isoquinolyl, imidazopyridyl, indazolyl, benzotriazolyl, tetrazolopyridazinyl [e.g. tetrazolo[1,5-b]pyridazinyl, etc.], quioxalinyl, etc.;

unsaturated 3 to 6-membered heteromonocyclic group containing an oxygen atom, for example, pyranyl, furyl, etc.;

saturated 3 to 6-membered heteromonocyclic group containing an oxygen atom, for example, 1H-tetrahydropyranyl, tetrahydrofuranyl, etc.;

unsaturated 3 to 6-membered heteromonocyclic group containing 1 to 2 sulfur atoms, for example, thienyl, etc.;

unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], oxazolinyl [e.g. 2-oxazolinyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzofurazanyl, benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g. 1,2,4-thiadiazolyl, 1,3,4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g. thiazolidinyl, etc.];

unsaturated condensed heterocyclic group containing 1 to 2 sulfur atoms and 1 to 3 nitrogen atoms [e.g. benzothiazolyl, benzothiadiazolyl, etc.];

unsaturated condensed heterocyclic group containing 1 to 2 oxygen atoms [e.g. benzofuranyl, benzodioxolyl, chromanyl, etc.] and the like, in which preferable one is thienyl.

The term "optionally substituted" refers to "unsubstituted or substituted by one or more suitable substituent(s)".

Suitable "optionally substituted lower alkyl" may include lower alkyl which is optionally substituted by suitable substituent(s) such as lower alkoxy, hydroxy, cyclo(lower)alkyl and the like, in which preferable one is hydroxymethyl.

Suitable "leaving group" may include hydroxy, reactive group derived from hydroxy and the like.

Suitable "reactive group derived from hydroxy" may include acid residue and the like.

Suitable "acid residue" may include halogen (e.g. fluoro, chloro, bromo, iodo), acyloxy (e.g. acetoxy, tosyloxy, mesyloxy, trifluoromethanesulfonyloxy, etc.) and the like.

Suitable example of "amino protective group" moiety may be common amino protective group such as substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, ar(lower)alkyl [e.g. trityl, benzyl, etc.], and the like, in which preferable one is tert-butoxycarbonyl.

Suitable salts of the object aminoalcohol derivative [I] are pharmaceutically acceptable salts and include conventional non-toxic salts such as an inorganic acid addition salt [e.g. hydrochloride, hydrobromide, sulfate, phosphate, etc.], an organic acid addition salt [e.g. formate, acetate, trifluoroacetate, oxalate, maleate, fumarate, tartrate, citrate, methanesulfonate, benzenesulfonate, toluenesulfonate, etc., an alkali metal salt [e.g. sodium salt, potassium salt, etc.] or the like.

The Processes 1 to 5 for preparing the object compounds of the present invention are explained in detail in the following.

Process 1

The object compound [I] or a salt thereof can be prepared by reacting a compound [II] with a compound [III] or a salt thereof.

Suitable salt of the compound [III] may be the same as those exemplified for the compound [I].

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower)alkylamine [e.g. trimethylamine, triethylamine, etc.], picoline or the like.

The reaction is usually carried out in a conventional solvent, such as an alcohol [e.g. methanol, ethanol, propanol, isopropanol, etc.], diethyl ether, tetrahydrofuran, dioxane, or any other organic solvent which does not adversely influence the reaction.

The reaction temperature is not critical, and the reaction can be carried out under cooling to heating.

Process 2

The object compound [Ib] or a salt thereof can be prepared by subjecting a compound [Ia] or a salt thereof to elimination reaction of the amino protective group.

Suitable salts of the compounds [Ia] and [Ib] may be the same as those exemplified for the compound [I].

This reaction can be carried out in a similar manner to that of Example 6 mentioned below.

Process 3

The object compound [I] or a salt thereof can be prepared by reacting a compound [IV] or a salt thereof with a compound [V] or a salt thereof.

Suitable salts of the compounds [I], [IV] and [V] may be the same as those exemplified for the compound [I].

This reaction can be carried out in a similar manner to that of Preparation 14 mentioned below.

Process 4

The object compound [I] or a salt thereof can be prepared by reacting a compound [IV] or a salt thereof with a compound [VI] or a salt thereof.

Suitable salts of the compounds [I], [IV] and [VI] may be the same as those exemplified for the compound [I].

This reaction can be carried out in a similar manner to that of Example 1 mentioned below.

Process 5

The object compound [Ie] or a salt thereof can be prepared by subjecting a compound [Ic] or a salt thereof to deesterification reaction followed by subjecting a compound [Id] or a salt thereof to elimination reaction of the amino protective group.

Suitable salts of the compound [Ie], [Ic] and [Id] may be the same as those exemplified for the compound [I].

These reactions can be carried out in a similar manner to that of Example 4 mentioned below.

The compounds obtained by the above processes can be isolated and purified by a conventional method such as pulverization, recrystallization, column chromatography, reprecipitation, or the like, and converted to the desired salt in conventional manners, if necessary.

It is to be noted that the compound [I] and the other compounds may include one or more stereoisomers due to asymmetric carbon atoms, and all of such isomers and mixture thereof are included within the scope of this invention.

It is further to be noted that isomerization or rearrangement of the object compound [I] may occur due to the effect of the light, acid base or the like, and the compound obtained as the result of said isomerization or rearrangement if also included within the scope of the present invention.

It is also to be noted that the solvating form of the compound [I] (e.g. hydrate, etc.) and any form of the crystal of the compound [I] are included within the scope of the present invention.

The object compound [I] or a salt thereof are useful for the treatment and/or prevention of gastro-intestinal disorders in human beings or animals, and more particularly for the treatment and/or prevention of spasm or hyperanakinesia in case of irritable bowel syndrome, gastritis, gastric ulcer, duodenal ulcer, enteritis, cholecystopathy, cholantitis, urinary calculus and the like; for the treatment and/or prevention of ulcer such as gastric ulcer, duodenal ulcer, peptic ulcer, or the like; for the treatment and/or prevention of overactive bladder such as nervous pollakiuria, neurogenic bladder dysfunction, nocturia, unstable bladder, cystospasm, chronic cystitis, chronic prostatitis, prostatic hypertrophy or the like; for the treatment and/or prevention of micturiation disorder such as stress incontinence, urge incontinence, mixed incontinence, functional incontinence, overflow incontinence; for the treatment and/or prevention of pancreatitis, obesity, diabetes, glycosuria, hyperlipidemia, hypertension, atherosclerosis, glaucoma, melancholia, depression or the like; for the treatment and/or prevention of diseases as the result of insulin resistance (e.g. hypertension, hyperinsulinemia, etc.); for the treatment and/or prevention of neurogenetic inflammation; and for reducing a wasting condition, and the like.

Additionally, $\beta_3$ adrenergic receptor agonists are known to lower triglyceride and cholesterol levels and to raise high density lipoprotein levels in mammals (U.S. Pat. No. 5,451, 677). Accordingly, the object compound [I] is useful in the treatment and/or prevention of conditions such as hyper-triglyceridaemia, hypercholesterolaemia and in lowering high density lipoprotein levels as well as in the treatment of atherosclerotic and cardiovascular diseases and relates conditions.

Moreover, the object compound [I] is useful for inhibiting uterine contractions, preventing premature labor, and treating and preventing dysmenorrhea.

For therapeutic purpose, the compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral, external including topical, internal, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eye drops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg and 1000 mg of the compound (I) may be effective for treating diseases such as pollakiurea, urinary incontinence and the like. In general, amounts between 0.1 mg/body and about 1,000 mg/body may be administered per day.

In order to show the usefulness of the compound [I] for the prophylactic and therapeutic treatment of above-mentioned disease in human being or animals, a representative compound of the compound [I] was tested on the following pharmaceutical test.

Test

Effect on the Increase in Intravesical Pressure Induced by Carbachol in Anesthetized Dog Test Compound
(1) 4'-[2-[[(1S,2R)-2-Hydroxy-1-methyl-2-phenylethyl]-amino]ethyl]-3-(isopropylthio)-4-biphenylcarboxylic acid hydrochloride
(2) 4'-[2-[[(1S,2R)-2-Hydroxy-1-methyl-2-phenylethyl]-amino]ethyl]-3-isobutyl-N-(methylsulfonyl)-4-biphenylcarboxamide hydrochloride
(3) 3-(Cyclohexyloxy)-4'-[2-[[(2R)-2-hydroxy-2-(3-pyridyl)ethyl]amino]ethyl]-N-(methylsulfonyl)-4-biphenylcarboxamide dihydrochloride Test Method Female Beagle dogs weighing 8.0-15.0 kg were fasted for 24 hours and maintained under halothane anesthesia. A 12F Foley catheter was lubricated with water soluble jelly, inserted into the urethral orifice and advanced approximately 10 cm until the balloon tip was placed well inside the bladder. The balloon was then inflated with 5 ml of room air and catheter slowly withdrawn just part the first resistance that was felt at the bladder neck. Urine was completely drained out through the catheter, and 30 ml of biological saline was infused. The catheter was connected to pressure transducer, and intravesical pressure (IVP) was continuously recorded. The test compound was administered intravenously at 30 minutes before the administration of carbachol (1.8 μg/kg). Percent inhibition of IVP increase by test compound was calculated by dividing IVPa (IVP increase induced by carbachol after test compound administration) by IVPb (IVP increase induced by carbachol just before test compound administration).

Test Results

| Treatment | Percent inhibition of IVP increase |
| --- | --- |
| Test Compound (1) (0.010 mg/kg) | 77 |
| Test Compound (2) (0.010 mg/kg) | 76 |
| Test Compound (3) (0.010 mg/kg) | 89 |

Preferred embodiments of the object compound [I] are as follows:
$R^7$ is -Z-$R^{13}$, in which
　Z is bond or —$(CH_2)_n$— (in which n is 1), and
　$R^{13}$ is carboxy or lower alkoxycarbonyl (more preferably $C_1$-$C_4$ alkoxycarbonyl, most preferably methoxycarbonyl or ethoxycarbonyl).

More preferred embodiments of the object compound [I] are as follows:
X is bond,
$R^1$ and $R^{12}$ are each independently hydrogen or halogen,
$R^3$ is hydrogen,
$R^4$ is hydrogen,
$R^5$ is optionally substituted lower alkyl (more preferably $C_1$-$C_4$ alkyl, most preferably methyl),
$R^8$ is —Y—$R^9$, in which
　Y is bond, —$CH_2$—, —O— or —S—, and
　$R^9$ is lower alkyl (more preferably $C_1$-$C_4$ alkyl, most preferably propyl or isopropyl), cyclo(lower)alkyl (more preferably cyclo($C_3$-$C_6$)alkyl, most preferably cyclohexyl) or lower alkoxy(lower)alkyl (more preferably $C_1$-$C_4$ alkoxy($C_1$-$C_4$)alkyl, most preferably 2-ethoxyethyl), and
$R^{11}$ is hydrogen.

Other preferred embodiments of the object compound [I] are as follows:
$R^7$ is -Z-$R^{13}$, in which
　Z is bond or —$(CH_2)_n$— (in which n is 1), and
　$R^{13}$ is (lower alkylsulfonyl)carbamoyl (more preferably ($C_1$-$C_4$ alkylsulfonyl)carbamoyl, most preferably (methylsulfonyl)carbamoyl or (ethylsulfonyl)-carbamoyl) or lower alkanoylsulfamoyl (more preferably $C_1$-$C_4$ alkanoylsulfamoyl, most preferably acetylsulfamoyl).

More preferred embodiments of the compound [I] are as follows:
X is bond,
$R^1$ and $R^{12}$ are each independently hydrogen or halogen,
$R^3$ is hydrogen,
$R^4$ is hydrogen,
$R^8$ is —Y—$R^9$, in which
　Y is bond, —$CH_2$—, —O—, —S— or —NH—, and
　$R^9$ is lower alkyl (more preferably $C_1$-$C_4$ alkyl; most preferably isopropyl, isobutyl or isopentyl) or cyclo(lower)alkyl (more preferably cyclo($C_3$-$C_6$)alkyl, most preferably cyclopentyl or cyclohexyl), and
$R^{11}$ is hydrogen.

The following Preparations and Examples are given for the purpose of illustrating this invention. The group of "carbamoyl" aforementioned may be hereinafter referred as a group of "aminocarbonyl".

Preparation 1

To a mixture of (4-bromophenyl)acetic acid (10 g), and (1R,2S)-norephedrine (5.8 g) and 1-hydroxybenzotriazole (6.2 g) in N,N-dimethylformamide (100 ml) was added 1-(3-dimethylaminopropyl)-3-ethylcarbodiimide (8.8 g), and the mixture was stirred at room temperature for 2 hours. The mixture was partitioned between ethyl acetate and water. The organic layer was separated, washed successively with sodium bicarbonate solution and brine, dried over magnesium sulfate and evaporated under reduced pressure to give an amide product. To a tetrahydrofuran (100 ml) solution of the product, 2M-boran-dimethylsulfide complex in tetrahydrofuran (100 ml) was added at room temperature, and the mixture was refluxed for 30 minutes. To the mixture, 12N-hydrochloride acid (50 ml) was added dropwise below 10° C., and the mixture was stirred at room temperature for 3 hours. To the reaction mixture, 3N aqueous sodium hydroxide solution below 10° C. was added and di-tert-butyl dicarbonate (10 g) was added portionally at room temperature. The pH value was kept between 7 to 8 by using 1N aqueous sodium hydroxide solution. The mixture was stirred at room temperature for 1 hour. The mixture was partitioned between ethyl acetate and water. The organic layer was separated, washed brine, dried over magnesium sulfate and evaporated under reduced pressure. The residue was purified by column chromatography on silica gel (hexane/ethyl acetate=2/1) to give 4-[2-[[(1S,2R)-2-hydroxy-2-phenyl-1-methylethyl](tert-butyloxycarbonyl) amino]ethyl]phenyl bromide (16 g).

MS (m/z): 434 (M+H)

Preparation 2

A solution of (1S)-1-hydroxymethyl-2-(4-iodophenyl)-ethylamine (5 g), and (R)-styrene oxide (2 g) in ethanol (50 ml) was refluxed for 18 hours. The mixture was evaporated in vacuo. The residual oil was diluted in tetrahydrofuran (50 ml). To the solution was added di-tert-butyl dicarbonate (5 g) at room temperature, and the mixture was stirred at the same temperature for 12 hours. The resulting mixture was evaporated under pressure and the residue was purified by column chromatography on silica gel to give 4-[(2R)-2-[[(2S)-2-hydroxy-2-phenylethyl](tert-butyloxycarbonyl)amino]-2-(hydroxymethyl)ethyl]phenyl iodide (5.5 g).

MS (m/z): 498 (M+H)

Preparation 3

To a mixture of magnesium (1.61 g) in tetrahydrofuran (10 ml) was added a solution of isoamyl bromide (5.0 g) in tetrahydrofuran (23 ml) dropwise at room temperature under nitrogen, and the mixture was refluxed for 0.5 hour and cooled to room temperature. The mixture was transferred via a syringe to a solution of 4-bromo-2-fluorobenzoic acid (2.5 g) in tetrahydrofuran (15 ml) at 4-10° C. The resulting mixture was stirred at room temperature for 16 hours. To the reaction mixture was added water (200 ml) dropwise with ice-cooling. The aqueous solution was acidified with 6N aqueous hydrochloride solution and extracted with ethyl acetate (150 ml×2). The combined organic layers were washed with brine, dried over magnesium sulfate and evaporated under reduced pressure. The residue was purified by column chromatography on silica gel (chloroform/methanol=10/1) to give 4-bromo-2-(3-methylbutyl)benzoic acid (1.35 g).

MS (m/z): 269, 271 (M–H)⁻

Preparation 4

To a suspension of 4-bromo-2-(3-methylbutyl)benzoic acid (1.3 g) and methanesulfonamide (365 mg) in N,N-dimethylformamide (12 ml) was added 1-ethyl-3-(3-dimethylaminopropyl)carbodiimide hydrochloride (735 mg) and 4-dimethylaminopyridine (469 mg), and stirred at 30° C. for 16 hours. The mixture was diluted with ethyl acetate, washed with 1N aqueous hydrochloride solution, water and brine, dried over magnesium sulfate and evaporated under reduced pressure. The residue was purified by column chromatography on silica gel (hexane/ethyl acetate=2/1) to give 4-bromo-2-(3-methylbutyl)-N-(methylsulfonyl)benzamide (1.25 g).

MS (m/z): 346, 348 (M–H)⁻

Preparation 5

The following compound was obtained according to a similar manner to that of Preparation 4.

4-Bromo-2-isobutyl-N-(methylsulfonyl)benzamide

MS (m/z): 332, 334 (M–H)⁻

Preparation 6

To a solution of 4-bromo-2-(3-methylbutyl)-N-(methylsulfonyl)benzamide (1.22 g) in 1,4-dioxane (22 ml) was added bis(pinacolate)diboron (890 mg), dichlorobis-(triphenylphosphine)palladium(II) (172 mg) and potassium acetate (1.38 g), and the mixture was stirred at 90° C. for 2 hours under nitrogen. The mixture was diluted with ethyl acetate, washed with 1N aqueous hydrochloride solution, water and brine, dried over magnesium sulfate and evaporated under reduced pressure to give 2-(3-methylbutyl)-N-(methylsulfonyl)-4-(4,4,5,5-tetramethyl-1,3,2-dioxaborolan-2-yl)benzamide (1.75 g) which was used without any further purifications.

MS (m/z): 394 (M–H)⁻

Preparation 7

The following compound was obtained according to a similar manner to that of Preparation 6.

2-Isobutyl-N-(methylsulfonyl)-4-(4,4,5,5-tetramethyl-1,3,2-dioxaborolan-2-yl)benzamide MS (m/z): 380 (M–H)⁻

Preparation 8

To a solution of 4-bromo-2-fluorobenzoic acid (1 g) in pyridine (5 ml) was added isopropylamine (1.94 ml) at room temperature and the mixture was stirred at 100° C. overnight. The mixture was poured into aqueous hydrochloric acid (1N) and extracted with ethyl acetate. The organic layer was washed with brine, dried over magnesium sulfate and evaporated. The residue was purified by column chromatography on silica gel (hexane/ethyl acetate=2/1) to give 4-bromo-2-(isopropylamino)benzoic acid (218 mg).

(–)ESI-MS (m/z): 256 (M–H)⁻

Preparation 9

To a suspension of 4-bromo-2-(isopropylamino)benzoic acid (448 mg) and potassium carbonate (480 mg) in N,N-dimethylformamide (9 ml) was added methyl iodide (162 μl) at room temperature and the mixture was stirred at the same temperature for 1 hour. To the mixture was added water (20 ml) and extracted with mixed solvent (hexane/ethyl acetate=1/1). The organic layer was washed with brine, dried over magnesium sulfate and evaporated to give methyl 4-bromo-2-(isopropylamino)benzoate (443 mg).

NMR (CHCl₃, δ): 1.27 (6H, d, J=6.2 Hz), 3.62-3.71 (1H, m), 3.84 (3H, s), 6.64 (1H, dd, J=8.5, 1.9 Hz), 6.83 (1H, d, J=1.8 Hz), 7.70-7.75 (2H, m)

Preparation 10

To a solution of methyl 4-bromo-2-(isopropylamino)benzoate (433 mg) in 1,2-dimethoxyethane (6.5 ml) were added [4-[2-[benzyl(tert-butoxycarbonyl)amino]ethyl]phenyl]boronic acid (848 mg), tetrakis(triphenylphosphine)palladium (184 mg) and aqueous solution of sodium carbonate (2M, 3.5 ml), and the mixture was stirred at 70° C. for 2 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=17/3) to give methyl 4'-[2-[benzyl(tert-butoxycarbonyl)amino]ethyl]-3-(isopropylamino)-4-biphenylcarboxylate (768 mg).

(+)ESI-MS (m/z): 503 (M+H)⁺

Preparation 11

To a solution of methyl 4'-[2-[benzyl(tert-butoxycarbonyl)amino)ethyl]-3-(isopropylamino)-4-biphenylcarboxylate (768 mg) in tetrahydrofuran (8 ml) was added 4N hydrogen chloride solution in 1,4-dioxane (8 ml) at 0° C., and the mixture was stirred at room temperature overnight. The mixture was evaporated under reduced pressure and the residue was diluted with chloroform and water. The mixture was basified with aqueous solution of sodium hydroxide (1N) and the organic layer was separated, dried over magnesium sulfate and evaporated under reduced pressure to give methyl 4'-[2-(benzylamino)ethyl]-3-(isopropylamino)-4-biphenylcarboxylate (600 mg).

(+)ESI-MS (m/z): 403 (M+H)⁺

Preparation 12

To a solution of tert-butyl [2-(4-bromophenyl)ethyl]-[(2R)-2-hydroxy-2-phenylethyl]carbamate (3.20 g) in dichloromethane (40 ml) were added 3,4-dihydro-2H-pyran (1.28 g) and pyridinium p-toluenesulfonate (191 mg) at room temperature and the mixture was stirred at the same temperature for 5 hours under nitrogen. The mixture was diluted with ethyl acetate and water. The organic layer was separated, washed with brine, dried over sodium sulfate and evaporated under reduced pressure to give tert-butyl [2-(4-bromophenyl)ethyl][(2R)-2-phenyl-2-(tetrahydro-2H-pyran-2-yloxy)ethyl]carbamate (4.11 g).

(+)ESI-MS (m/z): 526 (M+Na)+

Preparation 13

The following compound was obtained according to a similar manner to that of Example 3.

tert-Butyl [2-[4-(2,2-dimethyl-4-oxo-4H-1,3-benzo-dioxin-7-yl)phenyl]ethyl][(2R)-2-phenyl-2-(tetrahydro-2H-pyran-2-yloxy)ethyl]carbamate (+)ESI-MS (m/z): 624 (M+Na)+

Preparation 14

To a solution of tert-butyl [2-(4-bromophenyl)ethyl]-[(2R)-2-phenyl-2-(tetrahydro-2H-pyran-2-yloxy)ethyl]-carbamate (620 mg) in 1,2-dimethoxyethane (7 ml) were added [3-(cyclohexyloxy)-4-(methoxycarbonyl)phenyl]boronic acid (410 mg), tetrakis(triphenylphosphine)palladium (99 mg) and aqueous solution of sodium carbonate (2M, 1.35 ml), and the mixture was stirred at 75° C. for 5 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=9/1) to give methyl 4'-[2-[(tert-butoxycarbonyl)[(2R)-2-phenyl-2-(tetrahydro-2H-pyran-2-yloxy)ethyl]amino]ethyl]-3-(cyclohexyloxy)-4-biphenylcarboxylate (672 mg).

(+)ESI-MS (m/z): 680 (M+Na)+

Preparation 15

The following compound was obtained according to a similar manner to that of Example 10.

4'-[2-[(tert-Butoxycarbonyl)[(2R)-2-phenyl-2-(tetrahydro-2H-pyran-2-yloxy)ethyl]amino]ethyl]-3-(cyclohexyloxy)-4-biphenylcarboxylic acid (−)ESI-MS (m/z)-642 (M−H)−

Preparation 16

To a solution of tert-butyl [2-[4-(2,2-dimethyl-4-oxo-4H-1,3-benzodioxin-7-yl)phenyl]ethyl][(2R)-2-phenyl-2-(tetrahydro-2H-pyran-2-yloxy)ethyl]carbamate (1.32 g) in methanol (15 ml) was added potassium carbonate (455 mg) at room temperature and the mixture was stirred at room temperature for 15 hours. The mixture was evaporated under reduced pressure. The residue was dissolved in ethyl acetate, and washed with water, brine and aqueous hydrochloric acid solution (0.1N). The organic layer was dried over sodium sulfate and evaporated under reduced pressure to give methyl 4'-[2-[(tert-butoxycarbonyl)[(2R)-2-phenyl-2-(tetrahydro-2H-pyran-2-yloxy)ethyl]amino]ethyl]-3-hydroxy-4-biphenylcarboxylate (1.11 g).

(+)ESI-MS (m/z): 598 (M+Na)+

Preparation 17

To a solution of methyl 4'-[2-[(tert-butoxycarbonyl)[(2R)-2-phenyl-2-(tetrahydro-2H-pyran-2-yloxy)ethyl]amino]ethyl]-3-hydroxy-4-biphenylcarboxylate (175 mg) in tetrahydrofuran (2 ml) were added 2-methyl-1-propanol (33.8 mg), triphenylphosphine (159 mg) and diethyl 1,2-diazenedicarboxylate (78 mg) at room temperature and the mixture was stirred at room temperature for 80 hours under nitrogen. The mixture was evaporated under reduced pressure. The residue was purified by column chromatography on silica gel (hexane/ethyl acetate=8/2) to give a carboxylate product. To a solution of the product in methanol (2 ml)/tetrahydrofuran (1 ml) was added aqueous solution of sodium hydroxide (1N, 0.62 ml) at room temperature and the mixture was stirred at 50° C. for 3 hours. The mixture solution was acidified with aqueous hydrochloric acid solution (1N), poured into water and extracted with ethyl acetate. The organic layer was washed with brine, dried over sodium sulfate and evaporated under reduced pressure to give 4'-[2-[(tert-butoxycarbonyl)[(2R)-2-phenyl-2-(tetrahydro-2H-pyran-2-yloxy)ethyl]amino]ethyl]-3-isobutoxy-4-biphenylcarboxylic acid (129 mg).

(−)ESI-MS (m/z): 616 (M−H)−

EXAMPLE 1

To a solution of tert-butyl [2-(4-bromophenyl)ethyl]-[(2R)-2-hydroxy-2-phenylethyl]carbamate (280 mg) in 1,2-dimethoxyethane (4 ml) was added methyl 4-(4,4,5,5-tetramethyl-1,3,2-dioxaborolan-2-yl)-2-(2-thienyl)benzoate (275 mg), tetrakis(triphenylphosphine)palladium (62 mg) and aqueous solution of sodium carbonate (2M, 0.7 ml), and the mixture was stirred at 80° C. for 4 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=3/1) to give methyl 4'-[2-[(tert-butoxycarbonyl) [(2R)-2-hydroxy-2-phenylethyl]amino]-ethyl]-3-(2-thienyl)-4-biphenylcarboxylate (191 mg).

MS (m/z): 558 (M+H)

EXAMPLE 2

The following compounds were obtained according to a similar manner to that of Example 1.
(1) tert-Butyl [(2R)-2-hydroxy-2-phenylethyl][2-[3'-isobutyl-4'-[[(methylsulfonyl)amino]carbonyl]-4-biphenylyl]ethyl]carbamate
MS (m/z): 593 (M−H)−
(2) tert-Butyl [(2R)-2-hydroxy-2-phenylethyl][2-[3'-(3-methylbutyl)-4'-[[(methylsulfonyl)amino]carbonyl]-4-biphenylyl]ethyl]carbamate
MS (m/z): 607 (M−H)−
(3) tert-Butyl [(1S,2R)-2-hydroxy-1-methyl-2-phenylethyl][2-[3'-isobutyl-4'-[[(methylsulfonyl)amino]carbonyl]-4-biphenylyl]ethyl]carbamate
MS (m/z): 607 (M−H)−
(4) Methyl 4'-[2-[(tert-butoxycarbonyl)[(1S,2R)-2-hydroxy-1-methyl-2-phenylethyl]amino]ethyl]-3-(isopropylthio)-4-biphenylcarboxylate
(+)ESI-MS (m/z): 586 (M+Na)+
(5) Methyl 4'-[2-[(tert-butoxycarbonyl)[(2R)-2-hydroxy-2-phenylethyl]amino]ethyl]-3-(isopropylthio)-4-biphenylcarboxylate
(+)ESI-MS (m/z): 572 (M+Na)+

EXAMPLE 3

The following compounds were obtained according to a similar manner to that of Preparation 14.
(1) Methyl 4'-[2-[(tert-butoxycarbonyl)[(1S,2R)-2-hydroxy-1-methyl-2-phenylethyl]amino]ethyl]-3-isobutyl-4-biphenylcarboxylate
ESI-MS (m/z): 568 (M+Na)+

(2) Methyl 4'-[2-[(tert-butoxycarbonyl)[(2R)-2-hydroxy-2-phenylethyl]amino]ethyl]-3-isopropoxy-4-biphenylcarboxylate (+) ESI-MS (m/z): 556 (M+Na)$^+$

EXAMPLE 4

To a solution of methyl 4'-[2-[(tert-butoxycarbonyl)-[(2R)-2-hydroxy-2-phenylethyl]amino]ethyl]-3-(2-thienyl)-4-bipheylcarboxylate (188 mg) in methanol (3.3 ml) was added 1N aqueous sodium hydroxide solution (1.0 ml), and the mixture was stirred at 40° C. for 3 hours. The solvent was removed by evaporation, and the aqueous solution was acidified with 1N aqueous hydrochloride solution and extracted with ethyl acetate (30 ml×2). The combined organic layers were washed with water and brine, dried over magnesium sulfate and evaporated under reduced pressure to give a benzoic acid product. To a solution of the product in ethyl acetate (1.0 ml) was added 4N hydrogen chloride in ethyl acetate (1.0 ml), and the mixture was stirred at room temperature for 12 hours. The resultant solid was collected by filtration and dried to give 4'-[2-[[(2R)-2-hydroxy-2-phenylethyl]amino]ethyl]-3-(2-thienyl)-4-biphenylcarboxylic acid hydrochloride (139 mg).

NMR (DMSO-$d_6$, δ): 2.98-3.23 (6H, m), 4.94-5.00 (1H, m), 6.21 (1H, br), 7.11-7.23 (2H, m), 7.36-7.41 (7H, m), 7.61-7.76 (6H, m), 9.10 (1H, br) MS (m/z): 442 (M-HCl—H)$^-$

EXAMPLE 5

The following compounds were obtained according to a similar manner to that of Example 4.
(1) 4'-[2-[[(1S,2R)-2-Hydroxy-1-methyl-2-phenylethyl]-amino]ethyl]-3-isobutyl-4-biphenylcarboxylic acid hydrochloride NMR (DMSO-$d_6$, δ): 0.88 (6H, d, J=6.5 Hz), 0.96 (3H, d, J=6.5 Hz), 1.79-1.92 (1H, m), 2.92 (2H, d, J=7.0 Hz), 3.02-3.10 (2H, m), 3.33-3.52 (3H, m), 5.15 (1H, br), 6.12 (1H, br), 7.26-7.61 (9H, m), 7.71 (2H, d, J=8.0 Hz), 7.87 (1H, d, J=8.0 Hz) MS (m/z): 432 (M-HCl+H)$^+$ (2) 4'-[2-[[(2R)-2-Hydroxy-2-phenylethyl]amino]ethyl]-3-(isopropylamino)-4-biphenylcarboxylic acid dihydrochloride NMR (DMSO-$d_6$, δ): 1.23 (6H, d, J=6.2 Hz), 2.90-3.40 (6H, m), 3.82-3.94 (1H, m), 5.00 (1H, dd, J=9.9, 2.7 Hz), 6.82 (1H, dd, J=8.3, 1.3 Hz), 6.92 (1H, s), 7.27-7.42 (7H, m), 7.66 (2H, d, J=8.1 Hz), 7.86 (1H, d, J=8.3 Hz), 8.91 (1H, br s), 9.28 (1H, br s) (−)ESI-MS (m/z): 417 (M−H)$^-$ (3) 4'-[2-[[(1S,2R)-2-Hydroxy-1-methyl-2-phenylethyl]-amino]ethyl]-3-(isopropylthio)-4-biphenylcarboxylic acid hydrochloride NMR (DMSO-$d_6$, δ): 0.96 (3H, d, J=6.7 Hz), 1.31 (6H, d, J=7.0 Hz), 3.02-3.48 (5H, m), 3.69-3.84 (1H, m), 5.20 (1H, s), 6.15 (1H, br s), 2.26-7.52 (8H, m), 7.6 (1H, d, J=1.1 Hz), 7.73 (2H, d, J=8.1 Hz), 7.91 (1H, d, J=8.1 Hz) (−)ESI-MS (m/z): 448 (M−H)$^-$

EXAMPLE 6

To a solution of tert-butyl [(2R)-2-hydroxy-2-phenylethyl] (2-[3'-(3-methylbutyl)-4'-[[(methylsulfonyl)amino]carbonyl]-4-biphenylyl]ethyl]carbamate (380 mg) in ethyl acetate (2.0 ml) was added 4N hydrogen chloride in ethyl acetate (2.0 ml), and the mixture was stirred at room temperature for 12 hours. The resultant solid was collected by filtration and dried to give 4'-[2-[[(2R)-2-hydroxy-2-phenylethyl]amino]ethyl]-3-(3-methylbutyl)-N-(methylsulfonyl)-4-biphenylcarboxamide hydrochloride (80 mg).

NMR (DMSO-$d_6$, δ): 0.91 (6H, d, J=6.2 Hz), 1.44-1.57 (3H, m), 2.77-2.85 (2H, m), 3.04-3.08 (3H, m), 3.20-3.32 (3H, m), 3.37 (3H, s), 4.94-5.00 (1H, m), 6.22 (1H, br), 7.32-7.42 (7H, m), 7.55-7.60 (3H, m), 7.70 (2H, d, J=8.0 Hz), 8.82-9.10 (2H, br) MS (m/z): 507 (M−HCl+H)$^+$

EXAMPLE 7

The following compounds were obtained according to a similar manner to that of Example 6.
(1) 4'-[2-[[(2R)-2-Hydroxy-2-phenylethyl]amino]ethyl]-3-isobutyl-N-(methylsulfonyl)-4-biphenylcarboxamide hydrochloride NMR (DMSO-$d_6$, δ): 0.87 (6H, d, J=6.5 Hz), 1.82-1.86 (1H, m), 2.73 (2H, d, J=7.0 Hz), 3.02-3.08 (3H, m), 3.19-3.23 (3H, m), 3.36 (3H, s), 4.95-5.0.0 (1H, m), 6.22 (1H, br), 7.32-7.41 (7H, m), 7.53-7.61 (3H, m), 7.70 (2H, d, J=8.0 Hz), 8.83 (1H, br), 9.12 (1H, br) MS (m/z): 493 (M−HCl+H)$^+$ (2) 4'-[2-[[(1S,2R)-2-Hydroxy-1-methyl-2-phenylethyl]-amino]ethyl-]-3-isobutyl-N-(methylsulfonyl)-4-biphenylcarboxamide hydrochloride NMR (DMSO-$d_6$, δ): 0.87 (6H, d, J=6.5 Hz), 0.99 (3H, d, J=6.5 Hz), 1.81-1.88 (1H, m), 2.74 (2H, d, J=7.0 Hz), 3.05-3.13 (2H, m), 3.33-3.54 (3H, m), 3.37 (3H, s), 5.19 (1H, br), 6.14-6.16 (1H, br), 7.28-7.44 (7H, m), 7.52-7.63 (3H, m), 7.71 (2H, d, J=8.0 Hz), 8.88 (2H, br) MS (m/z): 507 (M-HCl—H)$^-$ (3) 4'-[2-[[(2R)-2-Hydroxy-2-phenylethyl]amino]ethyl]-3-(isopropylthio)-N-(methylsulfonyl)-4-biphenylcarboxamide hydrochloride NMR (DMSO-$d_6$, δ): 1.26 (6H, d, J=6.6 Hz), 3.00-3.30 (6H, m), 3.65 (1H, m), 4.95-5.00 (1H, m), 6.22 (1H, d, J=3.7 Hz), 7.30-7.42 (7H, m), 7.61 (2H, s), 7.70-7.74 (3H, m) (−) ESI-MS (m/z): 511 (M−H)$^-$

EXAMPLE 8

To a solution of methyl 4'-[2-(benzylamino)ethyl]-3-(isopropylamino)-4-biphenylcarboxylate (250 mg) in ethanol (15 ml) was added (R)-(+)-styreneoxide (142 µl) at room temperature, and the mixture was stirred under reflux for 48 hours. The mixture was evaporated under reduced pressure. The residue was purified by column chromatography on silica gel (hexane/ethyl acetate=3/1) to give methyl 4'-[2-[benzyl [(2R)-2-hydroxy-2-phenylethyl]amino]ethyl]-3-(isopropylamino)-4-biphenylcarboxylate (251 mg).

(+) ESI-MS (m/z): 523 (M+H)$^+$

EXAMPLE 9

To methyl 4'-[2-[benzyl[(2R)-2-hydroxy-2-phenylethyl] amino]ethyl]-3-(isopropylamino)-4-biphenylcarboxylate (240 mg) was added 4N hydrogen chloride solution in ethyl acetate (287 µl) and evaporated under reduced pressure. The suspension of the obtained hydrochloride in methanol (2.5 ml) and tetrahydrofuran (2.5 ml) was hydrogenated over palladium on carbon (10% w/w, 50% wet, 24 mg) under hydrogen atmosphere for 2.5 hours. The catalyst was filtered off and the filtrate was evaporated under reduced pressure. To a solution of the residue in tetrahydrofuran (2.5 ml) and water (2.5 ml) was added di-tert-butyl dicarbonate (110 mg) tetrahydrofuran solution at 0° C. and the mixture was stirred at room temperature for 30 minutes. The mixture was poured into water, extracted with ethyl acetate, washed with brine, dried over magnesium sulfate and evaporated under reduced pressure. The residue was purified by column chromatography on silica gel (hexane/ethyl acetate=3/1) to give methyl 4'-[2-[(tert-butoxycarbonyl)[(2R)-2-hydroxy-2-phenylethyl]amino]ethyl]-3-(isopropylamino)-4-biphenylcarboxylate (170 mg).

(+) ESI-MS (m/z): 555 (M+Na)$^+$

EXAMPLE 10

To a solution of methyl 4'-[2-[(tert-butoxycarbonyl)-[(2R)-2-hydroxy-2-pyhenylethyl]amino]ethyl]-3-(isopropylthio)-4-biphenylcarboxylate (864 mg) in methanol (16 ml) was added aqueous solution of sodium hydroxide (1N, 4.71 ml) at room temperature and the mixture was stirred at 50° C. for 2.5 hours. The mixture solution was acidified with 1N aqueous hydrochloric acid solution, poured into water and extracted with ethyl acetate. The organic layer was washed with brine, dried over magnesium sulfate and evaporated under reduced pressure. The residue was purified by column chromatography on silica gel (hexane/ethyl acetate=1/1) to give 4'-[2-[(tert-butoxycarbonyl)[(2R)-2-hydroxy-2-phenylethyl]amino]ethyl]-3-(isopropylthio)-4-biphenylcarboxylic acid (695 mg).

(−)ESI-MS (m/z): 534 (M−H)$^-$

EXAMPLE 11

To a solution of methyl 4'-[2-[(tert-butoxycarbonyl)-[(2R)-2-hydroxy-2-phenylethyl]amino]ethyl]-3-isopropoxy-4biphenylcarboxylate (1.40 g) in methanol (15 ml)/tetrahydrofuran (6 ml) was added aqueous solution of sodium hydroxide (1N, 7.89 ml) at room temperature and the mixture was stirred at room temperature for 18 hours. The mixture solution was acidified with aqueous hydrochloric acid solution (1N), poured into water and extracted with ethyl acetate. The organic layer was washed with brine, dried over sodium sulfate and evaporated under reduced pressure. The residue was purified by column chromatography on silica gel (hexane/ethyl acetate=5/5) to give 4'-[2-[(tert-butoxycarbonyl)[(2R)-2-hydroxy-2-phenylethyl]amino]-ethyl]-3-isopropoxy-4-biphenylcarboxylic acid (1.40 g).

(−)ESI-MS (m/z): 518 (M−H)$^-$

EXAMPLE 12

To a solution of 4'-[2-[(tert-butoxycarbonyl)[(2R)-2-hydroxy-2-phenylethyl]amino]ethyl]-3-(isopropylthio)-4-biphenycarboxylic acid (131 mg) in N,N-dimethylformamide (2.6 ml) were added methanesulfonamide (24.9 mg), 4-(dimethylamino)pyridine (43.7 mg) and 1-(3-dimethylaminopropyl)-3-ethylcarbodiimide hydrochloride (91.4 mg) at room temperature and the mixture was stirred at the same temperature for 72 hours. The mixture was poured into aqueous hydrochloric acid solution (0.3N) and extracted with ethyl acetate. The organic layer was washed with brine, dried over magnesium sulfate and evaporated under reduced pressure. The residue was purified by column chromatography on silica gel (hexane/ethyl acetate=2/3) to give tert-butyl [(2R)-2-hydroxy-2-phenylethyl](2-[3'-(isopropylthio)-4'-[[(methylsulfonyl)amino]carbonyl]-4-biphenylyl]ethyl]-carbamate (10 mg).

(+)ESI-MS (m/z): 635 (M+Na)$^+$

EXAMPLE 13

The following compound was obtained according to a similar manner to that of Example 12.

tert-Butyl [(2R)-2-hydroxy-2-phenylethyl][2-[3'-isopropoxy-4'-[[(methylsulfonyl)amino]carbonyl]-4-biphenylyl]ethyl]carbamate (+)ESI-MS (m/z): 619 (M+Na)$^+$

EXAMPLE 14

To a solution of tert-butyl [2-[3'-(cyclohexyloxy)-4'-[[(methylsulfonyl)amino]carbonyl]-4-biphenylyl]ethyl][(2R)-2-hydroxy-2-phenylethyl]carbamate (89 mg) in 1,4-dioxane (2 ml) was added 4N hydrogen chloride solution in 1,4-dioxane (4 ml) at room temperature and the mixture was stirred at the same temperature for 2 hours. The mixture was evaporated under reduced pressure to give 3-(cyclohexyloxy)-4'-[2-[[(2R)-2-hydroxy-2-phenylethyl]amino]ethyl]-N-(methylsulfonyl)-4-biphenylcarboxamide hydrochloride (76 mg).

NMR (DMSO-d$_6$, δ): 1.32-1.81 (8H, m), 1.89-2.02 (2H, m), 2.98-3.30 (6H, m), 3.38 (3H, s), 4.75-4.87 (1H, m), 4.98-5.03 (1H, m), 6.23 (1H, d, J=3.8 Hz), 7.31-7.42 (9H, m), 7.71-7.80 (3H, m) (+)ESI-MS (m/z): 537 (M+H)$^+$

EXAMPLE 15

The following compound was obtained according to a similar manner to that of Example 14.

4'-[2-[[(2R)-2-Hydroxy-2-phenylethyl]amino]ethyl]-3-isobutoxy-N-(methylsulfonyl)-4-biphenylcarboxamide hydrochloride NMR (DMSO-d$_6$, δ): 1.05 (6H, d, J=6.6 Hz), 2.04-2.17 (1H, m), 2.99-3.23 (6H, m), 3.37 (3H, s), 4.03 (2H, d, J=6.2 Hz), 4.98-5.03 (1H, m), 6.23 (1H, d, J=3.9 Hz), 7.32-7.41 (9H, m), 7.70-7.78 (3H, m) (+)ESI-MS (m/z): 511 (M+H)$^+$

EXAMPLE 16

The following compounds were obtained according to a similar manner to that of Preparation 14 followed by a similar manner to that of Example 4.

(1) 3-Cyclopentyl-4'-[2-[[(2R)-2-hydroxy-2-phenylethyl]-amino]ethyl]-4-biphenylcarboxylic acid hydrochloride NMR (DMSO-d$_6$, δ): 1.5-2.2 (8H, m), 2.9-3.7 (6H, m), 3.82 (1H, m), 4.98 (1H, m), 6.20 (1H, m), 7.1-7.8 (12H, m) MS (m/z): 430 (M+H)

(2) 3-Cyclopentyl-4'-[2-([(1S,2R)-2-hydroxy-1-methyl-2-phenylethyl]amino]ethyl]-4-biphenylcarboxylic acid hydrochloride NMR (DMSO-d$_6$, δ): 0.94 (3H, d, J=6.8 Hz), 1.5-2.2 (8H, m), 3.0-3.7 (5H, m), 3.82 (1H, m), 5.19 (1H, m), 6.15 (1H, m), 7.1-7.8 (12H, m) MS (m/z): 444 (M+H)

(3) 4'-[2-[[(1S,2R)-2-Hydroxy-1-methyl-2-phenylethyl]-amino]ethyl]-3-isopropoxy-4-biphenylcarboxylic acid hydrochloride NMR (DMSO-d$_6$, δ): 0.97 (3H, d, J=6.6 Hz), 1.32 (6H, d, J=6.0 Hz), 3.0-3.6 (5H, m), 4.82 (1H, m), 5.21 (1H, m), 6.15 (1H, m), 7.1-7.5 (9H, m), 7.7-7.9 (3H, m) MS (m/z): 434 (M+H)

(4) 4'-[(2S)-3-Hydroxy-2-[[(2R)-2-hydroxy-2-phenylethyl]-amino]propyl]-3-isopropoxy-4-biphenylcarboxylic acid hydrochloride NMR (DMSO-d$_6$, δ): 1.31 (6H, d, J=6 Hz), 2.8-3.5 (7H, m), 4.82 (1H, m), 5.00 (1H, m), 5.41 (1H, m), 6.23 (1H, m), 7.2-7.8 (12H, m) MS (m/z): 450 (M+H)

(5) 4'-[2-[[(2R)-2-Hydroxy-2-phenylethyl]amino]-1-methylethyl)-3-isopropoxy-4-biphenylcarboxylic acid hydrochloride NMR (DMSO-d$_6$, δ): 1.31 (6H, d, J=6.0 Hz), 1.35 (3H, d, J=6.6 Hz), 2.8-3.5 (5H, m), 4.82 (1H, m), 5.02 (1H, m), 6.17 (1H, m), 7.2-7.5 (9H, m), 7.6-7.9 (3H, m) MS (m/z): 434 (M+H)

EXAMPLE 17

The following compounds were obtained according to a similar manner to that of Preparation 14 followed by a similar manner to that of Example 6.

(1) 3-(Cyclohexyloxy)-4'-[2-[[(1S,2R)-2-hydroxy-1-methyl-2-phenylethyl]amino]ethyl]-N-(methylsulfonyl)-4-biphenylcarboxamide hydrochloride NMR (DMSO-d$_6$, δ): 0.97 (3H, d, J=6.6 Hz), 1.3-2.1 (10H, m), 3.0-3.6 (5H, m), 4.82 (1H, m), 5.20 (1H, m), 6.16 (1H, m), 7.2-7.5 (9H, m), 7.7-7.9 (3H, m) MS (m/z): 551 (M+H)

(2) 3-(Cyclohexyloxy)-4'-[2-[[(2R)-2-hydroxy-2-(3-pyridyl)ethyl]amino)ethyl]-N-(methylsulfonyl)-4-biphenylcarboxamide dihydrochloride NMR (DMSO-d$_6$, δ): 1.2-2.1 (10H, m), 3.0-3.6 (5H, m), 4.81 (1H, m), 5.20 (1H, m), 7.2-7.4 (4H, m), 7.7-7.9 (3H, m), 7.9-8.0 (1H, m), 8.46 (1H, m), 8.82-8.89 (2H, m) MS (m/z): 538 (M+H)

EXAMPLE 18

To a solution of tert-butyl [(2R)-2-hydroxy-2-phenylethyl] [2-[3'-(isopropoxy)-4'-[[(methylsulfonyl)amino]-carbonyl]-4-biphenylyl]ethyl]carbamate (65 mg) in 1,4-dioxane (2 ml) was added hydrochloric acid 1,4-dioxane solution (4N, 4 ml) at room temperature and the mixture was stirred at the same temperature for 2.5 hours. The mixture was evaporated under reduced pressure to give 4'-[2-[[(2R)-2-hydroxy-2-phenylethyl]amino]ethyl]-3-isopropoxy-N-(methylsulfonyl)-4-biphenylcarboxamide hydrochloride (38 mg).

NMR (DMSO-d$_6$, δ): 1.37 (6H, d, J=5.7 Hz), 3.06-3.25 (6H, m), 3.38 (3H, s), 4.97-5.00 (2H, m), 6.23 (1H, br s), 7.28-7.48 (9H, m), 7.72-7.79 (3H, m) (+)ESI-MS (m/z): 497 (M+H)$^+$

EXAMPLE 19

To a solution of 4'-[2-[(tert-butoxycarbonyl)[(2R)-2-phenyl-2-(tetrahydro-2H-pyran-2-yloxy)ethyl]amino)ethyl]-3-isopropoxy-4-biphenylcarboxylic acid (224 mg) in N,N-dimethylformamide (2 ml) was added 1,1'-carbonyldiimidazole (72 mg) at room temperature and the mixture was stirred at the same temperature for 1 hour. 1-Pentanesulfonamide (67 mg) and 1,8-diazabicyclo[5.4.0]-7-undecene (0.067 ml) were added to the mixture at room temperature. The mixture was stirred at 70° C. for 4 hours. After cooling down to room temperature, the mixture was diluted with ethyl acetate, washed with aqueous hydrochloric acid solution (0.5N) and brine, dried over sodium sulfate and evaporated under reduced pressure to give residue (403 mg). To a solution of the above residue in methanol (2 ml) was added 4-methylbenzenesulfonic acid at room temperature and the mixture was stirred at the same temperature for 2 days. The mixture was diluted with ethyl acetate, washed with water and brine, dried over sodium sulfate and evaporated under reduced pressure. The residue was purified by column chromatography on silica gel (hexane/ethyl acetate=7/3) to give tert-butyl [(2R)-2-hydroxy-2-phenylethyl][2-[3'-isopropoxy-4'-[[(pentylsulfonyl)amino]carbonyl]-4-biphenylyl]ethyl]carbamate (179 mg).

(+)ESI-MS (m/z): 675 (M+Na)$^+$

EXAMPLE 20

To a solution of tert-butyl [(2R)-2-hydroxy-2-phenylethyl] [2-[3'-isopropoxy-4'-[[(pentylsulfonyl)amino]-carbonyl]-4-biphenylyl]ethyl]carbamate (170 mg) in ethyl acetate (2 ml) was added hydrochloric acid ethyl acetate solution (4N, 4 ml) at room temperature and the mixture was stirred at the same temperature overnight. The mixture was filtered to collect the precipitate and the precipitate was washed with ethyl acetate. The precipitate was dried under reduced pressure to give 4'-[2-[[(2R)-2-hydroxy-2-phenylethyl]amino]ethyl]-3-isopropoxy-N-(pentylsulfonyl)-4-biphenylcarboxamide hydrochloride (106 mg).

NMR (DMSO-d$_6$, δ): 0.87 (3H, t, J=7.0 Hz), 1.21-1.46 (4H, m), 1.36 (6H, d, J=6.0 Hz), 1.67-1.81 (2H, m), 2.99-3.29 (6H, m), 3.51 (2H, t, J=7.7 Hz), 4.91-5.05 (2H, m), 6.23 (1H, d, J=4.0 Hz), 7.32-7.43 (9H, m), 7.67-7.76 (3H, m) (+)ESI-MS (m/z): 553 (M+H)$^+$

EXAMPLE 21

The following compounds were obtained according to a similar manner to that of Example 19.

(1) tert-Butyl [(2R)-2-hydroxy-2-phenylethyl][2-[4'-[[(isobutylsulfonyl)amino]carbonyl]-3'-isopropoxy-4-biphenylyl]ethyl]carbamate (+)ESI-MS (m/z): 661 (M+Na)$^+$ (2) tert-Butyl [(2R)-2-hydroxy-2-phenylethyl][2-[3'-isopropoxy-4'-[[[(3-methylbutyl)sulfonyl]amino]-carbonyl]-4-biphenylyl]ethyl]carbamate (+)ESI-MS (m/z): 675 (M+Na)$^+$ (3) tert-Butyl [2-[4'-[[[(cyclohexylmethyl)sulfonyl]-amino]carbonyl]-3'-isopropoxy-4-biphenylyl]ethyl][(2R)-2-hydroxy-2-phenylethyl]carbamate (+)ESI-MS (m/z): 701 (M+Na)$^+$ (4) tert-Butyl [2-[4'-[[(benzylsulfonyl)amino]carbonyl]-3'-(cyclohexyloxy)-4-biphenylyl]ethyl][(2R)-2-hydroxy-2-phenylethyl]carbamate (+)ESI-MS (m/z): 735 (M+Na)$^+$

EXAMPLE 22

The following compounds were obtained according to a similar manner to that of Example 6.

(1) 4'-[2-[[(2R)-2-Hydroxy-2-phenylethyl]amino]ethyl]-N-(isobutylsulfonyl)-3-isopropoxy-4-biphenylcarboxamide hydrochloride NMR (DMSO-d$_6$, δ): 1.06 (6H, d, J=7.0 Hz), 1.36 (6H, d, J=6.0 Hz), 2.10-2.30 (1H, m), 2.99-3.27 (6H, m), 3.44 (2H, d, J=6.6 Hz), 4.92-5.05 (2H, m), 6.24 (1H, d, J=4.0 Hz), 7.32-7.43 (9H, m), 7.68-7.76 (3H, m) (+)ESI-MS (m/z): 539 (M+H)$^+$ (2) 4'-[2-[[(2R)-2-Hydroxy-2-phenylethyl]amino]ethyl]-3-isopropoxy-N-[(3-methylbutyl)sulfonyl]-4-biphenylcarboxamide hydrochloride NMR (DMSO-d$_6$, δ): 0.90 (6H, d, J=6.0 Hz), 1.36 (6H, d, J=6.0 Hz), 1.55-1.78 (3H, m), 2.90-3.27 (6H, m), 3.48-3.55 (2H, m), 4.91-5.05 (2H, m), 6.23 (1H, d, J=3.5 Hz), 7.32-7.43 (9H, m), 7.66-7.75 (3H, m) (+)ESI-MS (m/z): 553 (M+H)$^+$ (3) N-[(Cyclohexylmethyl)sulfonyl]-4'-[2-[[(2R)-2-hydroxy-2-phenylethyl]amino]ethyl]-3-isopropoxy-4-biphenylcarboxamide hydrochloride NMR (DMSO-d$_6$, δ): 1.09-1.31 (5H, m), 1.36 (6H, d, J=6.0 Hz), 1.53-1.73 (3H, m), 1.80-1.97 (3H, m), 3.02-3.27 (6H, m), 3.45 (2H, d, J=6.0 Hz), 4.92-5.04 (2H, m), 6.23 (1H, d, J=3.5 Hz), 7.31-7.43 (9H, m), 7.68-7.76 (3H, m) (+)ESI-MS (m/z): 579 (M+H)$^+$

EXAMPLE 23

The following compound was obtained according to a similar manner to that of Example 18.

N-(Benzylsulfonyl)-3-(cyclohexyloxy)-4'-[2-[[(2R)-2-hydroxy-2-phenylethyl]amino]ethyl]-4-biphenyl-carboxamide hydrochloride NMR (DMSO-d$_6$, δ): 1.14-1.69 (8H, m), 1.74-1.92 (2H, m), 2.97-3.29 (6H, m), 4.68-4.81 (1H, m), 4.87 (2H, s), 4.95-5.06 (1H, m), 6.23 (1H, d, J=3.8 Hz), 7.28-7.46 (14H, m), 7.67-7.81 (3H, m) (+)ESI-MS (m/z): 613 (M+H)$^+$ Preparation 18

To a mixture of (1R)-2-amino-1-(3-pyridyl)ethanol dihydrochloride (260 g), (4-bromophenyl)acetic acid (278 g), 1-hydroxybenzotriazole (175 g) and 1-[3-(dimethylamino)propyl]-3-ethylcarbodiimide hydrochloride (248 g) in N,N-dimethylformamide (1.3 l) was added triethylamine (361 l) at ambient temperature for 1 hour. The mixture was stirred at room temperature overnight. To the mixture was added water (1.3 l). The mixture was poured into water (1.6 l) and basified with 24% aqueous sodium hydroxide solution. The mixture was stirred at room temperature for 5 hours. The precipitate was collected by filtration, washed with water and dried in vacuo to give 2-(4-bromophenyl)-N-[(2R)-2-hydroxy-2-(3-pyridyl)ethyl]acetamide (335 g).

(+)ESI-MS (m/z): 335 (M+H)$^+$

Preparation 19

To a mixture of 2-(4-bromophenyl)-N-[(2R)-2-hydroxy-2-(3-pyridyl)ethyl]acetamide (160 g) in tetrahydrofuran (1.6 l) was added dropwise 2M borane-dimethylsulfide complex in tetrahydrofuran (716 ml) below 0° C. over 5 hours. The mixture was warmed up to 60° C. and stirred at the same temperature for 3 hours. The reaction mixture was cooled in ice bath (below 5° C.). To the cooled reaction mixture were added methanol and conc. hydrochloric acid (hydrogen gas was evolved). The mixture was heated and stirred at 60° C. for 1 hour, stood overnight at ambient temperature. The mixture was concentrated in vacuo and water was removed as azeotrope with butanol (480 ml). The concentrate was pulverized with isopropyl ether (1.5l). The precipitate was collected by filtration, washed with isopropyl ether and dried in vacuo to give (1R)-2-[[2-(4-bromophenyl)ethyl]amino]-1-(3-pyridyl)ethanol dihydrochloride (226 g).

(+)ESI-MS (m/z): 321 (M+H)$^+$

Preparation 20

(1R)-2-[[2-(4-Bromophenyl)ethyl]amino]-1-(3-pyridyl)ethanol dihydrochloride (188 g) was dissolved in water (750 ml) and tetrahydrofuran (750 ml) was added. pH of the solution was adjusted to 7.5 with 5N aqueous sodium hydroxide solution (90 ml). To the solution was added di-tert-butyl dicarbonate (115 g) in tetrahydrofuran (100 ml) dropwise at room temperature over 18 minutes, keeping the pH at 7.5-7.6 with aqueous sodium hydrodxide solution. The solution was stirred at room temperature for 1 hour. The mixture was partitioned between ethyl acetate (1.5 l) and water (1.5 l). The organic layer was separated and washed with water (1.5 l) and brine (1.5 l) dried over sodium sulfate, and evaporated under reduced pressure to give tert-butyl [2-(4-bromophenyl)ethyl] [(2R)-2-hydroxy-2-(3-pyridyl)ethyl]carbamate (187 g).

(+)ESI-MS (m/z): 421 (M+H)$^+$

Preparation 21

A mixture of 1-iodo-3-methylbutane (12 g) and potassium thiocyanate (5.9 g) in acetone (110 ml) was refluxed for 4 hours. After precipitate was filtered off, the filtrate was evaporated in vacuo. Water was added to the residue followed by extraction with chloroform. The extract was dried over magnesium sulfate and evaporated under reduced pressure to give the thiocyanate (8.3 g). A solution of above thiocyanate was bubbled with chlorine gas for 1 hour under ice-cooling (below 0° C.) with stirring followed by extraction with diisopropyl ether. After extract was dried over sodium sulfate, the solvent was evaporated in vacuo to give sulfonyl chloride (9.0 g). To a 28% ammonium hydroxide (50 ml) was added dropwise crude sulfonyl chloride in dichloromethane (15 ml) over 20 minutes at approximately 0° C. The reaction mixture was stirred vigorously overnight at ambient temperature. The phases were separated. The aqueous phase was extracted with chloroform/methanol (5/1). The combined organic extracts were washed with half-brine, dried over magnesium sulfate and evaporated under reduced pressure. The residue was purified by column chromatography on silica gel (chloroform/methanol=95/5) to give 3-methyl-1-butanesulfonamide (4.3 g).

(+)ESI-MS (m/z): 174 (M+Na)$^+$

Preparation 22

The following compound was obtained according to a similar manner to that of Preparation 21.

1-Cyclohexylmethanesulfonamide (+)ESI-MS (m/z): 200 (M+Na)$^+$

Preparation 23

To a mixture of methyl 4'-[2-[(tert-butoxycarbonyl)-[(2R)-2-phenyl-2-(tetrahydro-2H-pyran-2-yloxy)ethyl]amino]]-ethyl]-3-hydroxy-4-biphenylcarboxylate (173 mg) in N,N-dimethylformamide (2 ml) were added potassium carbonate (49 mg) and iodomethane (0.03 ml) at room temperature and the mixture was stirred at room temperature overnight. The mixture was poured into water and extracted with ethyl acetate. The organic layer was separated, washed with aqueous hydrochloric acid solution (0.1N) and brine, dried over sodium sulfate and evaporated under reduced pressure. To a mixture of the above residue (170 mg) in methanol (1.5 ml)/tetrahydrofuran (1 ml) was added aqueous sodium hydroxide solution (1N, 0.86 ml) at room temperature and the mixture was stirred at 50° C. for 3 hours. The mixture was acidified with aqueous hydrochloric acid solution (1N, 0.87 ml), poured into water and extracted with ethyl acetate. The organic layer was washed with brine, dried over sodium sulfate and evaporated under reduced pressure to give 4'-[2-[(tert-butoxycarbonyl)[(2R)-2-phenyl-2-(tetrahydro-2H-pyran-2-yloxy)ethyl]amino]ethyl]-3-methoxy-4-biphenylcarboxylic acid (159 mg).

(−)ESI-MS (m/z): 574 (M−H)$^−$

Preparation 24

To a ammonium hydroxide (28%, 80 ml) was added a solution of 4-bromo-2-fluorobenzenesulfonyl chloride (10 g) in dichloromethane (80 ml) dropwise for 1 hour at approximately 0° C. The reaction mixture was stirred vigorously for an additional 2 hours at the same temperature. The phases were separated. The aqueous phase was washed with dichloromethane. The combined organic extracts were washed with brine, dried over sodium sulfate and evaporated to give 4-bromo-2-fluorobenzenesulfonamide (8.0 g).

(+)ESI-MS (m/z): 276 (M+Na)+

Preparation 25

To a suspension of sodium hydride (60%, 0.65 g) in N,N-dimethylformamide (22 ml) was added a solution of cyclohexanol (2.7 ml) in N,N-dimethylformamide (6 ml) for 30 minutes at ambient temperature. The suspension was stirred for 30 minutes at room temperature. A solution of 4-bromo-2-fluorobenzenesulfonamide (3 g) in N,N-dimethylformamide (13 ml) was added dropwise over 30 minutes at ambient temperature. The suspension was stirred at room temperature for 1 hour and at 60° C. for 2 hours. The suspension was poured into a mixture of ice (35 ml) and aqueous hydrochloric acid solution (1N, 35 ml), and the mixture was stirred at room temperature for 1 hour. The mixture was filtered to collect precipitate and the precipitate was washed with water and hexane. The precipitate was dried under reduced pressure to give 4-bromo-2-(clohexyloxy)benzenesulfonamide (3.6 g).

(+)ESI-MS (m/z): 356 (M+Na)+

Preparation 26

To a solution of 4-bromo-2-(cyclohexyloxy)benzenesulfonamide (3.6 g) in 1,4-dioxane (35 ml) were added bis (pinacolate)diboron (3.0 g), dichlorobis-(triphenylphosphine)palladium(II) (528 mg) and potassium acetate (3.16 g), and the mixture was stirred at 95° C. for 2 hours under nitrogen atmosphere. After cooling down to room temperature, the mixture was poured into brine and extracted with ethyl acetate. The organic layer was separated, washed with brine, dried over sodium sulfate and evaporated under reduced pressure to give residue (6.4 g). To a mixture of the above residue in ethyl acetate (50 ml) and water (50 ml) were added ammonium acetate (1.8 g) and sodium periodate (5.0 g). The mixture was stirred at room temperature overnight. Precipitate was filtered off and the precipitate was washed with ethyl acetate/methanol (9/1). The filtrate was washed with aqueous hydrochloric acid solution (0.5N) and brine, dried over sodium sulfate and evaporated under reduced pressure. The residue was purified by column chromatography on silica gel (chloroform/methanol=95/5) to give [4-(aminosulfonyl)-3-(cyclohexyloxy)phenyl]boronic acid (2.5 g).

(+)ESI-MS (m/z): 322 (M+Na)+

Preparation 27

To a solution of methyl 3-(isopropylthio)-4'-[2-methyl-2-[(trifluoroacetyl)amino]propyl]-4-biphenylcarboxylate (810 mg) in ethanol was added sodium hydroxide aqueous solution (1M, 9 ml) at room temperature and stirred under reflux for 4 hours. The resultant mixture was evaporated. The residue was dissolved with hydrogen chloride solution in ethanol (5.5M, 12 ml) and stirred at room temperature overnight. The resultant mixture was evaporated and dried to give ethyl 4'-(2-amino-2-methylpropyl)-3-(isopropylthio)-4-biphenylcarboxylate (384 mg).

(+)ESI-MS (m/z): 372 (M+H)+

Preparation 28

To a solution of 4-bromo-2-chlorobenzoic acid (2 g), copper bromide(I) (122 mg) and potassium carbonate (2.35 g) in N,N-dimethylformamide (20 ml) was added cyclohexylamine (972 µl) at room temperature and stirred at 150° C. overnight. The mixture was poured into water, acidified with concentrated hydrochloric acid and extracted with ethyl acetate. The organic layer was washed with brine, dried over magnesium sulfate and evaporated. The residue was purified by column chromatography on silica gel (hexane/ethyl acetate=3/1) to give a aniline product. To a suspension of the aniline product in methanol (6.5 ml) was added concentrated sulfuric acid (650 µl) at room temperature and stirred under reflux for 1 week. The mixture was poured into saturated sodium bicarbonate aqueous solution and extracted with ethyl acetate. The organic layer was washed with water and brine, dried over magnesium sulfate and evaporated to give methyl 4-bromo-2-(cyclohexylamino)benzoate (549 mg).

(+)ESI-MS (m/z): 312 (M+H)+

Preparation 29

The following compound was obtained according to a similar manner to that of Preparation 10 followed by a similar manner to that of Preparation 11.

Methyl 4'-[2-(benzylamino)ethyl]-3-(cyclohexylamino)-4-biphenylcarboxylate (+)ESI-MS (m/z): 443 (M+H)+

Preparation 30

To a solution of methyl 4'-[2-[benzyl[(2R)-2-hydroxy-2-phenylethyl]amino]ethyl]-3-nitro-4-biphenylcarboxylate (2.31 g) in methylene chloride (35 ml) were added dihydropyran (1.24 ml) and pyridinium p-toluenesulfonate (1.36 mg) and stirred overnight at room temperature. The mixture was poured into saturated sodium bicarbonate aqueous solution and extracted with ethyl acetate. The organic layer was washed with saturated sodium bicarbonate aqueous solution twice and brine, dried over magnesium sulfate and evaporated. The residue was purified by column chromatography on silica gel (hexane/ethyl acetate=3/1) to give methyl 4'-[2-[benzyl[(2R)-2-phenyl-2-(tetrahydro-2H-pyran-2-yloxy)ethyl]-amino]ethyl]-3-nitro-4-biphenylcarboxylate (1.48 g).

(+)ESI-MS (m/z): 595 (M+H)+

Preparation 31

To a solution of methyl 4'[2-[benzyl[(2R)-2-phenyl-2-(tetrahydro-2H-pyran-2-yloxy)ethyl]amino]ethyl]-3-nitro-4-biphenylcarboxylate (1.44 g) in ethanol (30 ml) and water (10 ml) were added iron (406 mg) and ammonium chloride (65 mg) and stirred under reflux for 1.5 hours. The mixture was filtrated through Celite pad and evaporated. The residue was dissolved with ethyl acetate, chloroform and methanol, washed with saturated sodium bicarbonate aqueous solution and brine, dried over magnesium sulfate and evaporated to give methyl 3-amino-4'-[2-[benzyl[(2R)-2-phenyl-2-(tetrahydro-2H-pyran-2-yloxy)ethyl]amino]ethyl]-4-biphenylcarboxylate (1.18 g).

(+)ESI-MS (m/z): 565 (M+H)+

Preparation 32

To a solution of methyl 3-amino-4'-[2-[benzyl[(2R)-2-phenyl-2-(tetrahydro-2H-pyran-2-yloxy)ethyl]amino]ethyl]-4-biphenylcarboxylate (532 mg) in pyridine (600 µl) was added acetic anhydride (400 µl) and stirred overnight at room temperature. The mixture was poured into water and extracted with ethyl acetate. The organic layer was washed with saturated ammonium chloride aqueous solution and brine, dried over magnesium sulfate and evaporated. The residue was purified by column chromatography on silica gel (hexane/ethyl acetate=3/1) to give methyl 3-(acetylamino)-4'-[2-[benzyl[(2R)-2-phenyl-2-(tetrahydro-2H-pyran-2-yloxy)ethyl] amino]ethyl]-4-biphenylcarboxylate (381 mg).

(+)ESI-MS (m/z): 607 (M+H)+

Preparation 33

To a solution of (αS,βR)-4-hydroxynorephedrine (500 mg) and 4-bromophenylethyl bromide (500 mg) in N,N-dimethylformamide (5 ml) was added N,N-diisopropylethylamine (0.5 ml), and the mixture was stirred for 6 hours at 80° C. The mixture was partitioned between ethyl acetate and water. The organic layer was washed with brine, dried over magnesium sulfate, and concentrated in vacuo. The residual oil was diluted in tetrahydrofuran (10 ml). To the solution was added di-tert-butyl dicarbonate (1 g) at room temperature, and the mixture was stirred at the same temperature for 12 hours. The resulting mixture was evaporated under pressure and the residue was purified by column chromatography on silica gel to give 4-[2-[[(1S,2R)-2-hydroxy-2-(4-hydroxyphenyl)-1-methylethyl](tert-butyloxycarbonyl)amino]ethyl]phenyl bromide (520 mg).

MS (m/z): 550 (M+H)

Preparation 34

To a solution of 4-bromo-2-ethoxybenzoic acid (5.00 g) in N,N-dimethylformamide (50 ml) was added N,N'-carbonyldiimidazole (4.96 g) at room temperature and the mixture was stirred for 2 hours. To the mixture were added methanesulfonamide (2.13 g) and 1,8-diazabicyclo[5.4.0]-undec-7-ene (3.36 ml) and the whole was stirred at room temperature for 4 hours. The mixture was poured into 1N hydrochloric acid (100 ml) and extracted with ethyl acetate (100 ml). The organic layer was separated and washed successively with water (100 ml×2), 1N hydrochloric acid (100 ml), and brine (100 ml). The solution was dried over magnesium sulfate and concentrated in vacuo to give a white solid (6.42 g). The crude product was chromatographed on silica gel (eluent: hexane/ethyl acetate) to give 4-bromo-2-ethoxy-N-(methylsulfonyl)benzamide (2.75 g) as a white solid.

(−)ESI-MS (m/z): 320, 322 (M−H)⁻

Preparation 35

A mixture of 4-bromo-2-ethoxy-N-(methylsulfonyl)benzamide (2.73 g), bis(pinacolato)diboron (2.37 g), bis(triphenylphosphine)palladium(II) chloride (220 mg), potassium acetate (3.33 g) and 1,4-dioxane (27 ml) was stirred at 95° C. for 2 hours. After cooling to room temperature, the mixture was quenched by the addition of water (60 ml) and extracted with ethyl acetate (60 ml). The organic layer was separated and washed with water (60 ml×2). To the organic layer were added water (60 ml), ammonium acetate (2.94 g) and sodium periodate (6.34 g). The mixture was stirred at room temperature overnight. The insoluble solid was filtered off and washed with ethyl acetate, and the organic layer was separated. The organic layer was washed with 0.5N hydrochloric acid (60 ml) and brine (60 ml), and dried over magnesium sulfate. Filtration followed by evaporation gave a white solid (2.00 g) which was chromatographed on silica gel (eluent: chloroform/methanol) to give [3-ethoxy-4-[[(methylsulfonyl)amino]carbonyl]-phenyl]boronic acid (1.16 g) as a white solid.

(−)ESI-MS (m/z): 286 (M−H)⁻

Preparation 36

To a suspension of [2-(4-iodophenoxy)ethyl]amine hydrochloride (7.0 g) in chloroform (70 ml) was added saturated sodium bicarbonate solution (70 ml) and the mixture was warmed to 50° C. and stirred for 15 minutes. The organic layer was separated and dried over magnesium sulfate. Filtration followed by evaporation gave [2-(4-iodophenoxy)ethyl]amine (6.13 g) as a white solid. The compound was used in the next step without further purification.

Preparation 37

To a solution of [2-(4-iodophenoxy)ethyl]amine (6.14 g) in dimethyl sulfoxide (50 ml) was added N,O-bis(trimethylsilyl)acetamide (2.88 ml) and the mixture was stirred for 1 hour. To the mixture was added a solution of (2R)-2-(4-nitrophenyl)oxirane (3.21 g) in dimethyl sulfoxide (10 ml) and the mixture was stirred for 37 hours. After cooling to room temperature, the mixture was quenched by the addition of 5% acetic acid/water (120 ml) and stirred for 30 minutes. The mixture was basified with 1N sodium hydroxide and extracted with ethyl acetate (120 ml). The extract was washed with water (120 ml×2) and brine (120 ml), and dried over magnesium sulfate. Filtration followed by evaporation gave (1R)-2-[[2-(4-iodophenoxy)ethyl]amino]-1-(4-nitrophenyl)ethanol (7.52 g) as a brown solid. The compound was used in the next step without further purification.

Preparation 38

To a solution of (1R)-2-[[2-(4-iodophenoxy)ethyl]-amino]-1-(4-nitrophenyl)ethanol (7.52 g) in tetrahydrofuran (75 ml) was added di-tert-butyl dicarbonate (4.44 ml) and the mixture was stirred for 16 hours. The solvent was removed by evaporation and the residue was chromatographed on silica gel (eluent: hexane/ethyl acetate) to give tert-butyl [(2R)-2-hydroxy-2-(4-nitrophenyl)ethyl][2-(4-iodophenoxy)ethyl]carbamate (3.48 g) as an orange paste.

(+)ESI-MS (m/z): 551 (M+Na)⁺

Preparation 39

The following compound was obtained according to a similar manner to that of Preparation 38.

tert-Butyl [(2R)-2-[6-(acetylamino)-3-pyridyl]-2-[[tert-butyl(dimethyl)silyl]oxy]ethyl][2-(4-bromophenyl)ethyl]carbamate (+)ESI-MS (m/z): 614 and 616 (M+Na)⁺

Preparation 40

To a mixture of (2R)-2-[6-(acetylamino)-3-pyridyl]-2-[[tert-butyl(dimethyl)silyl]oxy]ethyl 4-methylbenzenesulfonate (3.50 g), (2-(4-bromophenyl)ethyl]-amine (3.01 g) and dimethyl sulfoxide (1.75 ml) was added N,N-diisopropylethylamine (1.31 ml) and the mixture was stirred at 80° C. for 24 hours. After cooling to room temperature, the mixture was diluted with ethyl acetate (35 ml) and water (35 ml), and the organic layer was separated. The organic layer was washed with water (35 ml×2) and brine (35 ml), and dried over magnesium sulfate. Filtration followed by evaporation gave a yellow paste (5.36 g) which was chromatographed on silica gel (eluent: hexane/ethyl acetate) to give N-[5-[(1R)-2-[[2-(4-bromophenyl)ethyl]-amino]-1-[[tert-butyl(dimethyl)silyl]oxy]ethyl]-2-pyridyl]acetamide (3.33 g) as a colorless paste.

(+)ESI-MS (m/z): 492 and 494 (M+H)⁺

Preparation 41

To a solution of [4-[2-[benzyl(tert-butoxycarbonyl)amino]ethyl]phenyl]boronic acid (3.1 g) in 1,2-dimethoxyethane (45 ml) were added methyl 3-nitro-4-[[(trifluoromethyl)sulfonyl]oxy]benzoate (3.0 g), tetrakis(triphenylphosphine)palladium (800 mg) and aqueous solution of sodium carbonate (2M, 9.1 ml), and the mixture was stirred at 80° C. for 4 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=3/1) to give methyl 4'-[2-[benzyl(tert-butoxycarbonyl)amino]ethyl]-2-nitro-4-biphenylcarboxylate (3.05 g).

MS (m/z): 491 (M+H)⁺

Preparation 42

The following compounds were obtained according to a similar manner to that of Preparation 41 followed by a similar manner to that of Preparation 11.

(1) Ethyl 4'-[2-(benzylamino)ethyl]-2-isobutyl-4-biphenylcarboxylate

NMR (CDCl$_3$, δ): 0.72 (6H, d, J=6.6 Hz), 1.41 (3H, t, J=7.2 Hz), 1.6-1.8 (1H, m), 2.5 (2H, d, J=7.2 Hz), 2.8-3.0 (4H, m), 3.8 (2H, s), 4.4 (2H, q, J=7.2 Hz), 7.2-7.4 (10H, m), 7.85-7.93 (2H, m) MS (m/z): 416 (M+H)$^+$ (2) Ethyl 4'-[2-(benzylamino)ethyl]-2-butyl-4-biphenylcarboxylate NMR (CDCl$_3$, δ): 0.78 (3H, t, J=7.2 Hz), 1.1-1.3 (2H, m), 1.4-1.54 (5H, m), 2.6 (2H, t, J=7.5 Hz), 2.86-3.0 (4H, m), 3.85 (2H, s), 4.4 (2H, q, J=7.1 Hz), 7.1-7.3 (10H, m), 7.8-8.0 (2H, m) MS (m/z): 416 (M+H)$^+$ Preparation 43

The following compounds were obtained according to a similar manner to that of Example 1.

(1) Methyl 4'-[2-[[(benzyloxy)carbonyl]amino]-2-methylpropyl]-3-isobutyl-4-biphenylcarboxylate NMR (CDCl$_3$, δ): 0.94 (6H, d, J=6.6 Hz), 1.33 (6H, s), 1.56 (9H, s), 2.92 (2H, d, J=7.0 Hz), 3.03 (2H, s), 3.90 (3H, s), 4.54 (1H, br), 5.12 (2H, s), 7.14 (2H, d, J=8.1 Hz), 7.33-7.47 (9H, m), 7.94 (2H, d, J=8.1 Hz) MS (m/z): 474 (M+H)$^+$ (2) Methyl 3-(isopropylthio)-4'-[2-methyl-2-[(trifluoroacetyl)amino]propyl]-4-biphenylcarboxylate (+)ESI-MS (m/z): 476 (M+Na)$^+$ (3) tert-Butyl [2-[3'-(isopropylamino)-4'-[(methylsulfonyl)amino]carbonyl]-4-biphenylyl]ethyl]-carbamate (−)ESI-MS (m/z): 474 (M−H)$^-$ (4) 4'-(2-Bromoethoxy)-3-(isopropylthio)-N-(methylsulfonyl)-4-biphenylcarboxamide (−)ESI-MS (m/z): 470 (M−H)$^-$ (5) Methyl 4'-(2-hydroxyethoxy)-3-(isopropylthio)-4-biphenylcarboxylate (+)ESI-MS (m/z): 369 (M+Na)$^+$ Preparation 44

The following compound was obtained according to a similar manner to that of Preparation 1.

tert-Butyl [3-(4-bromophenyl)propyl][(2R)-2-hydroxy-2-phenylethyl]carbamate

NMR (CDCl$_3$, δ): 1.46 (9H, s), 1.7-1.9 (2H, m), 2.5 (3H, t, J=7.4 Hz), 3.1-3.5 (4H, m), 3.37 (3H, s), 4.9-5.0 (1H, m), 7.0-7.4 (9H, m)

Preparation 45

The mixture of methyl 4'-[2-[[(benzyloxy)carbonyl]amino]-2-methylpropyl]-3-isobutyl-4-biphenylcarboxylate (570 mg), ammonium formate (351 mg) and palladium on carbon powder (400 mg) in methanol (10 ml) and water (1.0 ml) was refluxed for 3 hours. The catalyst was filtered off, and the filtrate was diluted with chloroform-methanol (19:1). The organic layer was washed with saturated aqueous sodium bicarbonate solution and brine, dried over magnesium sulfate, and evaporated to give methyl 4'-(2-amino-2-methylpropyl)-3-isobutyl-4-biphenylcarboxylate (372 mg).

NMR (CDCl$_3$, δ): 0.94 (6H, d, J=6.6 Hz), 1.16 (6H, s), 1.84-1.98 (1H, m), 2.71 (2H, s), 2.93 (2H, d, J=7.0 Hz), 3.90 (3H, s), 7.26-7.58 (6H, m), 7.95 (1H, d, J=6.6 Hz), 7.94 (2H, d, J=8.1 Hz)

Preparation 46

To a solution of 4-iodophenol (13.5 g) and tert-butyl (2-hydroxyethyl)carbamate (12.9 g) in tetrahydrofuran (110 ml) were added triphenylphosphine (20.9 g) and 40% diethyl 1,2-diazenedicarboxylate solution in toluene (36.2 ml) at 4° C. and the mixture was stirred at room temperature for 16 hours under nitrogen. The mixture was evaporated under reduced pressure. The residue was purified by column chromatography on silica gel (hexane/ethyl acetate=3/1 to give phenyl ether product (19.3 g). To a solution of the product in ethyl acetate (100 ml) was added 4N hydrogen chloride in ethyl acetate (100 ml), and the mixture was stirred at room temperature for 2.5 hours. The resultant solid was collected by filtration and dried to give [2-(4-iodophenoxy)ethyl]amine hydrochloride (15.5 g).

NMR (DMSO-d$_6$, δ): 3.2 (2H, t, J=5.0 Hz), 4.1 (2H, t, J=5.0 Hz), 6.8-6.9 (2H, m), 7.6-7.7 (2H, m), 8.2 (2H, br) MS (m/z): 264 (M-HCl+H)$^+$

Preparation 47

To a mixture of [2-(4-iodophenoxy)ethyl]amine hydrochloride (6.5 g), (2R)-hydroxy(phenyl)acetic acid (3.35 g) and hydroxybenzotriazole (3.0 g) in N,N-dimethylformamide (40 ml) was added 1-[3-(dimethylamino)propyl]-3-ethylcarbodiimide (3.42 g), and the mixture was stirred at room temperature for 3.5 hours. The mixture was partitioned between ethyl acetate and water. The organic layer was separated, washed by 1N-hydrochloric acid solution followed by saturated sodium bicarbonate solution, dried over magnesium sulfate and evaporated under reduced pressure to give an amide product (7.3 g). To a solution of the product in tetrahydrofuran (24 ml) and 1,3-dimethyl-2-imidazolidinone (24 ml) was added 1M boran-dimethylsulfide complex in tetrahydrofuran (55 ml) at 4° C., and the mixture was refluxed for 4 hours. To the mixture were added methanol (5.0 ml) and 12N-hydrochloride acid (7.0 g) dropwise below 15° C., and the mixture was refluxed for 1 hour. The mixture was cooled to room temperature and the solvent was removed by evaporation. To the residue, 30%-aqueous potassium carbonate solution below 10° C. was added. The mixture was partitioned between ethyl acetate and water. The organic layer was separated, washed with brine, dried over magnesium sulfate and evaporated under reduced pressure to give a solid. The solid was triturated with 2-propanol to give amine product (7.0 g). To a solution of the product in tetrahydrofuran (100 ml) and water (80 ml) was added di-tert-butyl dicarbonate (4.2 g) at room temperature. The pH was kept between 7 to 8 by using 1N aqueous sodium hydroxide solution. The mixture was stirred at room temperature for 1 hour. The mixture was partitioned between ethyl acetate and water. The organic layer was separated, washed with brine, dried over magnesium sulfate and evaporated under reduced pressure to give tert-butyl [(2R)-2-hydroxy-2-phenylethyl][2-(4-iodophenoxy)ethyl]carbamate (9.7 g).

NMR (CDCl$_3$, δ): 1.48 (9H, s), 3.5-3.6 (4H, m), 3.9-4.0 (2H, m), 4.9-5.0 (1H, m), 6.6-6.7 (2H, m), 7.3-7.6 (7H, m) MS (m/z): 506 (M+Na)$^+$

Preparation 48

The following compounds were obtained according to a similar manner to that of Preparation 47.

(1) tert-Butyl [(2R)-2-(3-chlorophenyl)-2-hydroxyethyl][2-(4-iodophenoxy)ethyl]carbamate NMR (CDCl$_3$, δ): 1.48 (9H, s), 3.5-3.6 (4H, m), 3.9-4.0 (2H, m), 4.9-5.0 (1H, m), 6.6-6.7 (2H, m), 7.26 (3H, br), 7.4 (1H, s), 7.5-7.6 (2H, m)

MS (m/z): 540 (M+Na)$^+$ (2) tert-Butyl [(2R)-2-(3-chlorophenyl)-2-hydroxyethyl][2-[(4-iodophenyl)amino]ethyl]carbamate NMR (CDCl$_3$, δ): 1.49 (9H, s), 3.1-3.5 (6H, m), 4.9-5.0 (1H, m), 6.3-6.4 (2H, m), 7.2-7.45 (6H, m) MS (m/z): 539 (M+Na)$^+$ Preparation 49

To a mixture of 4-iodoaniline (10 g), [(tert-butoxycarbonyl)amino]acetic acid (8.8 g) and 1-hydroxybenzotriazole (6.8 g) in N,N-dimethylformamide (80 ml) was added 1-[3-(dimethylamino)propyl]-3-ethylcarbodiimide hydrochloride (9.63 g), and the mixture was stirred at room temperature for 16 hours. The mixture was partitioned between ethyl acetate and water. The organic layer was separated, washed by 1N hydrochloric acid followed by saturated sodium bicarbonate solution, dried over magnesium sulfate and evaporated under reduced pressure to give an amide product (15.6 g). To a solution of the product in 1,4-dioxane (80 ml) was added 4N hydrogen chloride in 1,4-dioxane (80 ml), and the mixture was stirred at room temperature for 16 hours. The resultant solid was collected by filtration. The solid was triturated with ethyl acetate/hexane solution (1/1, 90 ml) to give 2-amino-N-(4-iodophenyl)acetamide hydrochloride (11.6 g).

NMR (DMSO-d$_6$, δ): 3.8 (2H, d, J=5.3 Hz), 7.4-7.5 (2H, m), 7.7-7.8 (2H, m), 8.2 (2H, br) MS (m/z): 299 (M-HCl+Na)$^+$

Preparation 50

The mixture of 4-iodophenol (6.0 g), 1,2-dibromoethane (26 ml) and potassium carbonate (5.28 g) was refluxed for 3 hours. The mixture was evaporated under reduced pressure. The residue was purified by column chromatography on silica gel (hexane/ethyl acetate=6/1) to give 1-(2-bromoethoxy)-4-iodobenzene (6.5 g).

NMR (CDCl$_3$, δ): 3.6 (2H, t, J=6.3 Hz), 4.3 (2H, t, J=6.2 Hz), 6.5-6.7 (2H, m), 7.5-7.6 (2H, m)

Preparation 51

To a solution of (1R,2S)-norephedrine (3.0 g) and 1-(2-bromoethoxy)-4-iodobenzene (6.5 g) in N,N-dimethylformamide (30 ml) was added N,N-diisopropylethylamine (3.8 ml), and the mixture was stirred for 3 hours at 80° C. The mixture was partitioned between ethyl acetate and water. The organic layer was washed with brine, dried over magnesium sulfate, and concentrated in vacuo. The resultant solid was diluted in tetrahydrofuran (70 ml). To the solution was added di-tert-butyl dicarbonate (4.85 g) and triethylamine (2.95 ml) at room temperature, and the mixture was stirred at the same temperature for 2.5 hours. The mixture was partitioned between ethyl acetate and water. The organic layer was washed with brine, dried over magnesium sulfate, and concentrated in vacuo. The residue was purified by column chromatography on silica gel (hexane/ethyl acetate=6/1) to give tert-butyl [(1S,2R)-2-hydroxy-1-methyl-2-phenylethyl][2-(4-iodophenoxy)ethyl]carbamate (7.2 g).

NMR (CDCl$_3$, δ): 1.25 (3H, d, J=7.0 Hz), 1.47 (9H, s), 3.4-3.5 (2H, m), 3.8-4.0 (2H, m), 4.2-4.3 (1H, m), 6.7 (2H, d, J=8.7 Hz), 7.2-7.4 (6H, m), 7.5-7.6 (2H, m)

Preparation 52

The following compounds were obtained according to a similar manner to that of Example 44.

(1) tert-Butyl [(2R)-2-[6-(acetylamino)-3-pyridyl]-2-[[(tert-butyl)(dimethyl)silyl]oxy]ethyl][2-[3'-isopropoxy-4'-[[(methylsulfonyl)amino]carbonyl]-4-biphenylyl]ethyl]carbamate (−)ESI-MS (m/z): 767 (M−H)$^-$ (2) tert-Butyl [(2R)-2-[6-(acetylamino)-3-pyridyl]-2-[[(tert-butyl)(dimethyl)silyl]oxy]ethyl][2-[3'-(cyclohexyloxy)-4'-[[(methylsulfonyl)amino]carbonyl]-4-biphenylyl]ethyl]carbamate (−)ESI-MS (m/z): 807 (M−H)$^-$ (3) Methyl 4'-[2-[[(2R)-2-[6-(acetylamino)-3-pyridyl]-2-[[(tert-butyl)(dimethyl)silyl]oxy]ethyl](tert-butoxycarbonyl)amino]ethyl]-3-isopropoxy-4-biphenylcarboxylate (+)ESI-MS (m/z): 706 (M+H)$^+$ (4) Methyl 4'-[2-[[(2R)-2-[6-(acetylamino)-3-pyridyl]-2-[[(tert-butyl)(dimethyl)silyl]oxy]ethyl](tert-butoxycarbonyl)amino]ethyl]-3-(cyclohexyloxy)-4-biphenylcarboxylate (+)ESI-MS (m/z): 768 (M+Na)$^+$ (5) Methyl 4'-[2-[[(2R)-2-[6-(acetylamino)-3-pyridyl]-2-[[(tert-butyl)(dimethyl)silyl]oxy]ethyl](tert-butoxycarbonyl)amino]ethyl]-3-(cycloheptyloxy)-4-biphenylcarboxylate (+)ESI-MS (m/z): 760 (M+H)$^+$ Preparation 53

The following compounds were obtained according to a similar manner to that of Example 3.

(1) Methyl 4'-[2-[(tert-butoxycarbonyl)[(2R)-2-phenyl-2-(tetrahydro-2H-pyran-2-yloxy)ethyl]amino]ethyl]-3-isopropoxy-4-biphenylcarboxylate (+)ESI-MS (m/z): 640 (M+Na)$^+$ (2) tert-Butyl [2-[4'-(aminosulfonyl)-3'-(cyclohexyloxy)-4-biphenylyl]ethyl][(2R)-2-phenyl-2-(tetrahydro-2H-pyran-2-yloxy)ethyl]carbamate (+)ESI-MS (m/z): 701 (M+Na)$^+$ Preparation 54

The following compound was obtained according to a similar manner to that of Example 11.

4'-[2-[(tert-Butoxycarbonyl) [(2R)-2-phenyl-2-(tetrahydro-2H-pyran-2-yloxy)ethyl]amino]ethyl]-3-isopropoxy-4-biphenylcarboxylic acid (−)ESI-MS (m/z): 602 (M−H)$^-$ Preparation 55

To a solution of methyl 4-chloro-2-nitrobenzoate (3.81 g) and [4-[2-[benzyl(tert-butoxycarbonyl)amino]ethyl]phenyl]boronic acid (6.91 g) in 1,4-dioxane (76 ml) were added cesium carbonate (8.64 g), potassium fluoride (3.08 g), tri-tert-butylphosphine (1.1 ml) and tris(dibenzylideneacetone)dipalladium(0) (1.62 g) under nitrogen at room temperature and then stirred at 80° C. for 3 hours. The mixture was diluted with ethyl acetate, filtrated through silica gel pad and evaporated. The residue was purified by column chromatography on silica gel (hexane/ethyl acetate=3/1) to give methyl 4'-[2-[benzyl(tert-butoxycarbonyl)amino]ethyl]-3-nitro-4-biphenylcarboxylate (3.41 g).

(+)ESI-MS (m/z): 513 (M+Na)$^+$

Preparation 56

The following compound was obtained according to a similar manner to that of Example 1 followed by Example 6.

4'-(2-Aminoethoxy)-3-(cyclohexyloxy)-N-(methylsulfonyl)-4-biphenylcarboxamide hydrochloride MS (m/z): 431 (M-HCl—H)$^-$ Preparation 57

The following compound was obtained according to a similar manner to that of Example 59.

tert-Butyl [(2R)-2-(4-chlorophenyl)-2-hydroxyethyl] [2-(4-iodophenoxy)ethyl]carbamate NMR (CDCl$_3$, δ): 1.48 (9H, s), 3.5-3.6 (4H, m), 3.9-4.0 (2H, m), 4.9-5.0 (1H, m), 6.6-6.7 (2H, m), 7.32 (4H, s), 7.5-7.6 (2H, m) MS (m/z): 540 (M+Na)$^+$ Preparation 58

To a suspension of sodium hydride (32.87 g) in dimethyl sulfoxide (600 ml) was added 2-propanethiol (41.73 ml) at 0° C. under nitrogen atmosphere and stirred at room temperature for 1 hour. The reaction mixture was cooled with ice bath and added 4-bromo-2-fluorobenzoic acid (60 g). The reaction mixture was stirred at 70° C. for 1.5 hours and then cooled to room temperature. The mixture was poured into water (3 l) and washed with hexane (600 ml). The water layer was acidified with concentrated hydrochloric acid and then the resulting white solid was collected by filtration. The white solid was dried at 60° C. to give 4-bromo-2-(isopropylthio)benzoic acid (75.49 g).

(−)ESI-MS (m/z): 273 (M−H)$^−$

Preparation 59

The following compound was obtained according to a similar manner to that of Preparation 9.

Methyl 4-bromo-2-(isopropylthio)benzoate (+)ESI-MS (m/z): 311 (M+Na)$^+$

Preparation 60

To a solution of 4-bromo-2-(isopropylthio)benzoic acid (47.90 g) in N,N-dimethylformamide (480 ml) was added 1,1'-carbonyldiimidazole (31.00 g) and stirred for 30 minutes at room temperature under nitrogen atmosphere. To the mixture were added methanesulfonamide (18.17 g) and 1,8-diazabicyclo[5.4.0]-7-undecene (39.10 ml) and then stirred at room temperature overnight. The reaction mixture was poured into hydrochloric acid aqueous solution (1N, 2 l) and extracted with ethyl acetate (2 l). The separated organic layer was washed with water (2 l) and brine (2 l), dried over magnesium sulfate and concentrated in vacuo. Then the residue was dried to give 4-bromo-2-(isopropylthio)-N-(methylsulfonyl)benzamide (60.00 g) as a white solid.

(−)ESI-MS (m/z): 350 (M−H)$^−$

Preparation 61

The following compounds were obtained according to a similar manner to that of Preparation 60.
(1) 4-Bromo-2-(isopropylamino)-N-(methylsulfonyl)benzamide
   (−)ESI-MS (m/z): 337 (M−H)$^−$
(2) 4-Bromo-2-(cyclohexylamino)-N-(methylsulfonyl)benzamide
   (−)ESI-MS (m/z): 373, 375 (M−H)$^−$ Preparation 62

To a solution of 4-bromo-2-(isopropylthio)-N-(methylsulfonyl)benzamide (59 g) in 1,4-dioxane (1.0 l) were added bis(pinacolato)diboran (42.50 g), 1,1'-bis(diphenylphosphino)ferrocene (9.29 g) potassium acetate (65.8 g) and 1,1'-bis(diphenylphosphino)ferrocenedichloropalladium (13.7 g) at room temperature and stirred at 95° C. for 10 hours. The reaction mixture was diluted with ethyl acetate (1.0 l), hydrochloric acid aqueous solution (1N, 0.70 l) and water (1.4 l), added active carbon (12 g) and stirred at room temperature for 2 hours. The mixture was filtrated and the organic layer was separated. The aqueous layer was extracted with ethyl acetate (1.0 l). The combined organic layer was washed with water (1.0 l) and brine (1.0 l), dried over magnesium sulfate and concentrated in vacuo. The residue was purified with silica gel column chromatography to give 2-(isopropylthio)-N-(methylsulfonyl)-4-(4,4,5,5-tetramethyl-1,3,2-dioxaborolan-2-yl)benzamide (57.4 g).

(+)ESI-MS (m/z): 422 (M+Na)$^+$

Preparation 63

The following compounds were obtained according to a similar manner to that of Preparation 62.
(1) Methyl 2-(isopropylthio)-4-(4,4,5,5-tetramethyl-1,3,2-dioxaborolan-2-yl)benzoate
   (+)ESI-MS (m/z): 359 (M+Na)$^+$
(2) 2-(Isopropylamino)-N-(methylsulfonyl)-4-(4,4,5,5-tetramethyl-1,3,2-dioxaborolan-2-yl)benzamide
   (−)ESI-MS (m/z): 299 (M-tetramethylethylene)$^−$
(3) 2-(Cyclohexylamino)-N-(methylsulfonyl)-4-(4,4,5,5-tetramethyl-1,3,2-dioxaborolan-2-yl)benzamide
   (−)ESI-MS (m/z): 421 (M−H)$^−$ Preparation 64

A mixture of 4-bromo-2-fluorobenzoic acid (1.0 g) and cyclohexylamine (10 ml) was stirred under reflux for 5 hours. The mixture was poured into ethyl acetate (50 ml) and water (50 ml), acidified with concentrated hydrochloric acid and extracted with ethyl acetate. The organic layer was washed with water and brine, dried over magnesium sulfate and concentrated in vacuo to give 4-bromo-2-(cyclohexylamino)benzoic acid (1.32 g).

(−)ESI-MS (m/z): 296, 298 (M−H)$^−$

Preparation 65

To a solution of tert-butyl [2-[3'-(isopropylamino)-4'-[[(methylsulfonyl)amino]carbonyl]-4-biphenylyl]ethyl]-carbamate (411 mg) in ethyl acetate (2 ml) was added hydrogen chloride ethyl acetate solution (4N, 2 ml) and stirred at room temperature overnight. The reaction mixture was evaporated and the residue was pulverized with diisopropyl ether. The resulting solid was collected by filtration and dried to give 4'-(2-aminoethyl)-3-(isopropylamino)-N-(methylsulfonyl)-4-biphenylcarboxamide dihydrochloride (281 mg).

(−)ESI-MS (m/z): 374 (M−H)$^−$

Preparation 66

To a solution of methyl 4'-(2-hydroxyethoxy)-3-(isopropylthio)-4-biphenylcarboxylate (124 mg) and tetrabromomethane (285 mg) in tetrahydrofuran (1.86 ml) was added triphenylphosphine (207 mg) and stirred at room temperature for 1 hour. The reaction mixture was concentrated in vacuo, and the residue was purified with silica gel column chromatography to give methyl 4'-(2-bromoethoxy)-3-(isopropylthio)-4-biphenylcarboxylate (142 mg).

(+)ESI-MS (m/z): 431, 433 (M+Na)$^+$

Preparation 67

To a solution of 3-(4-bromophenyl)propanoic acid (15.0 g) in thionyl chloride (24.5 g) was added catalytic amount of N,N-dimethylformamide (one drop) and refluxed for 1.5 hours under nitrogen atmosphere. After cooling to room temperature, the reaction mixture was poured slowly into 28% aqueous ammonium hydroxide solution (150 ml) at 0° C. The mixture was extracted with ethyl acetate, washed with water and brine and dried over magnesium sulfate. Filtration followed by evaporation under reduced pressure gave 3-(4-bromophenyl)propanamide (13.7 g) as a white solid.

NMR (DMSO-d$_6$, δ): 2.33 (2H, t, J=7.5 Hz), 2.77 (2H, t, J=7.8 Hz), 7.17 (2H, d, J=8.5 Hz), 7.45 (2H, d, J=8.5 Hz)
(−)ESI-MS (m/z): 226, 228 (M−H)$^−$

Preparation 68

To a solution of 3-(4-bromophenyl)propanamide (1.59 g) in tetrahydrofuran (24 ml) was added lithium aluminum hydride (370 mg) and the mixture was refluxed for 1.5 hours under nitrogen atmosphere. After cooling to room temperature, the reaction mixture was poured into 1N aqueous sodium hydroxide solution (100 ml). The mixture was extracted with ethyl acetate and the organic layer was washed with water and brine and dried over magnesium sulfate. Filtration followed by evaporation under reduced pressure gave 3-(4-bromophenyl)-1-propanamine (1.55 g) as a yellow oil.

(−)ESI-MS (m/z): 213 (M−H)−

Preparation 69

To a solution of (2R)-2-(4-nitrophenyl)oxirane (1.21 g) in dimethyl sulfoxide (1.11 ml) was added N,O-bis(trimethylsilyl)acetamide (1.12 ml) and the reaction mixture was stirred at room temperature for 1.5 hours. To the reaction mixture was added a solution of 3-(4-bromophenyl)-1-propanamine (1.55 g) in dimethyl sulfoxide (7 ml) and the reaction mixture was stirred at 90° C. for 16 hours. After cooling to room temperature, 5% aqueous acetic acid (60 ml) was added and the reaction mixture was stirred at room temperature for 1 hour. The pH was adjusted to 10 by using 1N aqueous sodium hydroxide solution. The mixture was extracted with ethyl acetate and the organic layer was washed with water and brine, and dried over magnesium sulfate. Filtration followed by evaporation under reduced pressure gave a crude product (3.61 g). To a solution of the product in tetrahydrofuran (35 ml) was added di-tert-butyl dicarbonate (1.56 g) and the mixture was stirred at room temperature for 7 hours. The mixture was partitioned between ethyl acetate and water and the organic layer was separated, washed with brine, and dried over magnesium sulfate. Filtration followed by evaporation under reduced pressure gave a crude product which was purified by column chromatography on silica gel (eluent: hexane/ethyl acetate=4/1) to give tert-butyl [3-(4-bromophenyl)propyl][(2R)-2-hydroxy-2-(4-nitrophenyl)ethyl]carbamate (663 mg) as an orange solid.

(+)ESI-MS (m/z): 501, 503 (M−Na)+

Preparation 70

To a suspension of (1R)-2-amino-1-(3-pyridyl)ethanol dihydrochloride (2.90 g), 3-(4-bromophenyl)propionic acid (3.30 g), 1-(3-dimethylaminopropyl)-3-ethylcarbodiimide hydrochloride (2.77 g) and 1-hydroxybenzotriazole hydrate (2.92 g) in N,N-dimethylformamide (30 ml) was added triethylamine (4.02 ml) at 4° C. The mixture was stirred at room temperature for 1.5 hours. The reaction mixture was poured into water (145 ml) and the pH was adjusted to 10 with 24% aqueous sodium hydroxide solution at 4° C. The mixture was stirred at room temperature for 30 minutes. The precipitate was collected by filtration, washed with water and dried at 50° C. to give 3-(4-bromophenyl)-N-[(2R)-2-hydroxy-2-(3-pyridyl)ethyl]propanamide (4.32 g) as a white solid. The filtrate was extracted with ethyl acetate, washed with water and brine and dried over magnesium sulfate. Filtration followed by evaporation under reduced pressure gave 3-(4-bromophenyl)-N-[(2R)-2-hydroxy-2-(3-pyridyl)ethyl]propanamide (0.43 g) as a white solid.

(+)ESI-MS (m/z): 349, 351 (M+H)+

Preparation 71

To a suspension of 3-(4-bromophenyl)-N-[(2R)-2-hydroxy-2-(3-pyridyl)ethyl]propanamide (3.42 g) in tetrahydrofuran (58 ml) was added 2.0M dimethyl sulfide—borane (1:1) in tetrahydrofuran (16.1 ml) dropwise at 0-5° C. over 45 minutes. After cooling to room temperature, to the reaction mixture were added methanol (2.99 ml) and 37% hydrochloric acid (4.8 ml) at 4° C. (ice bath). The mixture was stirred at 80° C. for 1 hour. After cooling to room temperature, the reaction mixture was concentrated under reduced pressure and to the residue was added water (100 ml). The pH was adjusted to 10 with 24% aqueous sodium hydroxide solution at 4° C. and the mixture was extracted with ethyl acetate (200 ml). The organic layer was washed with water and brine and dried over magnesium sulfate. Filtration followed by evaporation under reduced pressure gave (1R)-2-[[3-(4-bromophenyl)propyl]-amino]-1-(3-pyridyl)ethanol (3.22 g) as a yellow oil.

(+)ESI-MS (m/z): 335, 337 (M+H)+

Preparation 72

To a solution of (1R)-2-[[3-(4-bromophenyl)propyl]-amino]-1-(3-pyridyl)ethanol (3.22 g) in tetrahydrofuran (32 ml) was added di-tert-butyl dicarbonate (2.14 g) and the mixture was stirred at room temperature for 2 hours. The reaction mixture was concentrated under-reduced pressure and the residue was extracted with ethyl acetate. The organic layer was washed with water and brine and dried over magnesium sulfate. Filtration and evaporation under reduced pressure gave a crude product (3.25 g) which was purified by column chromatography on silica gel (eluent: hexane/ethyl acetate=1.5/1 to 2/1) to give tert-butyl [3-(4-bromophenyl)propyl][(2R)-2-hydroxy-2-(3-pyridyl)ethyl]-carbamate (3.25 g) as a pale yellow oil.

(+)ESI-MS (m/z): 435, 437 (M+H)+, 457, 459 (M+Na)+

Preparation 73

To a suspension of sodium hydride (60% w/w, 20.5 g) in N,N-dimethylformamide (365 ml) was added 2-methyl-1-propanol (48.7 ml) dropwise below 30° C. over 2 hours under nitrogen atmosphere. To the mixture was added 4-bromo-2-fluorobenzoic acid (50.0 g) slowly below 35° C. To the reaction mixture was added N,N-dimethylformamide (600 ml) and the mixture was stirred at room temperature for 4 days. The reaction mixture was partitioned between water (2000 ml) and hexane (1000 ml). The water layer was separated and acidified with 37% hydrochloric acid. The precipitate was collected by filtration, washed with water and dried at 55° C. to give 4-bromo-2-isobutoxybenzoic acid (62.4 g) as a white solid.

(−)ESI-MS (m/z): 271, 273 (M−H)−

Preparation 74

To a solution of 4-bromo-2-isobutoxybenzoic acid (14.0 g) in N,N-dimethylformamide (70 ml) were added dipotassium carbonate (14.2 g) and iodomethane (4.79 ml). The mixture was stirred at room temperature for 1 hour. The reaction mixture was filtered and the filtrate was extracted with ethyl acetate-hexane (1/1, 600 ml) and washed with water (500 ml). The water layer was extracted with ethyl acetate-hexane (1/1, 200 ml) and the extract was washed with water (200 ml). The combined organic layer was washed with brine and dried over magnesium sulfate. Filtration followed by evaporation under reduced pressure gave methyl 4-bromo-2-isobutoxybenzoate (12.0 g) as a pale yellow oil.

(+)ESI-MS (m/z): 309, 311 (M−Na)+

Preparation 75

A mixture of methyl 4-bromo-2-isobutoxybenzoate (12.0 g), bis(pinacolato)diboron (12.2 g), dichloropalladium-triphenylphosphine (1:2, 2.05 g) and potassium acetate (12.3 g) in 1,4-dioxane (120 ml) was stirred at 90° C. for 1.5 hours. After cooling to room temperature, the reaction mixture was poured into ethyl acetate (500 ml) and water (500 ml) and the mixture was filtered through a Celite cake. The organic layer was separated and washed with water (500 ml) and brine (500 ml). The separated organic layer was concentrated under reduced pressure to ca. 150 ml. To the solution were added water (150 ml), acetic acid ammoniate (14.4 g) and sodium periodate (31.2 g) and the reaction mixture was stirred at room temperature for 3.5 hours. The reaction mixture was filtered and washed with ethyl acetate. The filtrate was extracted with ethyl acetate (twice) and the combined organic layer was washed with water and brine and dried over magnesium sulfate. Filtration followed by evaporation under reduced pressure gave a crude product followed by purification by column chromatography on silica gel (eluent: chloroform/methanol=98/2) to give [3-isobutoxy-4-(methoxycarbonyl)phenyl]boronic acid (7.58 g) as a purple solid.

(−)ESI-MS (m/z): 251 (M−H)−

Preparation 76

To a solution of 2-(4-bromophenyl)ethanol (1.00 g) and tetrabromomethane (3.96 g) in tetrahydrofuran (10 ml) was added triphenylphosphine (2.87 g) at room temperature and the mixture was stirred at the same temperature for 1 hour under nitrogen. The mixture was evaporated under reduced pressure. The residue was purified by silica gel column chromatography to give 1-bromo-4-(2-bromoethyl)benzene (2.07 g).

NMR (CDCl$_3$, δ): 3.12 (2H, t, J=7.4 Hz), 3.54 (2H, t, J=7.4 Hz), 7.09 (2H, d, J=10.6 Hz), 7.45 (2H, d, J=10.6 Hz)

Preparation 77

The following compound was obtained according to a similar manner to that of Example 77.

4'-(2-Bromoethyl)-3-isopropoxy-N-(methylsulfonyl)-4-biphenylcarboxamide (−)ESI-MS (m/z): 439 (M−H)−

Preparation 78

To a suspension of lithium aluminum hydride (2.54 g) in tetrahydrofuran (50 ml) was added dropwise a solution of 4-bromo-2-(cyclohexyloxy)benzoic acid (10 g) in tetrahydrofuran (50 ml) at 5° C. under nitrogen, and the mixture was stirred at room temperature for 2.5 hours. The resulting mixture was poured into 1N hydrochloric acid and the aqueous layer was extracted with ethyl acetate. The organic layer was washed successively with 1N hydrochloric acid, aqueous-sodium bicarbonate and brine, dried over anhydrous magnesium sulfate and evaporated under reduced pressure. The residue was purified by column chromatography on silica gel (hexane/ethyl acetate=10:1 to 5:1) to give (4-bromo-2-cyclohexyloxyphenyl)methanol (5.47 g).

(+)ESI-MS (m/z): 307, 309 (M+Na)+

Preparation 79

To a solution of (4-bromo-2-cyclohexyloxyphenyl)methanol (5.46 g) in dichloromethane (16 ml) was added thionyl chloride (3.42 g) dropwise at 5° C. under nitrogen, and the mixture was stirred at the same temperature for 1.5 hours. The resulting mixture was poured into water and the aqueous layer was extracted with ethyl acetate. The organic layer was washed successively with saturated aqueous sodium bicarbonate and brine, dried over anhydrous magnesium sulfate and evaporated and dried in vacuo to give 4-bromo-1-chloromethyl-2-cyclohexyloxybenzene (5.59 g).

(+)ESI-MS (m/z): 321, 323 (M+Na)+

Preparation 80

To a solution of 4-bromo-1-chloromethyl-2-cyclohexyloxybenzene (5.58 g) in ethanol (55.8 ml) were added potassium iodide (3.36 g) and potassium cyanide (1.56 g) at room temperature under nitrogen, and the mixture was stirred at 70° C. for 80 minutes. The resulting mixture was poured into water and the aqueous layer was extracted with toluene. The organic layer was washed successively with water and brine, dried over anhydrous magnesium sulfate and evaporated under reduced pressure. The residue was purified by column chromatography on silica gel (hexane/toluene=2:1 to 1:1) to give (4-bromo-2-cyclohexyloxyphenyl)acetonitrile (1.51 g).

(+)ESI-MS (m/z): 316, 318 (M+Na)+

Preparation 81

A mixture of (4-bromo-2-cyclohexyloxyphenyl)acetonitrile (1.45 g) and potassium hydroxide (829 mg) in ethanol (17.4 ml) and water (5 ml) was refluxed for 22 hours. Ethanol was removed by evaporation under reduced pressure. To the residue were added water and a mixture of hexane and ethyl acetate (1:1). After separation, the aqueous layer was adjusted below pH 3 with concentrated hydrochloric acid, and extracted with ethyl acetate. The organic layer was dried over anhydrous magnesium sulfate, evaporated and dried in vacuo to give (4-bromo-2-cyclohexyloxyphenyl)acetic acid (1.34 g).

(−)ESI-MS (m/z): 311, 313 (M−H)−

Preparation 82

To a solution of (4-bromo-2-cyclohexyloxyphenyl)acetic acid (1.33 g) in N,N-dimethylformamide (13 ml) were added potassium carbonate (0.88 g) and iodoethane (1.33 g) at room temperature under nitrogen, and the mixture was stirred at the same temperature for 2.5 days. The resulting mixture was poured into water and the aqueous layer was extracted with a mixture of hexane and ethyl acetate (1:1). The organic layer was washed successively with water (twice) and brine, dried over anhydrous magnesium sulfate and evaporated under reduced pressure. The residue was purified by column chromatography on silica gel (hexane/toluene=1:1 to 1:2) to give ethyl (4-bromo-2-cyclohexyloxyphenyl)acetate (1.24 g).

(+)ESI-MS (m/z): 363, 365 (M+Na)+

Preparation 83

To a solution of ethyl (4-bromo-2-cyclohexyloxyphenyl)acetate (1.23 g) in 1,4-dioxane (14.6 ml) were added 4,4,4',4',5,5,5',5'-octamethyl-2,2'-bi-1,3,2-dioxaborolane (1.01 g), dichlorobis(triphenyphosphine)palladium(II) (126 mg) and potassium acetate (1.06 g) at room temperature under nitrogen, and the mixture was stirred at 95° C. for 2 hours. The resulting mixture was poured into 1N hydrochloric acid and the aqueous layer was extracted with a mixture of hexane and ethyl acetate (1:1). The organic layer was washed successively with water and brine, dried over anhydrous magnesium sulfate, evaporated and dried in vacuo. To a suspension of the above obtained residue in a mixture of ethyl acetate (14.6 ml) and water (24.6 ml) were added ammonium acetate (1.75 g) and sodium periodate (4.86 g) at room temperature, and the mixture was stirred at the same temperature for 24 hours. The resulting mixture was poured into dilute hydrochloric acid and the aqueous layer was extracted with ethyl acetate. The organic layer was washed successively with water and brine, dried over anhydrous magnesium sulfate and evaporated under reduced pressure. The residue was purified by column chromatography on silica gel (hexane/ethyl acetate=2:1 to 1:1) to give [3-cyclohexyloxy-4-(ethoxycarbonylmethyl)phenyl]boronic acid (719 mg).

(−)ESI-MS (m/z): 305 (M−H)−

EXAMPLE 24

The following compounds were obtained according to a similar manner to that of Example 18.

(1) N-(Benzylsulfonyl)-4'-[2-[[(2R)-2-hydroxy-2-phenylethyl]amino]ethyl]-3-isopropoxy-4-biphenylcarboxamide hydrochloride NMR (DMSO-$d_6$, δ): 1.24 (6H, d, J=6.0 Hz), 3.02-3.28 (6H, m), 4.86 (2H, s), 4.89-5.05 (2H, m), 6.23 (1H, d, J=3.8 Hz), 7.31-7.45 (14H, m), 7.67-7.77 (3H, m) (+)ESI-MS (m/z): 573 (M+H)$^+$ (2) 4'-[2-[[(2R)-2-Hydroxy-2-phenylethyl]amino]ethyl]-3-isopropoxy-N-(isopropylsulfonyl)-4-biphenylcarboxamide hydrochloride NMR (DMSO-$d_6$, δ): 1.28 (6H, d, J=5.4 Hz), 1.35 (6H, d, J=6.0 Hz), 3.98-3.26 (6H, m), 4.86-5.04 (3H, m), 6.22 (1H, d, J=3.6 Hz), 7.25-7.46 (9H, m), 7.61-7.77 (3H, m) (+)ESI-MS (m/z): 525 (M+H)$^+$ (3) 4'-[2-[[(2R)-2-Hydroxy-2-phenylethyl]amino]ethyl]-3-methoxy-N-(methylsulfonyl)-4-biphenylcarboxamide hydrochloride NMR (DMSO-$d_6$, δ): 2.99-3.27 (6H, m), 3.36 (3H, s), 3.98 (3H, s), 4.95-5.06 (1H, m), 6.23 (1H, d, J=4.0 Hz), 7.29-7.44 (9H, m), 7.65-7.8 (3H, m) (+)ESI-MS (m/z): 469 (M+H)$^+$ (4) 4'-[2-[[(2R)-2-Hydroxy-2-phenylethyl]amino]ethyl]-3-isopropoxy-N-(propylsulfonyl)-4-biphenylcarboxamide hydrochloride NMR (DMSO-$d_6$, δ): 1.02 (3H, t, J=3.7 Hz), 1.36 (6H, d, J=2.8 Hz), 1.79-1.82 (2H, m), 3.01-3.11 (3H, m), 3.17-3.26 (3H, m), 3.49 (2H, t, J=3.8 Hz), 4.94-5.02 (2H, m), 6.23 (1H, d, J=1.8 Hz), 7.31-7.43 (9H, m), 7.69 (1H, d, J=4.0 Hz), 7.73 (2H, d, J=4.0 Hz) (+)ESI-MS (m/z): 525 (M+H)$^+$ (5) 4'-[2-[[(2R)-2-Hydroxy-2-phenylethyl]amino]ethyl]-3-isopropoxy-N-(phenylsulfonyl)-4-biphenylcarboxamide hydrochloride NMR (DMSO-$d_6$, δ): 1.30 (6H, d, J=6.0 Hz), 2.99-3.28 (6H, m), 4.82-4.94 (1H, m), 4.94-5.05 (1H, m), 6.22 (1H, d, J=4.0 Hz), 7.27-7.41 (10H, m), 7.63-7.76 (5H, m), 8.00-8.06 (2H, m) (+)ESI-MS (m/z): 559 (M+H)$^+$ (6) N-(Benzylsulfonyl)-3-(cyclohexyloxy)-4'-[2-[[(2R)-2-hydroxy-2-phenylethyl]amino]ethyl]-4-biphenylcarboxamide hydrochloride NMR (DMSO-$d_6$, δ): 1.14-1.69 (8H, m), 1.74-1.92 (2H, m), 2.97-3.29 (6H, m), 4.68-4.81 (1H, m), 4.87 (2H, s), 4.95-5.06 (1H, m), 6.23 (1H, d, J=3.8 Hz), 7.28-7.46 (14H, m), 7.67-7.81 (3H, m) (+)ESI-MS (m/z): 613 (M+H)$^+$ (7) 4'-[3-[[(2R)-2-(4-Aminophenyl)-2-hydroxyethyl]amino]-propyl]-3-(cyclohexyloxy)-N-(methylsulfonyl)-4-biphenylcarboxamide dihydrochloride NMR (DMSO-$d_6$, δ): 1.27-1.83 (8H, m), 1.86-2.16 (4H, m), 2.63-2.81 (2H, m), 2.63-2.81 (2H, m), 2.86-3.19 (4H, m), 3.38 (3H, s), 4.73-4.89 (1H, m), 4.93-5.07 (1H, m), 7.19-7.53 (8H, m), 7.61-7.86 (3H, m) (−)ESI-MS (m/z): 564 (M−H)$^−$ (8) 4'-[3-[[(2R)-2-(4-Aminophenyl)-2-hydroxyethyl]amino]-propyl]-3-isopropoxy-N-(methylsulfonyl)-4-biphenylcarboxamide dihydrochloride NMR (DMSO-$d_6$, δ): 1.38 (6H, d, J=3.0 Hz), 1.89-2.14 (2H, m), 2.63-2.81 (2H, m), 2.87-3.22 (4H, m), 3.38 (3H, s), 4.90-5.06 (2H, m), 7.23-7.50 (8H, m), 7.67-7.82 (3H, m), (−)ESI-MS (m/z): 524 (M−H)$^−$ (9) 4'-[3-[[(2R)-2-(4-Aminophenyl)-2-hydroxyethyl]amino]-propyl]-3-isobutyl-N-(methylsulfonyl)-4-biphenylcarboxamide dihydrochloride NMR (DMSO-$d_6$, δ): 0.87 (6H, d, J=6.6 Hz), 1.79-1.9 (1H, m), 1.91-2.07 (2H, m), 2.65-2.77 (4H, m), 2.91-3.13 (4H, m), 3.38 (3H, s), 4.72-4.82 (1H, m), 6.69-6.92 (2H, m), 7.1-7.26 (2H, m), 7.35 (2H, d, J=8.4 Hz), 7.52-7.61 (3H, m), 7.67 (2H, d, J=8.4 Hz) (−)ESI-MS (m/z): 523 (M−H)$^−$

(10) 4'-[3-[[(2R)-2-(4-Aminophenyl)-2-hydroxyethyl]amino]-propyl]-3-cyclopentyl-N-(methylsulfonyl)-4-biphenylcarboxamide dihydrochloride NMR (DMSO-$d_6$, δ): 1.58-1.73 (4H, m), 1.75-1.88 (2H, m), 1.91-2.12 (4H, m), 2.64-2.76 (2H, m), 2.89-3.13 (5H, m), 3.38 (3H, s), 4.69-4.81 (1H, m), 6.66-6.89 (2H, m), 7.07-7.25 (2H, m), 7.3-7.71 (7H, m) (−)ESI-MS (m/z): 534 (M−H)$^−$

(11) (3-(Cyclohexyloxy)-4'-[2-[[(2R)-2-hydroxy-2-phenylethyl]amino]ethyl]-4-biphenylyl]acetic acid hydrochloride NMR (DMSO-$d_6$, δ): 1.25-1.95 (10H, m), 2.9-3.45 (6H, m), 3.52 (2H, s), 4.45-4.65 (1H, m), 4.9-5.05 (1H, m), 7.05-7.5 (10H, m), 7.63 (2H, d, J=8.2 Hz) (+)ESI-MS (m/z): 474 (M-HCl+H)$^+$

(12) (3-(Cyclohexyloxy)-4'-[2-[[(2R)-2-hydroxy-2-(3-pyridyl)ethyl]amino]ethyl]-4-biphenylyl]acetic acid dihydrochloride NMR (DMSO-$d_6$, δ): 1.2-1.95 (10H, m), 2.95-3.6 (6H, m), 3.52 (2H, s), 4.45-4.65 (1H, m), 5.15-5.3 (1H, m), 7.1-7.3 (3H, m), 7.35 (2H, d, J=8.1 Hz), 7.64 (2H, d, J=8.1 Hz), 7.8-7.95 (1H, m), 8.25-8.4 (1H, m), 8.75-8.9 (2H, m) (+)ESI-MS (m/z): 475 (M−2HCl+H)$^+$

(13) 2-[3-(Cyclohexyloxy)-4'-[2-[[(2R)-2-hydroxy-2-phenylethyl]amino]ethyl]-4-biphenylyl]-N-(methylsulfonyl)acetamide hydrochloride NMR (DMSO-$d_6$, δ): 1.2-1.95 (10H, m), 2.95-3.45 (9H, m), 3.60 (2H, s), 4.45-4.65 (2H, m), 4.85-5.0 (1H, m), 7.1-7.5 (10H, m), 7.64 (2H, d, J=8.1 Hz) (−)ESI-MS (m/z): 549 (M-HCl—H)$^−$

(14) 2-[3-(Cyclohexyloxy)-4'-[2-[[(2R)-2-hydroxy-2-(3-pyridyl)ethyl]amino]ethyl]-4-biphenylyl]-N-(methylsulfonyl)acetamide dihydrochloride NMR (DMSO-$d_6$, δ): 1.1-1.9 (10H, m), 2.95-3.6 (9H, m), 3.61 (2H, s), 4.5-4.65 (1H, m), 5.15-5.3 (1H, m), 7.05-7.3 (3H, m), 7.35 (2H, d, J=8.1 Hz), 7.64 (2H, d, J=8.1 Hz), 7.75-7.9 (1H, m), 8.25-8.35 (1H, m), 7.75-7.9 (2H, m) (+)ESI-MS (m/z): 552 (M−2HCl+H)$^+$

(15) 4'-[2-[[(2R)-2-Hydroxy-2-(3-pyridyl)ethyl]amino]ethyl]-3-(isopropylamino)-N-(methylsulfonyl)-4-biphenylcarboxamide trihydrochloride NMR (DMSO-$d_6$, δ): 1.24 (6H, d, J=3.1 Hz), 3.05-3.11 (2H, m), 3.19-3.32 (3H, m), 3.36-3.45 (1H, m), 3.37 (3H, s), 3.89-3.95 (1H, m), 5.35 (1H, d, J=2.9 Hz), 6.86 (1H, d, J=4.2 Hz), 6.97 (1H, s), 7.38 (2H, d, J=4.0 Hz), 7.70 (2H, d, J=4.2 Hz), 7.83 (1H, d, J=4.2 Hz), 8.08 (1H, dd, J=2.7, 4 Hz), 8.6 (1H, d, J=4 Hz), 8.89 (3H, d, J=2.7 Hz), 8.95 (1H, s), 9.34 (1H, br s), 9.44 (1H, br s) (−)ESI-MS (m/z): 495 (M−H)$^−$

(16) 4'-[2-[[(2R)-2-Hydroxy-2-phenylethyl]amino]ethyl]-N-(methylsulfonyl)-3-(propylamino)-4-biphenylcarboxamide dihydrochloride NMR (DMSO-$d_6$, δ): 1.02 (3H, t, J=6.5 Hz), 1.51-1.71 (2H, m), 3.02-3.32 (8H, m), 3.37 (3H, s), 5.00 (1H, d, J=7.5 Hz), 6.87 (1H, d, J=8.0 Hz), 6.94 (1H, s), 7.32-7.42 (7H, m), 7.71 (2H, d, J=8.0 Hz), 7.82 (1H, d, J=8.5 Hz), 8.91 (1H, br s), 9.26 (1H, br s) (−)ESI-MS (m/z): 494 (M−H)$^−$

(17) 3-[(2-Ethoxyethyl)amino]-4'-[2-[[(2R)-2-hydroxy-2-phenylethyl]amino]ethyl]-N-(methylsulfonyl)-4-biphenylcarboxamide dihydrochloride NMR (DMSO-$d_6$, δ): 1.15 (3H, t, J=7.0 Hz), 2.98-3.34 (6H, m), 3.32 (3H, s), 3.42-3.52 (4H, m), 3.63 (2H, t, J=5.3 Hz), 4.99 (1H, d, J=7.0 Hz), 6.88 (1H, d, J=8.5 Hz), 6.99 (1H, s), 7.32-7.42 (7H, m), 7.72 (2H, d, 8.0 Hz), 7.81 (1H, d, J=8.5 Hz), 8.89 (1H, br s), 9.24 (1H, br s) (−)ESI-MS (m/z): 524 (M−H)$^−$

(18) 4'-[2-[[(1S,2R)-2-Hydroxy-1-methyl-2-phenylethyl]amino]ethyl]-3-(isopropylamino)-N-(methylsulfonyl)-4-biphenylcarboxamide dihydrochloride NMR (DMSO-$d_6$, δ): 0.97 (3H, d, J=6.5 Hz), 1.24 (6H, d, J=6.0 Hz), 3.03-3.57 (5H, m), 3.38 (3H, s), 3.86-3.98 (1H, m), 5.22, (1H, d, J=1.5 Hz), 6.86 (1H, d, J=8.5 Hz), 6.96 (1H, s), 7.23-7.49 (7H, m), 7.72 (2H, d, J=8.0 Hz), 7.83 (1H, d, J=8.5 Hz), 9.00 (2H, br s) (−)ESI-MS (m/z): 508 (M−H)⁻

(19) 4'-[2-[[(2R)-2-Hydroxy-2-phenylethyl]amino]ethoxy]-3-(isopropylamino)-N-(methylsulfonyl)-4-biphenylcarboxamide dihydrochloride NMR (DMSO-$d_6$, δ): 1.24 (6H, d, J=6.5 Hz), 3.01-3.49 (4H, m), 3.37 (3H, s), 3.84-4.00 (1H, m), 4.32-4.44 (2H, m), 5.05 (1H, d, J=10 Hz), 6.85 (1H, d, J=8.5 Hz), 6.95 (1H, s), 7.10 (2H, d, J=9.0 Hz), 7.28-7.47 (5H, m), 7.60 (2H, d, J=9.0 Hz), 7.81 (1H, d, J=8.5 Hz), 9.04 (1H, br s), 9.32 (1H, br s) (−)ESI-MS (m/z): 510 (M−H)⁻

(20) 3-(Cyclohexylamino)-4'-[2-[[(2R)-2-hydroxy-2-phenylethyl]amino]ethoxy]-N-(methylsulfonyl)-4-biphenylcarboxamide dihydrochloride NMR (DMSO-$d_6$, δ): 1.14-1.80 (8H, m), 1.90-2.05 (2H, m), 3.00-3.54 (4H, m), 3.37 (3H, s), 4.35-4.45 (2H, m), 5.04 (1H, d, J=9.5 Hz), 6.83 (1H, d, J=7 Hz), 6.96 (1H, s), 7.10 (2H, d, J=8.5 Hz), 7.31-7.42 (5H, m), 7.70 (2H, d, J=9 Hz), 7.81 (1H, d, J=8 Hz), 9.03 (1H, br s), 9.34 (1H, br s) (+)ESI-MS (m/z): 550 (M+H)⁺

(21) 4'-(2-[[(2R)-2-Hydroxy-2-phenylethyl]amino]ethoxy]-N-(methylsulfonyl)-3-(propylamino)-4-biphenylcarboxamide dihydrochloride NMR (DMSO-$d_6$, δ): 0.99 (3H, t, J=7.5 Hz), 1.50-1.75 (2H, m), 3.05-3.57 (6H, m), 3.37 (3H, s), 4.34-4.47 (2H, m), 5.03 (1H, d, J=7.5 Hz), 6.85 (1H, d, J=8.5 Hz), 6.92 (1H, s), 7.10 (2H, d, J=8.5 Hz), 7.31-7.48 (5H, m), 7.73 (2H, d, J=8.5 Hz) 7.80 (1H, d, J=8.5 Hz), 9.01 (1H, br s), 9.26 (1H, br s), 9.83 (2H, br s) (−)ESI-MS (m/z): 510 (M−H)⁻

(22) 3-[(2-Ethoxyethyl)amino]-4'-[2-[[(2R)-2-hydroxy-2-phenylethyl]amino]ethoxy]-N-(methylsulfonyl)-4-biphenylcarboxamide dihydrochloride NMR (DMSO-$d_6$, δ): 1.15 (3H, t, J=7.0 Hz), 3.30-3.35 (4H, m), 3.37 (3H, s), 3.38-3.66 (6H, m), 4.32-4.45 (2H, m), 5.03 (1H, d, J=10 Hz), 6.87 (1H, d, J=8.5 Hz), 6.97 (1H, s), 7.09 (2H, d, J=9.0 Hz), 7.22-7.47 (5H, m), 7.73 (2H, d, J=8.5 Hz), 7.79 (1H, d, J=8.5 Hz), 9.03 (1H, br s), 9.32 (1H, br s) (−)ESI-MS (m/z): 540 (M−H)⁻

(23) 4'-[(2S)-3-Hydroxy-2-[[(2R)-2-hydroxy-2-phenylethyl]-amino]propyl]-3-(isopropylthio)-N-(methylsulfonyl)-4-biphenylcarboxamide hydrochloride NMR (DMSO-$d_6$, δ): 1.26 (6H, d, J=6.5 Hz), 2.88-3.69 (8H, m), 3.38 (3H, s), 5.01-5.18 (1H, m), 5.45 (1H, br s), 6.23 (1H, d, J=3.5 Hz), 7.32-7.48 (7H, m), 7.61 (2H, s), 7.71-7.75 (3H, m), 8.52 (1H, br s), 9.25 (1H, br s) (−)ESI-MS (m/z): 541 (M−H)⁻

(24) 4'-[2-[[(2R)-2-(4-Aminophenyl)-2-hydroxyethyl]amino]-ethyl]-3-(isopropylthio)-N-(methylsulfonyl)-4-biphenylcarboxamide dihydrochloride NMR (DMSO-$d_6$, δ): 1.26 (6H, d, J=7.2 Hz), 2.89-3.37 (6H, m), 3.38 (3H, s), 3.58-3.72 (1H, m), 4.98 (1H, d, J=9.5 Hz), 6.61 (1H, d, J=8.0 Hz), 7.03-7.12 (1H, m), 7.15-7.30 (2H, m), 7.32-7.51 (3H, m), 7.61 (2H, s), 7.66-7.79 (3H, m), 8.88 (1H, br s), 9.17 (1H, br s) (−)ESI-MS (m/z): 526 (M−H)⁻

(25) 4'-[2-[[(2R)-2-Hydroxy-2-(3-pyridyl)ethyl]amino]ethyl]-3-(isopropylthio)-4-biphenylcarboxylic acid dihydrochloride NMR (DMSO-$d_6$, δ): 1.31 (6H, d, J=6.5 Hz), 3.04-3.48 (6H, m), 3.69-3.83 (1H, m), 5.30 (1H, d, J=5.5 Hz), 7.41 (2H, d, J=8.0 Hz), 7.49 (1H, dd, J=1.5, 8.0 Hz), 7.60 (1H, s), 7.72 (2H, d, J=8.0 Hz), 7.90 (1H, d, J=8.0 Hz), 7.97 (1H, dd, J=5.5, 8.0 Hz), 8.48 (1H, d, J=8.0 Hz), 8.83 (1H, d, J=5.5 Hz), 8.90 (1H, d, J=1.5 Hz), 9.29 (1H, br s), 9.38 (1H, br s) (−)ESI-MS (m/z): 435 (M−H)⁻

EXAMPLE 25

The following compounds were obtained according to a similar manner to that of Example 12.

(1) tert-Butyl [(2R)-2-hydroxy-2-phenylethyl][2-[3'-isopropoxy-4'-[[(isopropylsulfonyl)amino]carbonyl]-4-biphenylyl]ethyl]carbamate (−)ESI-MS (m/z): 623 (M−H)⁻

(2) tert-Butyl [2-[4'-[[(benzylsulfonyl)amino]carbonyl]-3'-isopropoxy-4-biphenylyl]ethyl][(2R)-2-hydroxy-2-phenylethyl]carbamate (+)ESI-MS (m/z): 695 (M+Na)⁺

EXAMPLE 26

To a solution of 4'-[2-[(tert-butoxycarbonyl)[(2R)-2-phenyl-2-(tetrahydro-2H-pyran-2-yloxy)ethyl]amino]ethyl]-3-(cyclohexyloxy)-4-biphenylcarboxylic acid (210 mg) in N,N-dimethylformamide (3 ml) were added methanesulfonamide (34.1 mg), N,N-dimethylaminopyridine (59.8 mg) and 1-(3-dimethylaminopropyl)-3-ethylcarbodiimide hydrochloride (125 mg) at room temperature and the mixture was stirred at the same temperature for 96 hours. The mixture was poured into aqueous hydrochloric acid solution (0.1N) and extracted with ethyl acetate. The organic layer was washed with brine, dried over sodium sulfate and evaporated under reduced pressure to give an acylsulfonamide product. To a solution of the product in methanol (6 ml) was added 4-methylbenzenesulfonic acid (7.4 mg) at room temperature and the mixture was stirred at the same temperature for 18 hours. The mixture was diluted with ethyl acetate and water. The organic layer was separated, washed with aqueous sodium bicarbonate solution and brine, dried over sodium sulfate and evaporated under reduced pressure. The residue was purified by column chromatography on silica gel (hexane/ethyl acetate=6/4) to give tert-butyl [2-[3'-(cyclohexyloxy)-4'-[[(methylsulfonyl)amino]carbonyl]-4-biphenylyl]ethyl][(2R)-2-hydroxy-2-phenylethyl]carbamate (99 mg).

(+)ESI-MS (m/z): 659 (M+Na)⁺

EXAMPLE 27

The following compounds were obtained according to a similar manner to that of Example 26.

(1) tert-Butyl [(2R)-2-hydroxy-2-phenylethyl][2-[3'-isobutoxy-4'-[[(methylsulfonyl)amino]carbonyl]-4-biphenylyl]ethyl]carbamate (+)ESI-MS (m/z): 633 (M+Na)⁺

(2) tert-Butyl [(2R)-2-hydroxy-2-phenylethyl][2-(3'-methoxy-4'-[[(methylsulfonyl)amino]carbonyl]-4-biphenyl)ethyl]carbamate (+)ESI-MS (m/z): 591 (M+Na)⁺

(3) tert-Butyl [(2R)-2-hydroxy-2-phenylethyl][2-[3'-isopropoxy-4'-[[(propylsulfonyl)amino]carbonyl]-4-biphenylyl]ethyl]carbamate (+)ESI-MS (m/z): 647 (M+Na)⁺

(4) tert-Butyl [(2R)-2-hydroxy-2-phenylethyl][2-[3'-isopropoxy-4'-[[(phenylsulfonyl)amino]carbonyl]-4-biphenylyl]ethyl]carbamate (+)ESI-MS (m/z): 681 (M+Na)⁺

(5) tert-Butyl [2-[4'-[[(benzylsulfonyl)amino]carbonyl]-3'-(cyclohexyloxy)-4-biphenylyl]ethyl][(2R)-2-hydroxy-2-phenylethyl]carbamate (+)ESI-MS (m/z): 735 (M+Na)⁺

EXAMPLE 28

The following compounds were obtained according to a similar manner to that of Example 43.

(1) tert-Butyl [2-[4'-[(acetylamino)sulfonyl]-3'-(cyclohexyloxy)-4-biphenylyl]ethyl][(2R)-2-hydroxy-2-phenylethyl]carbamate (+)ESI-MS (m/z): 659 (M+Na)$^+$ (2) tert-Butyl [(2R)-2-hydroxy-2-phenylethyl][2-[4'-[[(isobutylsulfonyl)amino]carbonyl]-3'-isopropoxy-4-biphenylyl]ethyl]carbamate (+)ESI-MS (m/z): 661 (M+Na)$^+$ (3) tert-Butyl [(2R)-2-hydroxy-2-phenylethyl][2-[3'-isopropoxy-4'-[[[(3-methylbutyl)sulfonyl]amino]-carbonyl]-4-biphenylyl]ethyl]carbamate (+)ESI-MS (m/z): 675 (M+Na)$^+$ (4) tert-Butyl [2-[4'-[[[(cyclohexylmethyl)sulfonyl]amino]-carbonyl]-3'-isopropoxy-4-biphenylyl]ethyl][(2R)-2-hydroxy-2-phenylethyl]carbamate (+)ESI-MS (m/z): 701 (M+Na)$^+$

EXAMPLE 29

The following compounds were obtained according to a similar manner to that of Example 6.

(1) N-[[3-(Cyclohexyloxy)-4'-(2-[[(2R)-2-hydroxy-2-phenylethyl]amino]ethyl]-4-biphenylyl]sulfonyl]-acetamide hydrochloride NMR (DMSO-d$_6$, δ): 1.74-1.99 (10H, m), 1.94 (3H, s), 2.99-3.28 (6H, m), 4.75-4.86 (1H, m), 4.9-5.0 (1H, m), 6.22 (1H, d, J=3.5 Hz), 7.30-7.43 (9H, m), 7.71-7.75 (2H, m), 7.87 (1H, d, J=8.0 Hz), 8.87 (2H, br s), 11.83 (1H, s) (+)ESI-MS (m/z): 537 (M+H)$^+$ (2) N-[[3-(Cyclohexyloxy)-4'-[2-[[(2R)-2-hydroxy-2-phenylethyl]amino]ethyl]-4-biphenylyl]sulfonyl]-butanamide hydrochloride NMR (DMSO-d$_6$, δ): 0.79 (3H, t, J=7.3 Hz), 1.26-1.98 (12H, m), 2.21 (2H, t, J=7.3 Hz), 2.99-3.34 (6H, m), 4.74-4.85 (1H, m), 4.95-5.04 (1H, m), 6.23 (1H, d, J=3.5 Hz), 7.30-7.43 (9H, m), 7.69-7.77 (2H, m), 7.88 (1H, d, J=8.5 Hz), 8.95 (1H, br s), 9.19 (1H, br s), 11.77 (1H, br s) (-)ESI-MS (m/z): 563 (M-H)$^-$ (3) 4'-[2-[[(2R)-2-Hydroxy-2-phenylethyl]amino]ethyl]-N-(isobutylsulfonyl)-3-isopropoxy-4-biphenylcarboxamide hydrochloride NMR (DMSO-d$_6$, δ): 1.06 (6H, d, J=7.0 Hz), 1.36 (6H, d, J=6.0 Hz), 2.10-2.30 (1H, m), 2.99-3.27 (6H, m), 3.44 (2H, d, J=6.6 Hz), 4.92-5.05 (2H, m), 6.24 (1H, d, J=4.0 Hz), 7.32-7.43 (9H, m), 7.68-7.76 (3H, m) (+)ESI-MS (m/z): 539 (M+H)$^+$ (4) 4'-[2-[[(2R)-2-Hydroxy-2-phenylethyl]amino]ethyl]-3-isopropoxy-N-[(3-methylbutyl)sulfonyl]-4-biphenylcarboxamide hydrochloride NMR (DMSO-d$_6$, δ): 0.90 (6H, d, J=6.0 Hz), 1.36 (6H, d, J=6.0 Hz), 1.55-1.78 (3H, m), 2.90-3.27 (6H, m), 3.48-3.55 (2H, m), 4.91-5.05 (2H, m), 6.23 (1H, d, J=3.5 Hz), 7.32-7.43 (9H, m), 7.66-7.75 (3H, m) (+)ESI-MS (m/z): 553 (M+H)$^+$ (5) N-[(Cyclohexylmethyl)sulfonyl]-4'-[2-[[(2R)-2-hydroxy-2-phenylethyl]amino]ethyl]-3-isopropoxy-4-biphenylcarboxamide hydrochloride NMR (DMSO-d$_6$, δ): 1.09-1.31 (5H, m), 1.36 (6H, d, J=6.0 Hz), 1.53-1.73 (3H, m), 1.80-1.97 (3H, m), 3.02-3.27 (6H, m), 3.45 (2H, d, J=6.0 Hz), 4.92-5.04 (2H, m), 6.23 (1H, d, J=3.5 Hz), 7.31-7.43 (9H, m), 7.68-7.76 (3H, m) (+)ESI-MS (m/z): 579 (M+H)$^+$

EXAMPLE 30

The following compounds were obtained according to a similar manner to that of Example 4.

(1) 3-(Ethylthio)-4'-[2-[[(2R)-2-hydroxy-2-phenylethyl]-amino]ethyl]-4-biphenylcarboxylic acid hydrochloride NMR (DMSO-d$_6$, δ): 1.3 (3H, t, J=3.6 Hz), 3.02-3.26 (6H, m), 4.97 (1H, d, J=4.5 Hz), 6.22 (1H, br s), 7.32-7.41 (7H, m), 7.46 (1H, d, J=4.1 Hz), 7.52 (1H, s), 7.72 (2H, d, J=3.9 Hz), 7.96 (1H, d, J=4 Hz) (-)ESI-MS (m/z): 420 (M-H)$^-$ (2) 4'-[2-[[(2R)-2-Hydroxy-2-phenylethyl]amino]ethyl]-3-(methylthio)-4-biphenylcarboxylic acid hydrochloride NMR (DMSO-d$_6$, δ): 2.99-3.33 (9H, m), 4.99 (1H, d, J=7.6 Hz), 6.22 (1H, br s), 7.28-7.49 (9H, m), 7.75 (2H, d, J=8.1 Hz), 7.99 (1H, d, J=8.6 Hz) (-)ESI-MS (m/z): 406 (M-H)$^-$ (3) 3-Amino-4'-[2-[[(2R)-2-hydroxy-2-phenylethyl]amino]-ethyl]-4-biphenylcarboxylic acid dihydrochloride NMR (DMSO-d$_6$, δ): 3.05-3.22 (6H, m), 5.01 (1H, dd, J=2.8, 10 Hz), 6.84 (1H, dd, J=1.6, 8.4 Hz), 7.06 (1H, d, J=1.6 Hz), 7.27-7.41 (7H, m), 7.59 (2H, d, J=8.2 Hz), 7.77 (1H, d, J=8.3 Hz), 8.93 (1H, br s), 9.3 (1H, br s) (-)ESI-MS (m/z): 375 (M-H)$^-$ (4) 3-(Acetylamino)-4'-[2-[[(2R)-2-hydroxy-2-phenylethyl]-amino]ethyl]-4-biphenylcarboxylic acid hydrochloride NMR (DMSO-d$_6$, δ): 2.17 (3H, s), 3.05-3.33 (6H, m), 4.97 (1H, d, J=9.9 Hz), 6.21 (1H, br s), 7.28-7.46 (8H, m), 7.65 (2H, d, J=8.2 Hz), 8.05 (1H, d, J=8.4 Hz), 8.81 (1H, d, J=1.7 Hz) (-)ESI-MS (m/z): 417 (M-H)$^-$ (5) 4'-[2-[[(2R)-2-[3-(Benzyloxy)phenyl]-2-hydroxyethyl]-amino]ethyl]-3-isopropoxy-4-biphenylcarboxylic acid hydrochloride NMR (DMSO-d$_6$, δ): 1.26 (6H, d, J=5.9 Hz), 2.8-3.5 (6H, m), 4.76 (1H, m), 4.94 (1H, m), 5.11 (2H, s), 6.23 (1H, m), 7.0-7.8 (16H, m) MS (m/z): 526 (M+H)

(6) 4'-[2-[[(2R)-2-(3-Aminophenyl)-2-hydroxyethyl]amino]-ethyl]-3-isopropoxy-4-biphenylcarboxylic acid dihydrochloride NMR (DMSO-d$_6$, δ): 1.26 (6H, d, J=5.9 Hz), 2.8-3.5 (6H, m), 4.82 (1H, m), 5.02 (1H, m), 6.15 (1H, m), 7.2-7.8 (11H, m) MS (m/z): 435 (M+H)

EXAMPLE 31

The following compounds were obtained according to a similar manner to that of Example 1.

(1) 4'-[2-[[(2R)-2-(3-(Chlorophenyl)-2-hydroxyethyl)amino]-ethyl]-3-(ethylthio)-4-biphenylcarboxylic acid hydrochloride NMR (DMSO-d$_6$, δ): 1.31 (3H, t, J=7.3 Hz), 3.00-3.33 (8H, m), 5.01 (1H, d, J=8.3 Hz), 6.36 (1H, br s), 7.35-7.52 (8H, m), 7.73 (2H, d, J=8.2 Hz), 7.96 (1H, d, J=8.1 Hz) (-)ESI-MS (m/z): 454 (M-H)$^-$ (2) 4'-[2-[[(2R)-2-(3-Chlorophenyl)-2-hydroxyethyl]amino]-ethyl]-3-(isopropylthio)-4-biphenylcarboxylic acid hydrochloride NMR (DMSO-d$_6$, δ): 1.31 (6H, d, J=3.3 Hz), 3.02-3.26 (6H, m), 3.72-3.79 (1H, m), 5.00 (1H, d, J=4 Hz), 6.36 (1H, br s), 7.37-7.5 (7H, m), 7.6 (1H, d, J=0.7 Hz), 7.72 (2H, d, J=4.1 Hz), 7.9 (1H, d, J=4.1 Hz) (-)ESI-MS (m/z): 468 (M-H)$^-$ (3) 3-[(2-Ethoxyethyl)thio]-4'-[2-[[(2R)-2-hydroxy-2-phenylethyl]amino]ethyl]-4-biphenylcarboxylic acid hydrochloride NMR (DMSO-d$_6$, δ): 1.11 (3H, t, J=7 Hz), 2.99-3.33 (8H, m), 3.48 (2H, q, J=7 Hz), 3.67 (2H, t, J=6.3 Hz), 4.98 (1H, d, J=7.5 Hz), 7.23-7.42 (7H, m), 7.47 (1H, dd, J=1.4, 8.3 Hz), 7.59 (1H, d, J=0.9 Hz), 7.73 (2H, d, J=8.1 Hz), 7.95 (1H, d, J=8.1 Hz) (–)ESI-MS (m/z): 464 (M–H)⁻

(4) 3-[(2-Ethoxyethyl)thio]-4'-[2-[[(1S,2R)-2-hydroxy-1-methyl-2-phenylethyl]amino]ethyl]-4-biphenylcarboxylic acid hydrochloride NMR (DMSO-d₆, δ): 0.97 (3H, d, J=6.6 Hz), 1.11 (3H, t, J=7 Hz), 3.06-3.33 (7H, m), 3.48 (2H, q, J=7 Hz), 3.67 (2H, t, J=6.3 Hz), 5.19 (1H, br s), 6.14 (1H, br s), 7.27-7.5 (8H, m), 7.6 (1H, s), 7.75 (2H, d, J=8.1 Hz), 7.96 (1H, d, J=8.1 Hz) (–)ESI-MS (m/z): 478 (M–H)⁻

(5) 4'-[(2R)-2-[[(2R)-2-Hydroxy-2-phenylethyl]amino]-propyl]-3-(isopropylthio)-4-biphenylcarboxylic acid hydrochloride NMR (DMSO-d₆, δ): 1.16 (3H, d, J=5.7 Hz), 1.31 (6H, d, J=6.6 Hz), 2.7-3.24 (4H, m), 3.51-3.66 (1H, m), 3.73-3.8 (1H, m), 5.05 (1H, d, J=8.8 Hz), 6.24 (1H, br s), 7.3-7.48 (8H, m), 7.52 (1H, s), 7.76 (2H, d, J=J=7.1 Hz), 7.9 (1H, d, J=8.1 Hz) (–)ESI-MS (m/z): 448 (M–H)⁻

(6) Methyl 4'-[2-[(tert-butoxycarbonyl)-[(2R)-2-hydroxy-2-phenylethyl]amino]ethyl]-3-(methylthio)-4-biphenylcarboxylate NMR (DMSO-d₆, δ): 1.33 (9H, s), 2.71-2.85 (2H, m), 3.16-3.42 (4H, m), 3.84 (3H, s), 4.7-4.79 (1H, m), 5.46 (1H, dd, J=2.3, 7 Hz), 7.23-7.34 (7H, m), 7.47-7.51 (2H, m), 7.7 (2H, d, J=4 Hz), 7.98 (1H, d, J=4 Hz)

(7) Methyl 4'-[2-[(tert-butoxycarbonyl)[(2R)-2-hydroxy-2-phenylethyl]amino]ethyl]-3-(ethylthio)-4-biphenylcarboxylate (+)ESI-MS (m/z): 558 (M+Na)⁺

(8) tert-Butyl [2-[4'-formyl-3'-[isopropyl(methyl)amino]-4-biphenylyl]ethyl][(2R)-2-hydroxy-2-phenylethyl]carbamate
MS (m/z): 517 (M+H)⁺

EXAMPLE 32

The following compound was obtained according to a similar manner to that of Example 8.

Methyl 4'-[2-[benzyl[(2R)-2-hydroxy-2-phenylethyl]amino]ethyl]-3-nitro-4-biphenylcarboxylate (+)ESI-MS (m/z): 511 (M+H)⁺

EXAMPLE 33

The following compounds were obtained according to a similar manner to that of Example 8 followed by a similar manner to that of Example 9 and then a similar manner to that of Example 4.

(1) 4'-[2-[[(2R)-2-Hydroxy-2-phenylethyl]amino]ethyl]-2-isobutyl-4-biphenylcarboxylic acid hydrochloride NMR (DMSO-d₆, δ): 0.68 (6H, d, J=6.6 Hz), 1.54-1.68 (1H, m), 2.5 (2H, d, J=7.0 Hz), 3.0-3.3 (6H, m), 4.97-5.01 (1H, m), 6.21 (1H, br), 7.23-7.42 (10H, m), 7.78-7.84 (2H, m) MS (m/z): 416 (M-HCl—H)⁻

(2) 4'-[2-[[(2R)-2-(3-Chlorophenyl)-2-hydroxyethyl]amino]-ethyl]-2-isobutyl-4-biphenylcarboxylic acid hydrochloride NMR (DMSO-d₆, δ): 0.68 (6H, d, J=6.6 Hz), 1.54-1.68 (1H, m), 2.5 (2H, d, J=7.0 Hz), 3.0-3.3 (6H, m), 4.99-5.03 (1H, m), 6.23 (1H, br), 7.23-7.48 (10H, m), 7.78-7.84 (2H, m) MS (m/z): 450 (M-HCl—H)⁻

(3) 2-Butyl-4'-[2-[[(2R)-2-hydroxy-2-phenylethyl]amino]-ethyl]-4-biphenylcarboxylic acid hydrochloride NMR (DMSO-d₆, δ): 0.75 (3H, t, J=7.1 Hz), 1.1-1.2 (2H, m), 1.3-1.4 (2H, m), 2.6 (2H, t, J=7.2 Hz), 3.0-3.3 (6H, m), 4.95-5.00 (1H, m), 6.21 (1H, br), 7.23-7.42 (10H, m), 7.78-7.90 (2H, m) MS (m/z): 416 (M-HCl—H)⁻

(4) 2-Butyl-4'-[2-[[(2R)-2-(3-chlorophenyl)-2-hydroxyethyl]amino]ethyl]-4-biphenylcarboxylic acid hydrochloride NMR (DMSO-d₆, δ): 0.75 (3H, t, J=7.1 Hz), 1.1-1.2 (2H, m), 1.3-1.5 (2H, m), 2.6 (2H, t, J=7.2 Hz), 3.0-3.3 (6H, m), 4.99-5.03 (1H, m), 6.35 (1H, br), 7.23-7.48 (10H, m), 7.78-7.89 (2H, m) MS (m/z): 450 (M-HCl—H)⁻

(5) 3-(Cyclohexylamino)-4'-[2-[[(2R)-2-hydroxy-2-phenylethyl]amino]ethyl]-4-biphenylcarboxylic acid dihydrochloride NMR (DMSO-d₆, δ): 1.14-1.99 (10H, m), 2.95-3.32 (6H, m), 3.61 (1H, m), 5.00 (1H, dd, J=2.8, 10 Hz), 6.79 (1H, dd, J=1.2, 8.3 Hz), 6.91 (1H, s), 7.3-7.42 (7H, m), 7.65 (2H, d, J=8.2 Hz), 8.91 (1H, br s), 9.26 (1H, br s) (–)ESI-MS (m/z): 457 (M–H)⁻

EXAMPLE 34

The following compounds were obtained according to a similar manner to that of Example 9.

(1) Methyl 3-amino-4'-[2-[(tert-butoxycarbonyl)[(2R)-2-hydroxy-2-phenylethyl]amino]ethyl]-4-biphenylcarboxylate (+)ESI-MS (m/z): 513 (M+Na)⁺

(2) Methyl 3-(acetylamino)-4'-[2-[(tert-butoxycarbonyl)-[(2R)-2-hydroxy-2-phenylethyl]amino]ethyl]-4-biphenylcarboxylate (+)ESI-MS (m/z): 555 (M+Na)⁺

EXAMPLE 35

The following compounds were obtained according to a similar manner to that of Example 1 followed by a similar manner to that of Example 6.

(1) 4'-[2-[[(2R)-2-Hydroxy-2-phenylethyl]amino]ethyl]-3-(isobutylthio)-N-(methylsulfonyl)-4-biphenylcarboxamide hydrochloride NMR (DMSO-d₆, δ): 1.01 (6H, d, J=6.6 Hz), 1.76-1.9 (1H, m), 2.94 (2H, d, J=6.7 Hz), 3.06-3.21 (6H, m), 3.37 (3H, s), 4.97-5.02 (1H, m), 6.23 (1H, d, J=3.8 Hz), 7.28-7.42 (7H, m), 7.53 (1H, dd, J=1.2, 8.4 Hz), 7.61-7.65 (2H, m), 7.72 (2H, d, J=8.2 Hz), 8.89 (1H, br s), 9.2 (1H, br s), 12.20 (1H, br s) (–)ESI-MS (m/z): 525 (M–H)⁻

(2) 3-(Cyclohexylthio)-4'-[2-[[(2R)-2-hydroxy-2-phenylethyl]amino]ethyl]-N-(methylsulfonyl)-4-biphenylcarboxamide hydrochloride NMR (DMSO-d₆, δ): 1.14-1.99 (10H, m), 3.04-3.42 (6H, m), 3.36 (3H, s), 4.94-4.99 (1H, m), 6.22 (1H, d, J=3.8 Hz), 7.28-7.42 (7H, m), 7.6 (2H, s), 7.69 (1H, s), 7.73 (2H, s), 8.85 (1H, br s), 9.04 (1H, br s), 12.19 (1H, br s) (–)ESI-MS (m/z): 551 (M–H)⁻

(3) 4'-[2-[[(2R)-2-Hydroxy-2-phenylethyl]amino]ethyl]-N-(methylsulfonyl)-3-(propylthio)-4-biphenylcarboxamide hydrochloride NMR (DMSO-d₆, δ): 1.00 (3H, t, J=7.3 Hz), 1.57-1.68 (2H, m), 3.03 (2H, t, J=7.2 Hz), 3-3.34 (6H, m), 3.37 (3H, s), 4.96-5.01 (1H, m), 6.23 (1H, d, J=3.8 Hz), 7.3-7.42 (7H, m), 7.54 (1H, d, J=8.1 Hz), 7.63-7.67 (2H, m), 7.73 (2H, d, J=8.2 Hz) (–)ESI-MS (m/z): 511 (M–H)⁻

(4) 3-(Ethylthio)-4'-[2-[[(2R)-2-hydroxy-2-phenylethyl]amino]ethyl]-N-(methylsulfonyl)-4-biphenylcarboxamide hydrochloride NMR (DMSO-d₆, δ): 1.26 (3H, t, J=7.3 Hz), 3.07 (2H, q, J=7.3 Hz), 3.02-3.33 (6H, m), 3.36 (3H, s), 4.94-4.99 (1H, m), 6.22 (1H, d, J=3.8 Hz), 7.28-7.42 (7H, m), 7.53 (1H, dd, J=1.5, 8.1 Hz), 7.63-7.68 (2H, m), 7.73 (2H, d, J=8.2 Hz), 8.85 (1H, br s), 9.07 (1H, br s) (−)ESI-MS (m/z): 497 (M−H)⁻

(5) 3-(Cyclopentylthio)-4'-[2-[[(2R)-2-hydroxy-2-phenylethyl]amino]ethyl]-N-(methylsulfonyl)-4-biphenylcarboxamide hydrochloride NMR (DMSO-d₆, δ): 1.52-1.77 (6H, m), 1.99-2.16 (2H, m), 3.06-3.32 (6H, m), 3.37 (3H, s), 3.84-3.93 (1H, m), 4.97-5.02 (1H, m), 6.24 (1H, d, J=3.5 Hz), 7.28-7.42 (7H, m), 7.55 (1H, dd, J=1.3, 8.2 Hz), 7.64 (1H, d, J=8.1 Hz), 7.7-7.74 (3H, m), 8.9 (1H, br s), 9.26 (1H, br s) (−)ESI-MS (m/z): 537 (M−H)⁻

(6) 3-(Cyclohexylamino)-4'-[2-[[(2R)-2-hydroxy-2-phenylethyl]amino]ethyl]-N-(methylsulfonyl)-4-biphenylcarboxamide dihydrochloride NMR (DMSO-d₆, δ): 1.14-1.66 (8H, m), 1.91-1.99 (2H, m), 3.08-3.37 (6H, m), 3.37 (3H, s), 3.55-3.72 (1H, m), 5 (1H, d, J=7.6 Hz), 6.83 (1H, d, J=8.2 Hz), 6.92 (1H, s), 7.32-7.42 (7H, m), 7.68 (2H, d, J=8 Hz), 7.82 (1H, d, J=8.4 Hz), 8.93 (1H, br s), 9.29 (1H, br s) (+)ESI-MS (m/z): 536 (M+H)⁺

(7) 4'-[2-[[(2R)-2-Hydroxy-2-phenylethyl]amino]ethyl]-3-(isopropylamino)-N-(methylsulfonyl)-4-biphenylcarboxamide dihydrochloride NMR (DMSO-d₆, δ): 1.24 (6H, d, J=6.2 Hz), 2.98-3.32 (6H, m), 3.37 (3H, s), 3.89-3.98 (1H, m), 5.51 (1H, d, J=4.4 Hz), 6.86 (1H, d, J=8.4 Hz), 6.97 (1H, s), 7.3-7.42 (7H, m), 7.7 (2H, d, J=8.1 Hz), 7.83 (1H, d, J=8.4 Hz), 8.94 (1H, br s), 9.35 (1H, br s) (−)ESI-MS (m/z): 494 (M−H)⁻

(8) 4'-[2-[[(1S,2R)-2-Hydroxy-1-methyl-2-phenylethyl]amino]ethyl]-3-(isopropylthio)-N-(methylsulfonyl)-4-biphenylcarboxamide hydrochloride NMR (DMSO-d₆, δ): 0.97 (3H, d, J=6.6 Hz), 1.26 (6H, d, J=6.6 Hz), 3.11-3.45 (5H, m), 3.35 (3H, s), 3.6-3.73 (1H, m), 5.22 (1H, br s), 6.16 (1H, d, J=4.2 Hz), 7.24-7.46 (7H, m), 7.62 (2H, s), 7.72-7.76 (3H, m), 9.00 (2H, br s), 12.21 (1H, br s) (−)ESI-MS (m/z): 525 (M−H)⁻

EXAMPLE 36

The following compound was obtained according to a similar manner to that of Example 1.

tert-Butyl [(2R)-2-(6-chloro-3-pyridyl)-2-hydroxyethyl][2-[3'-isobutyl-4'-[[(methylsulfonyl)amino]carbonyl]-4-biphenylyl]ethyl]carbamate MS (m/z): 628 (M−H)⁻

EXAMPLE 37

The following compounds were obtained according to a similar manner to that of Example 6.

(1) 4'-[2-[[(2R)-2-(6-Chloro-3-pyridyl)-2-hydroxyethyl]amino]ethoxy]-3-(cyclohexyloxy)-N-(methylsulfonyl)-4-biphenylcarboxamide hydrochloride NMR (DMSO-d₆, δ): 1.3-1.8 (8H, m), 1.9-2.0 (2H, m), 3.2-3.5 (4H, m), 3.4 (3H, s), 4.4 (2H, br), 4.8(4.9 (1H, m), 5.1-5.2 (1H, m), 7.12 (2H, d, J=8.8 Hz), 7.3-7.4 (2H, m), 7.58 (1H, d, J=8.2 Hz), 7.7-7.9 (4H, m), 8.46 (1H, d, J=2.3 Hz), 9.1 (2H, br) MS (m/z): 586 (M-HCl—H)⁻

(2) 4'-[2-[[(2R)-2-Hydroxy-2-phenylethyl]amino]ethyl]-3-isopropoxy-N-(pentylsulfonyl)-4-biphenylcarboxamide hydrochloride NMR (DMSO-d₆, δ): 0.87 (3H, t, J=7.0 Hz), 1.21-1.46 (4H, m), 1.36 (6H, d, J=6.0 Hz), 1.67-1.81 (2H, m), 2.99-3.29 (6H, m), 3.51 (2H, t, J=7.7 Hz), 4.91-5.05 (2H, m), 6.23 (1H, d, J=4.0 Hz), 7.32-7.43 (9H, m), 7.67-7.76 (3H, m) (+)ESI-MS (m/z): 553 (M+H)⁺

(3) 3-Ethoxy-4'-[2-[[(2R)-2-hydroxy-2-phenylethyl]amino]ethoxy]-N-(methylsulfonyl)-4-biphenylcarboxamide hydrochloride NMR (DMSO-d₆, δ): 1.42 (3H, t, J=7.0 Hz), 3.08-3.29 (2H, m), 3.37 (3H, s), 3.44-3.47 (2H, m), 4.30 (2H, q, J=7.0 Hz), 4.36-4.40 (1H, m), 6.22 (1H, d, J=4.0 Hz), 7.11 (2H, d, J=8.4 Hz), 7.31-7.43 (7H, m), 7.73 (1H, d, J=8.4 Hz), 7.77 (2H, d, J=8.4 Hz), 9.18 (3H, br) (−)ESI-MS (m/z): 497 (M−H)⁻

(4) 4'-[3-[[(2R)-2-Hydroxy-2-phenylethyl]amino]propyl]-3-isopropoxy-N-(methylsulfonyl)-4-biphenylcarboxamide hydrochloride NMR (DMSO-d₆, δ): 1.38 (6H, d, J=5.60 Hz), 1.88-2.18 (2H, m), 2.72 (2H, t, J=7.0 Hz), 2.87-3.23 (4H, m), 3.38 (3H, s), 4.87-5.08 (2H, m), 6.18 (1H, d, J=3.40 Hz), 7.26-7.45 (9H, m), 7.66-7.83 (3H, m) (−)ESI-MS (m/z): 509 (M−H)⁻

(5) 3-(Cyclohexyloxy)-4'-[3-[[(2R)-2-hydroxy-2-phenylethyl]amino]propyl]-N-(methylsulfonyl)-4-biphenylcarboxamide hydrochloride NMR (DMSO-d₆, δ): 1.26-1.83 (8H, m), 1.8-8-2.13 (4H, m), 2.72 (2H, t, J=7.0 Hz), 2.88-3.22 (4H, m), 3.38 (3H, s), 4.74-4.88 (1H, m), 4.89-5.04 (1H, m), 6.18 (1H, d, J=3.40 Hz), 7.27-7.48 (9H, m), 7.64-7.82 (3H, m) (−)ESI-MS (m/z): 549 (M−H)⁻

(6) 3-Ethoxy-4'-[3-[[(2R)-2-hydroxy-2-phenylethyl]amino]propyl]-N-(methylsulfonyl)-4-biphenylcarboxamide hydrochloride NMR (DMSO-d₆, δ): 1.54-1.87 (6H, m), 1.93-2.14 (4H, m), 2.71 (2H, t, J=7.0 Hz), 2.89-3.23 (4H, m), 3.38 (3H, s), 4.90-5.04 (1H, m), 6.18 (1H, d, J=3.60 Hz), 7.25-7.71 (12H, m) (−)ESI-MS (m/z): 495 (M−H)⁻

(7) 4'-[3-[[(2R)-2-Hydroxy-2-phenylethyl]amino]propyl]-3-isobutyl-N-(methylsulfonyl)-4-biphenylcarboxamide hydrochloride NMR (DMSO-d₆, δ): 0.87 (6H, d, J=6.53 Hz), 1.71-2.18 (3H, m), 2.63-2.80 (4H, m), 2.88-3.24 (4H, m), 3.38 (3H, s), 4.88-5.05 (1H, m), 6.18 (1H, d, J=4.0 Hz), 7.26-7.44 (7H, m), 7.49-7.73 (5H, m), 12.19 (1H, s) (−)ESI-MS (m/z): 507 (M−H)⁻

(8) 3-Cyclopentyl-4'-[3-[[(2R)-2-hydroxy-2-phenylethyl]amino]propyl]-N-(methylsulfonyl)-4-biphenylcarboxamide hydrochloride NMR (DMSO-d₆, δ): 1.52-2.2 (10H, m), 2.71 (2H, t, J=7.3 Hz), 2.87-3.23 (4H, m), 3.39 (3H, s), 4.89-5.03 (1H, m), 6.18 (1H, d, J=3.5 Hz), 7.28-7.44 (7H, m), 7.44-7.59 (2H, m), 7.59-7.72 (3H, m), 12.21 (1H, s) (−)ESI-MS (m/z): 519 (M−H)⁻

(9) 4'-[2-[[(2R)-2-Hydroxy-2-(3-pyridyl)ethyl]amino]ethyl]-3-isobutoxy-N-(methylsulfonyl)-4-biphenylcarboxamide dihydrochloride NMR (DMSO-d₆, δ): 1.05 (6H, d, J=7 Hz), 2.06-2.18 (1H, m), 3.04-3.14 (2H, m), 3.17-3.3 (4H, m), 3.37 (3H, s), 4.04 (2H, d, J=6.2 Hz), 5.2-5.27 (1H, m), 7.35-7.42 (4H, m), 7.71-7.79 (3H, m), 7.84-7.9 (1H, m), 8.34 (1H, d, J=7.7 Hz), 8.76-8.87 (2H, m), 11.27 (1H, s) (−)ESI-MS (m/z): 510 (M−H)⁻

(10) 4'-[2-[[(2R)-2-Hydroxy-2-(3-pyridyl)ethyl]amino]ethyl]-3-isobutoxy-4-biphenylcarboxylic acid dihydrochloride NMR (DMSO-d₆, δ): 1.02 (6H, d, J=3.29 Hz), 1.99-2.12 (1H, m), 3.04-3.15 (2H, m), 3.18-3.31 (3H, m), 3.34-3.46 (1H, m), 3.93 (2H, d, J=6.22 Hz), 5.27-5.36 (1H, m), 7.24-7.31 (2H, m), 7.36-7.42 (2H, m), 7.70-7.76 (3H, m), 7.96-8.04 (1H, m), 8.50 (1H, d, J=8.05 Hz), 8.83-8.93 (2H, m) (−)ESI-MS (m/z): 433 (M−H)⁻

(11) 4'-[2-[[(2R)-2-Hydroxy-2-(3-pyridyl)ethyl]amino]ethyl]-3-isobutyl-4-biphenylcarboxylic acid dihydrochloride NMR (DMSO-$d_6$, δ): 0.88 (6H, d, J=6.53 Hz), 1.73-1.97 (1H, m), 2.99-3.52 (6H, m), 5.24-5.38 (1H, m), 7.39 (2H, d, J=8.03 Hz), 7.49-7.62 (2H, m), 7.70 (2H, d, J=8.03 Hz), 7.87 (1H, d, J=8.53 Hz), 7.93-8.05 (1H, m), 8.50 (1H, d, J=8.53 Hz), 8.79-8.96 (2H, m) (−)ESI-MS (m/z): 417 (M−H)⁻

(12) 4'-[3-[[(2R)-2-Hydroxy-2-(3-pyridyl)ethyl]amino]-propyl]-3-isobutoxy-4-biphenylcarboxylic acid dihydrochloride NMR (DMSO-$d_6$, δ): 1.02 (6H, d, J=6.59 Hz), 1.98-2.11 (3H, m), 2.49-2.52 (3H, m), 2.73 (2H, t, J=7.68 Hz), 2.93-3.04 (2H, m), 3.11-3.23 (1H, m), 3.28-3.39 (1H, m), 3.93 (2H, d, J=6.59 Hz), 5.24-5.31 (1H, m), 7.23-7.38 (4H, m), 7.66-7.75 (3H, m), 7.94-8.01 (1H, m), 8.48 (1H, d, J=8.05 Hz), 8.81-8.91 (2H, m) (−)ESI-MS (m/z): 447 (M−H)⁻

(13) 4'-[3-[[(2R)-2-Hydroxy-2-(3-pyridyl)ethyl]amino]-propyl]-3-isobutoxy-N-(methylsulfonyl)-4-biphenylcarboxamide dihydrochloride NMR (DMSO-$d_6$, δ): 1.05 (6H, d, J=6.59 Hz), 1.93-2.19 (3H, m), 2.73 (2H, t, J=7.68 Hz), 2.92-3.04 (2H, m), 3.08-3.21 (1H, m), 3.24-3.35 (1H, m), 3.38 (1H, s), 4.04 (2H, d, J=6.22 Hz), 5.12-5.24 (1H, m), 6.43-6.77 (1H, br), 7.33-7.41 (4H, m), 7.69-7.84 (4H, m), 8.23-8.30 (1H, m), 8.72-8.82 (2H, m), 11.3 (1H, s) (−)ESI-MS (m/z): 524 (M−H)⁻

EXAMPLE 38

To a solution of tert-butyl [2-[4'-(aminosulfonyl)-3'-(cyclohexyloxy)-4-biphenylyl]ethyl][(2R)-2-phenyl-2-(tetrahydro-2H-pyran-2-yloxy)ethyl]carbamate (188 mg) in dichloromethane (2 ml) were added triethylamine (0.12 ml) and butanoyl chloride (0.087 ml) at approximately 0° C., and the mixture was stirred at room temperature overnight. The mixture was diluted with ethyl acetate, washed with water, aqueous hydrochloric acid solution (0.5N) and brine, dried over sodium sulfate and evaporated under reduced pressure to give residue (230 mg). To a solution of the above residue in methanol (5 ml) was added 4-methylbenzenesulfonic acid (23 mg) at room temperature and the mixture was stirred overnight. The mixture was diluted with ethyl acetate, washed with water and brine, dried over sodium sulfate and evaporated under reduced pressure. The residue was purified by column chromatography on silica gel (hexane/ethyl acetate=6/4) to give tert-butyl [2-[4'-[(butyrylamino)sulfonyl]-3'-(cyclohexyloxy)-4-biphenylyl]ethyl][(2R)-2-hydroxy-2-phenylethyl]carbamate (145 mg).

(−)ESI-MS (m/z): 663 (M−H)⁻

EXAMPLE 39

To a solution of methyl 4'-[2-[(tert-butoxycarbonyl)-[(2R)-2-hydroxy-2-phenylethyl]amino]ethyl]-3-(ethylthio)-4-biphenylcarboxylate (300 mg) in chloroform (6 ml) and N,N-dimethylformamide (3 ml) was added m-chloroperbenzoic acid (541 mg) and the mixture was stirred at room temperature for 1 hour. The mixture solution was poured into water and extracted with methylene chloride. The organic layer was washed with brine, dried over magnesium sulfate and evaporated under reduced pressure. The residue was purified by column chromatography on silica gel (hexane/ethyl acetate=2/1) to give a sulfone product. To a solution of the product in methanol (3 ml) was added aqueous solution of sodium hydroxide (1N, 867 μl) at room temperature and the mixture was stirred at 45° C. for 3 hours. The mixture solution was acidified with hydrochloric acid aqueous solution, poured into water and extracted with ethyl acetate. The organic layer was washed with brine, dried over magnesium sulfate and evaporated under reduced pressure to give a benzoic acid product. To a solution of the product in ethyl acetate (1.5 ml) was added hydrogen chloride ethyl acetate solution (4N, 1.5 ml) at 0° C. and the mixture was stirred at room temperature overnight. The resultant solid was collected by filtration and dried to give 3-(ethylsulfonyl)-4'-[2-[[(2R)-2-hydroxy-2-phenylethyl]amino]-ethyl]-4-biphenylcarboxylic acid hydrochloride (50 mg).

NMR (DMSO-$d_6$, δ): 1.21 (3H, t, J=3.7 Hz), 3.03-3.27 (6H, m), 3.61 (2H, q, J=3.7 Hz), 4.98 (1H, d, J=5 Hz), 6.23 (1H, br s), 7.33-7.45 (7H, m), 7.76 (2H, d, J=4.1 Hz), 7.84 (1H, d, J=4 Hz), 8.09 (1H, dd, J=0.9, 4 Hz), 8.13 (1H, d, J=0.9 Hz), 8.87 (1H, br s), 9.15 (1H, br s) (−)ESI-MS (m/z): 452 (M−H)⁻

EXAMPLE 40

The suspension of 4'-[2-[[(2R)-2-hydroxy-2-phenylethyl]amino]ethyl]-3-(isopropylthio)-4-biphenylcarboxylic acid hydrochloride in hydrogen chloride ethanol solution (5.5M, 1 ml) was stirred under reflux for 1.5 hours. The mixture solution was evaporated under reduced pressure and the resultant solid was washed with isopropyl ether to give ethyl 4'-[2-[[(2R)-2-hydroxy-2-phenylethyl]amino]ethyl]-3-(isopropylthio)-4-biphenylcarboxylate hydrochloride (37 mg).

NMR (DMSO-$d_6$, δ): 1.30 (6H, d, J=6.6 Hz), 1.32 (3H, t, J=7.4 Hz), 2.99-3.34 (6H, m), 3.71-3.84 (1H, m), 4.3 (2H, q, J=7.1 Hz), 4.97-5.02 (1H, m), 6.23 (1H, d, J=3.8 Hz), 7.31-7.42 (7H, m), 7.53 (1H, dd, J=1.4, 8.1 Hz), 7.65 (1H, s), 7.72 (2H, d, J=8.2 Hz), 7.88 (1H, d, J=8.1 Hz) (+)ESI-MS (m/z): 464 (M+H)⁺

EXAMPLE 41

To a solution of methyl 3-(acetylamino)-4'-[2-[benzyl[(2R)-2-phenyl-2-(tetrahydro-2H-pyran-2-yloxy)ethyl]amino]ethyl]-4-biphenylcarboxylate in ethyl acetate (6 ml) was added hydrogen chloride ethyl acetate solution (4N, 2 ml) and stirred for 30 minutes at room temperature. The mixture was poured into sodium hydroxide aqueous solution (1N) and extracted with ethyl acetate. The organic layer was washed with brine, dried over magnesium sulfate and evaporated to give methyl 3-(acetylamino)-4'-[2-[benzyl[(2R)-2-hydroxy-2-phenylethyl]amino]ethyl]-4-biphenylcarboxylate (177 mg).

(+)ESI-MS (m/z): 523 (M+H)⁺

EXAMPLE 42

To a solution of benzyl [(2R)-2-[4-(benzyloxy)-3-[(methylsulfonyl)amino]phenyl]-2-hydroxyethyl][2-(4-bromophenyl)ethyl]carbamate (600 mg) and [3-isopropoxy-4-[(N-methanesulfonyl)carbamoyl]phenyl]boronic acid (365 mg) in 1,2-dimethoxyethane (9 ml) were added sodium carbonate aqueous solution (2M, 2.03 ml) and tetrakis-(triphenylphosphine)palladium (89.5 mg) at room temperature and stirred at 75° C. for 10 hours under nitrogen. The mixture was poured into hydrochloric acid aqueous solution (1M) and ethyl acetate, added active carbon and stirred at room temperature for 2 hours. The mixture was filtrated and partitioned. The organic layer was washed with water and brine, dried over magnesium sulfate and evaporated. The residue was purified by column chromatography on silica gel (hexane/ethyl acetate=2/3) to give a biphenyl product. To a solution of the biphenyl product (303 mg) in methanol (15 ml) was added palladium on carbon (150 mg), the atmosphere was replaced with hydrogen and stirred for 40 minutes at room temperature. The mixture was diluted with chloroform and filtrated. To the solution was added hydrogen chloride ethyl acetate solution (4N, 110 μl) and evaporated to give 4'-[2-[[(2R)-2-hydroxy-2-[4-hydroxy-3-[(methylsulfonyl)-amino]phenyl]ethyl]amino]ethyl]-3-isopropoxy-N-methylsulfonyl)-4-biphenylcarboxamide hydrochloride (188 mg).

NMR (DMSO-$d_6$, δ): 1.37 (6H, d, J=6 Hz), 2.95 (3H, s), 3.38 (3H, s), 2.98-3.57 (6H, m), 4.87 (1H, d, J=7.9 Hz), 4.92-5.04 (1H, m), 6.12 (1H, br s), 6.93 (1H, d, J=8.2 Hz), 7.08 (1H, dd, J=1.9, 8.3 Hz), 7.25 (1H, d, J=1.8 Hz), 7.36-7.41 (4H, m), 7.74 (2H, d, J=6.5 Hz), 7.78 (1H, d, J=6.4 Hz), 8.81 (1H, s), 8.85 (1H, br s), 9.11 (1H, br s), 10.03 (1H, s), 11.22 (1H, s) (−)ESI-MS (m/z): 604 (M−H)⁻

EXAMPLE 43

To a solution of 4'-[2-[(tert-butoxycarbonyl)[(2R)-2-phenyl-2-(tetrahydro-2H-pyran-2-yloxy)ethyl]amino]ethyl]-3-isopropoxy-4-biphenylcarboxylic acid (224 mg) in N,N-dimethylformamide (2 ml) was added 1,1'-carbonyldiimidazole (72 mg) at room temperature and the mixture was stirred at the same temperature for 1 hour. 1-Pentanesulfonamide (67 mg) and 1,8-diazabicyclo[5.4.0]-7-undecene (0.067 ml) were added to the mixture at room temperature. The mixture was stirred at 70° C. for 4 hours. After cooling down to room temperature, the mixture was diluted with ethyl acetate, washed with aqueous hydrochloric acid solution (0.5N) and brine, dried over sodium sulfate and evaporated under reduced pressure to give residue (403 mg). To a solution of the above residue in methanol (2 ml) was added 4-methylbenzenesulfonic acid at room temperature and the mixture was stirred at the same temperature for 2 days. The mixture was diluted with ethyl acetate, washed with water and brine, dried over sodium sulfate and evaporated under reduced pressure. The residue was purified by column chromatography on silica gel (hexane/ethyl acetate=7/3) to give tert-butyl [(2R)-2-hydroxy-2-phenylethyl][2-[3'-isopropoxy-4'-[[(pentylsulfonyl)amino]carbonyl]-4-biphenylyl]ethyl]carbamate (179 mg).

(+)ESI-MS (m/z): 675 (M+Na)⁺

EXAMPLE 44

A mixture of tert-butyl [(2R)-2-hydroxy-2-phenylethyl][2-(4-iodophenoxy)ethyl]carbamate (250 mg), [3-ethoxy-4-[[(methylsulfonyl)amino]carbonyl]phenyl]boronic acid (223 mg), [1,1'-bis(diphenylphosphino)ferrocene]-dichloropalladium(II), complex with dichloromethane (1:1, 114 mg), 1,1'-bis(diphenylphosphino)ferrocene (32 mg), N,N-dimethylformamide (5 ml), and 2N sodium carbonate solution (0.99 ml) was stirred at 80° C. for 1 hour. After cooling to room temperature, the mixture was quenched by the addition of 1N hydrochloric acid (1.99 ml) and partitioned between ethyl acetate (20 ml) and water (20 ml). The organic layer was separated, washed with water (20 ml×2) and brine (20 ml), and dried over magnesium sulfate. Filtration followed by evaporation gave a brown foam which was chromatographed on silica gel (eluent: hexane/ethyl acetate) to give tert-butyl [2-[[3'-ethoxy-4'-[[(methylsulfonyl)amino]carbonyl]-4-biphenylyl]oxy]ethyl][(2R)-2-hydroxy-2-phenylethyl]carbamate (84.5 mg) as a pale orange solid.

(−)ESI-MS (m/z): 597 (M−H)⁻

EXAMPLE 45

In a reaction vessel were added tert-butyl [(2R)-2-hydroxy-2-phenylethyl][2-(4-iodophenoxy)ethyl]carbamate (200 mg), [3-isopropoxy-4-[[(methylsulfonyl)amino]carbonyl]phenyl]boronic acid (150 mg), [1,1'-bis(diphenylphosphino)ferrocene]dichloropalladium(II), complex with dichloromethane (1:1, 33.8 mg), toluene (3.2 ml), ethanol (0.8 ml), and 2N sodium carbonate solution (0.66 ml). The vessel was placed in a microwave and irradiation was adjusted to keep the temperature 100° C. and the reaction was performed for 2 hours. After cooling to room temperature, the mixture was quenched by the addition of 1N hydrochloric acid (1.32 ml) and partitioned between ethyl acetate (20 ml) and water (20 ml). The organic layer was separated, washed with brine (20 ml), and dried over magnesium sulfate. Filtration followed by evaporation gave a brown foam which was chromatographed on silica gel (eluent: hexane/ethyl acetate) to give tert-butyl [(2R)-2-hydroxy-2-phenylethyl]-[2-[[3'-isopropoxy-4'-[[(methylsulfonyl)amino]carbonyl]-4-biphenylyl]oxy]ethyl]carbamate (20.4 mg) as a pale yellow solid.

(−)ESI-MS (m/z): 611 (M−H)⁻

EXAMPLE 46

A mixture of tert-butyl [2-[3'-(cyclohexyloxy)-4'-[[(methylsulfonyl)amino]carbonyl]-4-biphenylyl]ethyl][(2R)-2-hydroxy-2-(4-nitrophenyl)ethyl]carbamate (281 mg), iron powder (69.1 mg), ammonium chloride (11 mg), ethanol (4.2 ml), and water (1.4 ml) was refluxed for 1 hour. After cooling to room temperature, the insoluble solid was filtered off through a Celite pad and washed with ethyl acetate (20 ml). The filtrate was washed with brine (20 ml) and dried over magnesium sulfate. Filtration followed by evaporation gave a yellow foam (271 mg) which was chromatographed on silica gel (eluent: hexane/ethyl acetate) to give tert-butyl [(2R)-2-(4-aminophenyl)-2-hydroxyethyl]-[2-[3'-(cyclohexyloxy)-4'-[[(methylsulfonyl)amino]carbonyl]-4-biphenylyl]ethyl]carbamate (104 mg) as a pale yellow solid.

(−)ESI-MS (m/z): 650 (M−H)⁻

EXAMPLE 47

The following compounds were obtained according to a similar manner to that of Example 14.

(1) 4'-[2-[[(2R)-2-(4-Aminophenyl)-2-hydroxyethyl]amino]-ethoxy]-3-isopropoxy-N-(methylsulfonyl)-4-biphenylcarboxamide dihydrochloride NMR (DMSO-$d_6$, δ): 1.38 (6H, d, J=6.2 Hz), 3.05-3.29 (2H, m), 3.39 (3H, s), 3.42-3.49 (2H, m), 4.34-4.43 (2H, m), 4.96-5.02 (2H, m), 6.23 (1H, br), 7.11 (2H, d, J=8.8 Hz), 7.19 (2H, d, J=6.6 Hz), 7.36 (1H, dd, J=1.5, 8.1 Hz), 7.40-7.41 (3H, m), 7.77 (2H, d, J=8.8 Hz), 7.78 (1H, d, J=8.1 Hz), 8.97 (1H, br), 9.19 (1H, br), 9.41 (2H, br), 11.2 (1H, br) (−)ESI-MS (m/z): 526 (M−H)⁻

(2) 4'-[2-[[(2R)-2-Hydroxy-2-phenylethyl]amino]ethyl]-3-(2-methoxyethoxy)-N-(methylsulfonyl)-4-biphenylcarboxamide hydrochloride NMR (DMSO-$d_6$, δ): 3.0-3.5 (6H, m), 3.36 (3H, s), 3.39 (3H, s), 3.72-3.77 (2H, m), 4.41-4.45 (2H, m), 4.98-5.03 (1H, m), 6.23 (1H, d, J=6 Hz), 7.31-7.85 (12H, m), 8.6-9.6 (2H, m)

(3) 4'-[2-[[(2R)-2-Hydroxy-2-phenylethyl]amino]ethyl]-N-(methylsulfonyl)-3-(2,2,2-trifluoroethoxy)-4-biphenylcarboxamide hydrochloride NMR (DMSO-$d_6$, δ): 3.0-3.6 (6H, m), 3.32 (3H, s), 4.6-5.1 (3H, m), 6.23 (1H, d, J=4 Hz), 7.2-7.6 (9H, m), 7.63 (1H, d, J=8 Hz), 7.78 (2H, d, J=8.5 Hz) (+)ESI-MS (m/z): 537 (M+H)⁺

(4) 3-(2-Fluoroethoxy)-4'-[2-[[(2R)-2-hydroxy-2-phenylethyl]amino]ethyl]-N-(methylsulfonyl)-4-biphenylcarboxamide hydrochloride (+)ESI-MS (m/z): 501 (M+H)$^+$ (5) 4'-[2-[[(1S,2R)-2-Hydroxy-0.1-methyl-2-phenylethyl]amino]ethyl]-N-(methylsulfonyl)-3-(2,2,2-trifluoroethoxy)-4-biphenylcarboxamide hydrochloride (−)ESI-MS (m/z): 549 (M−H)$^-$ (6) 3-(3-Fluoropropoxy)-4'-[2-[[(2R)-2-hydroxy-2-phenylethyl]amino]ethyl]-N-(methylsulfonyl)-4-biphenylcarboxamide hydrochloride NMR (DMSO-d$_6$, δ): 2.13-2.23 (2H, m), 3.02-3.35 (6H, m), 3.34 (3H, s), 4.32 (2H, t, J=6.1 Hz), 4.6-4.75 (2H, m), 4.95-4.99 (1H, m), 6.23 (1H, d, J=4 Hz), 7.31-7.41 (9H, m), 7.67 (1H, d, J=8 Hz), 7.76 (2H, d, J=8.2 Hz) (+)ESI-MS (m/z): 515 (M+H)$^+$ (free)

(7) 3-(3-Fluoropropoxy)-4'-[2-[[(1S,2R)-2-hydroxy-1-methyl-2-phenylethyl]amino]ethyl]-N-(methylsulfonyl)-4-biphenylcarboxamide hydrochloride NMR (DMSO-d$_6$, δ): 0.97 (3H, d, J=6.7 Hz), 2.14-2.23 (2H, m), 3.08-3.48 (5H, m), 3.35 (3H, s), 4.31-4.34 (2H, m), 4.61-4.76 (2H, m), 5.18-5.21 (1H, m), 6.16 (1H, d, J=4.3 Hz), 7.27-7.77 (9H, m), 7.67 (1H, d, J=8 Hz), 7.77 (2H, d, J=8.3 Hz) (+)ESI-MS (m/z): 529 (M+H)$^+$ (8) 4'-[2-[[(2R)-2-(4-Aminophenyl)-2-hydroxyethyl]amino]-ethoxy]-3-(cyclohexyloxy)-N-(methylsulfonyl)-4-biphenylcarboxamide dihydrochloride NMR (DMSO-d$_6$, δ): 1.34-1.64 (6H, m), 1.69-1.78 (2H, m), 1.93-2.01 (2H, m), 3.04-3.15 (1H, m), 3.21-3.30 (1H, m), 3.39 (3H, s), 3.42-3.48 (2H, m), 4.34-4.43 (2H, m), 4.83 (1H, heptuplet, J=3.7 Hz), 5.02 (1H, dd, J=1.8, 10.3 Hz), 6.25 (1H, br), 7.12 (2H, d, J=8.8 Hz), 7.24 (2H, d, J=7.7 Hz), 7.35 (1H, dd, J=1.5, 8.1 Hz), 7.42-7.44 (3H, m), 7.76 (2H, d, J=8.8 Hz), 7.78 (1H, d, J=8.1 Hz), 9.00 (1H, br), 9.26 (1H, br), 9.60 (2H, br), 11.1 (1H, br) (−)ESI-MS (m/z): 566 (M−H)$^-$ (9) 4'-[2-[[(2R)-2-(3-Aminophenyl)-2-hydroxyethyl]amino]-ethyl]-3-(cyclohexyloxy)-N-(methylsulfonyl)-4-biphenylcarboxamide dihydrochloride NMR (DMSO-d$_6$, δ): 1.33-1.64 (6H, m), 1.69-1.76 (2H, m), 1.93-1.99 (2H, m), 2.97-3.27 (6H, m), 3.39 (3H, s), 4.82 (1H, heptuplet, J=3.7 Hz), 5.05 (1H, dd, J=2.2, 10.3 Hz), 6.40 (1H, br), 7.20-7.46 (8H, m), 7.74 (2H, d, J=8.4 Hz), 7.78 (1H, d, J=8.1 Hz), 8.98 (1H, br), 9.40 (1H, br), 9.89 (2H, br), 11.2 (1H, br) (−)ESI-MS (m/z): 550 (M−H)$^-$

EXAMPLE 48

To a solution of tert-butyl [(2R)-2-[6-(acetylamino)-3-pyridyl]-2-[[tert-butyl(dimethyl)silyl]oxy]ethyl][2-[3'-isopropoxy-4'-[[(methylsulfonyl)amino]carbonyl]-4-biphenylyl]ethyl]carbamate (211 mg) in ethanol (2.1 ml) was added 1N sodium hydroxide (2.74 ml) and the mixture was refluxed for 20 hours. After cooling to room temperature, the mixture was quenched by the addition of 1N hydrochloric acid (2.74 ml) and the solvent was removed by evaporation. The residue was suspended in chloroform/methanol (4/1, 5 ml) and dried over magnesium sulfate. Filtration followed by evaporation gave a brown solid (164 mg). The solid was dissolved in 4N hydrogen chloride in dioxane (2 ml) and the mixture was stirred at room temperature for 16 hours. The solvent was concentrated in vacuo and the residual solid was dissolved in water (5 ml) and treated with activated carbon. After stirring for 3 hours, the mixture was filtered and the filtrate was adjusted to pH 7 by the addition of 1N sodium hydroxide. The precipitates were collected by filtration, washed with water, and dried under reduced pressure to give 4'-[2-[[(2R)-2-(6-amino-3-pyridyl)-2-hydroxyethyl]amino]-ethyl]-3-isopropoxy-N-(methylsulfonyl)-4-biphenylcarboxamide (73.5 mg) as a pale gray solid.

NMR (DMSO-d$_6$, δ): 1.27 (6H, d, J=6.2 Hz), 2.88-2.99 (4H, m), 2.98 (3H, s), 3.06-3.13 (2H, m), 4.63-4.73 (1H, m), 5.71 (1H, br), 5.91 (2H, br s), 6.43 (1H, d, J=8.4 Hz), 7.18-7.22 (2H, m), 7.32 (2H, d, J=8.4 Hz), 7.37 (1H, dd, J=2.6, 8.4 Hz), 7.47 (1H, d, J=7.7 Hz), 7.63 (2H, d, J=8.4 Hz), 7.88 (1H, d, J=2.6 Hz), 8.02 (2H, br) (−)ESI-MS (m/z): 511 (M−H)$^-$

EXAMPLE 49

To a solution of methyl 4'-[3-[(tert-butoxycarbonyl)-[(2R)-2-hydroxy-2-phenylethyl]amino]propyl]-3-(cyclohexyloxy)-4-biphenylcarboxylate (147 mg) in methanol (2.94 ml) was added 1N sodium hydroxide (0.5 ml) and the mixture was stirred at room temperature for 18 hours, at which time the starting material was still remained. The mixture was warmed to 50° C. and stirred for 3 hours, at which time the reaction was complete. After cooling to room temperature, the mixture was quenched by the addition of 1N hydrochloric acid (0.5 ml) and diluted with ethyl acetate (10 ml). The mixture was with water (10 ml×2) and brine (10 ml), and dried over magnesium sulfate. Filtration followed by evaporation gave 4'[3-[(tert-butoxycarbonyl)-[(2R)-2-hydroxy-2-phenylethyl]amino]propyl]-3-(cyclohexyloxy)-4-biphenylcarboxylic acid (141 mg) as a pale yellow solid.

(−)ESI-MS (m/z): 572 (M−H)$^-$

EXAMPLE 50

To a solution of 4'-[3-[(tert-butoxycarbonyl)[(2R)-2-hydroxy-2-phenylethyl]amino]propyl]-3-(cyclohexyloxy)-4-biphenylcarboxylic acid (133 mg) in N,N-dimethylformamide (1.3 ml) was added N,N'-carbonyldiimidazole (41.3 mg) and the mixture was stirred at room temperature for 5 hours. To the mixture were added 1-propanesulfonamide (31.4 mg) and 1,8-diazabicyclo[5.4.0]undec-7-ene (41.6 µl) and the mixture was stirred at 50° C. for 14 hours. After cooling to room temperature, the mixture was diluted with ethyl acetate (10 ml) and washed with water (10 ml×2) and brine (10 ml). The solution was dried over magnesium sulfate then concentrated in vacuo to give a crude solid which was chromatographed on silica gel (eluent: hexane/ethyl acetate) to give tert-butyl [3-[3'-(cyclohexyloxy)-4'-[[(propylsulfonyl)amino]carbonyl]-4-biphenylyl]propyl][(2R)-2-hydroxy-2-phenylethyl]carbamate (63.5 mg) as a white solid.

(−)ESI-MS (m/z): 677 (M−H)$^-$

EXAMPLE 51

To a solution of methyl 4'-[2-[[(2R)-2-[6-(acetylamino)-3-pyridyl]-2-[[tert-butyl(dimethyl)silyl]oxy]-ethyl](tert-butoxycarbonyl)amino]ethyl]-3-isopropoxy-4-biphenylcarboxylate (214 mg) in ethanol (2.1 ml) was added 1N sodium hydroxide (3.03 ml) and the mixture was refluxed for 20 hours. After cooling to room temperature, the mixture was quenched by the addition of 1N hydrochloric acid (3.03 ml) and the solvent was removed by evaporation. The residue was suspended in chloroform/methanol (4/1, 5 ml) and dried over magnesium sulfate. Filtration followed by evaporation gave a yellow solid (99.7 mg). The solid was dissolved in 4N hydrogen chloride in dioxane (2 ml) and the mixture was stirred at room temperature for 16 hours. The solvent was concentrated in vacuo and the residual solid was purified by ODS column (eluent: water/methanol). The fraction containing the target compound were combined and acidified with 1N hydrochloric acid (1 ml). The mixture was concentrated in vacuo to give 4'-[2-[[(2R)-2-(6-amino-3-pyridyl)-2-hydroxyethyl]amino]ethyl]-3-isopropoxy-4-biphenylcarboxylic acid dihydrochloride (63.2 mg) as a white solid.

NMR (DMSO-$d_6$, δ): 1.31 (6H, d, J=6.2 Hz), 3.02-3.26 (6H, m), 4.82 (1H, heptuplet, J=6.2 Hz), 4.98 (1H, br), 6.44 (1H, br), 7.03 (1H, d, J=9.5 Hz), 7.27 (1H, dd, J=1.5, 8.1 Hz), 7.32 (1H, d, J=1.5 Hz), 7.38 (2H, d, J=8.4 Hz), 7.70 (1H, d, J=8.1 Hz), 7.71 (2H, d, J=8.4 Hz), 7.93-7.96 (2H, m), 8.11 (2H, br), 9.07 (1H, br), 9.22 (1H, br), 12.5 (1H, br), 14.0 (1H, br) (−)ESI-MS (m/z): 434 (M−H)⁻

EXAMPLE 52

The mixture of tert-butyl [(2R)-2-(6-chloro-3-pyridyl)-2-hydroxyethyl][2-[3'-isobutyl-4'-[[(methylsulfonyl)amino]carbonyl]-4-biphenylyl]ethyl]carbamate (310 mg), ammonium formate (155 mg) and palladium on carbon powder (155 mg) in methanol (5 ml) and water (0.5 ml) was refluxed for 30 minutes. The catalyst was filtered off, and the filtrate was poured into water and extracted with chloroform-methanol (19:1). The organic layer was washed with brine, dried over magnesium sulfate, and evaporated to give pyridine product. To a solution of the product in ethyl acetate (1.8 ml) was added 4N hydrogen chloride in ethyl acetate (1.8 ml), and the mixture was stirred at room temperature for 16 hours. The resultant solid was collected by filtration and dried to give 4'-[2-[[(2R)-2-hydroxy-2-(3-pyridyl)ethyl]amino]-ethyl]-3-isobutyl-N-(methylsulfonyl)-4-biphenylcarboxamide dihydrochloride (93 mg).

NMR (DMSO-$d_6$, δ): 0.87 (6H, d, J=6.5 Hz), 1.77-1.87 (1H, m), 2.74 (2H, d, J=7.0 Hz), 3.06-3.37 (6H, m), 3.57 (3H, s), 5.22-5.25 (1H, m), 7.37-7.73 (8H, m), 7.82-7.89 (1H, m), 8.31-8.35 (1H, m), 8.77 (1H, d, J=4.3 Hz), 8.83 (1H, s), 9.14 (1H, br), 9.26 (1H, br), 12.2 (1H, br) MS (m/z): 494 (M−2HCl—H)⁻

EXAMPLE 53

The following compound was obtained according to a similar manner to that of Example 52.

3-(Cyclohexyloxy)-4'-2-[[(2R)-2-hydroxy-2-(3-pyridyl)-ethyl]amino]ethoxy]-N-(methylsulfonyl)-4-biphenylcarboxamide dihydrochloride NMR (DMSO-$d_6$, δ): 1.3-1.8 (8H, m), 1.9-2.0 (2H, m), 3.2-3.5 (4H, m), 3.4 (3H, s), 4.4 (2H, br), 4.8-4.9 (1H, m), 5.2-5.3 (1H, m), 6.2 (1H, m), 7.12 (2H, d, J=8.8 Hz), 7.3-7.4 (2H, m), 7.7-7.9 (4H, m), 8.34 (1H, d, J=8.1 Hz), 8.76-8.85 (2H, m), 9.3 (2H, br) MS (m/z): 552 (M−2HCl—H)⁻

EXAMPLE 54

To a solution of tert-butyl [2-[4'-formyl-3'-[isopropyl(methyl)amino]-4-biphenylyl]ethyl][(2R)-2-hydroxy-2-phenylethyl]carbamate (310 mg) in acetonitrile (3.5 ml) and pH 4 buffer solution (sodium dihydrogenphosphate) (1.6 ml) were added 30% hydrogen peroxide solution (60 μl) and 80% sodium chlorite (110 mg) below 10° C. The reaction mixture was stirred at 20° C. for 10 hours. The mixture was diluted with ethyl acetate, washed with water and brine, dried over magnesium sulfate and evaporated under reduced pressure. The residue was purified by column chromatography on silica gel (chloroform/methanol=15/1) to give a benzoic acid product (35 mg). To a solution of the product in ethyl acetate (0.5 ml) was added 4N hydrogen chloride in ethyl acetate (0.5 ml), and the mixture was stirred at room temperature for 12 hours. The resultant solid was collected by filtration and dried to give 4'-[2-[[(2R)-2-hydroxy-2-phenylethyl]amino]ethyl]-3-[isopropyl(methyl)amino]-4-biphenylcarboxylic acid dihydrochloride (23 mg).

NMR (DMSO-$d_6$, δ): 1.15 (6H, d, J=6.4 Hz), 2.98 (3H, s), 3.0-3.3 (6H, m), 3.61-3.74 (1H, m), 4.96-5.02 (1H, m), 7.31-7.50 (7H, m), 7.75-7.82 (3H, m), 8.05-8.15 (2H, m), 8.88 (1H, br), 9.21 (1H, br), 17.2 (1H, br) MS (m/z): 433 (M−2HCl+H)⁺

EXAMPLE 55

To a solution of methyl 2-amino-4'-[2-[(tert-butoxycarbonyl)[(2R)-2-hydroxy-2-phenylethyl]amino]ethyl]-4-biphenylcarboxylate (280 mg) in N,N-dimethylformamide (4 ml) was added methyl iodine (0.124 ml) and potassium carbonate (276 mg), and the mixture was stirred at 25° C. for 16 hours. The mixture was diluted with ethyl acetate and water. The organic layer was separated, washed with brine, dried over magnesium sulfate and evaporated under reduced pressure. The residue was purified by column chromatography on silica gel (hexane/ethyl acetate=3/1) to give methyl 4'-[2-[(tert-butoxycarbonyl)[(2R)-2-hydroxy-2-phenylethyl]amino]-ethyl]-2-(dimethylamino)-4-biphenylcarboxylate (125 mg).

MS (m/z): 519 (M+H)⁺

EXAMPLE 56

A solution of methyl 4'-(2-amino-2-methylpropyl)-3-isobutyl-4-biphenylcarboxylate (372 mg) and (2R)-2-phenyloxirane (142 mg) in ethanol (3.5 ml) was refluxed for 24 hours. The mixture was evaporated in vacuo. The residue was purified by column chromatography on silica gel (chloroform:methanol=10:1) to give an amino alcohol. To a solution of the product (280 mg) in methanol (5.0 ml) was added 1N aqueous sodium hydroxide solution (2.4 ml), and the mixture was stirred at 50° C. for 40 hours. The solvent was removed by evaporation. The pH of the residue was kept between 7 to 8 with 1N hydrochloric acid and extracted with chloroform-methanol (19:1) solution (30 ml×2). The combined organic layers were washed with water and brine, dried over magnesium sulfate and evaporated under reduced pressure to give a benzoic acid product. To a solution of the product in chloroform, methanol and ethyl acetate was added 4N hydrogen chloride in ethyl acetate (1.0 ml), and the mixture was stirred at room temperature for 2 minutes. The mixture was evaporated under reduced pressure to give 4'-[2-[[(2R)-2-hydroxy-2-phenylethyl]amino]-2-methylpropyl]-3-isobutyl-4-biphenylcarboxylic acid hydrochloride (70 mg).

NMR (DMSO-$d_6$, δ): 0.87 (6H, d, J=6.6 Hz), 1.26 (6H, s), 1.8-1.9 (1H, m), 2.92 (2H, d, J=7.0 Hz), 3.0-3.3 (2H, m), 3.06 (2H, s), 4.94-4.99 (1H, m), 6.34 (1H, br), 7.3-7.9 (12H, m) MS (m/z): 444 (M-HCl—H)⁻

EXAMPLE 57

To a solution of tert-butyl [(2R)-2-hydroxy-2-phenylethyl][2-(4-iodophenoxy)ethyl]carbamate (350 mg) in toluene (6.0 ml) and ethanol (1.5 ml) was added boric acid (222 mg), [1,1'-bis(diphenylphosphino)ferrocene]-dichlorobispalladium(II), complex with dichloromethane (59 mg), 1,1'-bis(diphenylphosphino)ferrocene (20 mg) and aqueous solution of sodium carbonate (2M, 0.8 ml), and the mixture was stirred at 75° C. for 4 hours under nitrogen. The mixture was partitioned between with ethyl acetate and water. The organic layer was separated, washed with brine, dried over magnesium sulfate and evaporated under reduced pressure. The residue was purified by column chromatography on silica gel (hexane/ethyl acetate=3/1) to give biphenyl product (285 mg). To a solution of the product in methanol (5.0 ml) was added 1N aqueous sodium hydroxide solution (1.5 ml), and the mixture was stirred at 40° C. for 3 hours. The solvent was removed by evaporation, and the aqueous solution was acidified with 1N hydrochloric acid and extracted with ethyl acetate. The combined organic layers were washed with water and brine, dried over magnesium sulfate and evaporated under reduced pressure to give a benzoic acid product. To a solution of the product in ethyl acetate (2.0 ml) was added 4N hydrogen chloride in ethyl acetate (2.0 ml), and the mixture was stirred at room temperature for 12 hours. The resultant solid was collected by filtration and dried to give 3-(cyclohexyloxy)-4'-[2-[[(2R)-2-hydroxy-2-phenylethyl]amino] ethoxy]-4-biphenylcarboxylic acid hydrochloride (210 mg).

NMR (DMSO-$d_6$, δ): 1.3-1.9 (10H, m), 3.0-3.3 (2H, m), 3.4 (2H, br), 4.4 (2H, t, J=5.0 Hz), 4.6-4.7 (2H, m), 4.9-5.0 (2H, m), 6.2 (1H, m), 7.1 (2H, d, J=8.8 Hz), 7.2-7.4 (7H, m), 7.67-7.73 (3H, m), 9.0 (2H, br) MS (m/z): 474 (M-HCl—H)$^-$

EXAMPLE 58

The following compounds were obtained according to a similar manner to that of Example 57.

(1) 4'-[2-[[(2R)-2-Hydroxy-2-phenylethyl]amino]ethoxy]-3-propoxy-4-biphenylcarboxylic acid hydrochloride NMR (DMSO-$d_6$, δ): 1.02 (3H, t, J=7.3 Hz), 1.7-1.8 (2H, m), 3.1-3.2 (2H, m), 3.4-3.5 (2H, m), 4.1 (2H, t, J=6.3 Hz), 4.3-4.4 (2H, m), 4.9-5.0 (1H, m), 6.2 (1H, br), 7.1 (2H, d, J=8.8 Hz), 7.2-7.4 (7H, m), 7.7-7.8 (3H, m) MS (m/z): 434 (M-HCl—H)$^-$ (2) 4'-[2-[[(2R)-2-(3-Chlorophenyl)-2-hydroxyethyl]amino]-ethoxy]-3-propoxy-4-biphenylcarboxylic acid hydrochloride NMR (DMSO-$d_6$, δ): 1.02 (3H, t, J=7.3 Hz), 1.67-1.85 (2H, m), 3.1-3.2 (2H, m), 3.4-3.5 (2H, m), 4.1 (2H, t, J=6.3 Hz), 4.3-4.4 (2H, m), 5.0-5.1 (1H, m), 6.3 (1H, br), 7.1 (2H, d, J=8.7 Hz), 7.2-7.3 (2H, m), 7.35-7.48 (4H, m), 7.7-7.8 (3H, m) MS (m/z): 468 (M-HCl—H)$^-$ (3) 4'-[2-[[(2R)-2-(3-Chlorophenyl)-2-hydroxyethyl]amino]-ethoxy]-3-(cyclohexyloxy)-4-biphenylcarboxylic acid hydrochloride NMR (DMSO-$d_6$, δ): 1.3-1.9 (10H, m), 3.1-3.2 (2H, m), 3.4-3.5 (2H, m), 4.3-4.4 (2H, m), 4.6 (1H, m), 5.0-5.1 (1H, m), 6.3 (1H, br), 7.1 (2H, d, J=8.7 Hz), 7.2-7.5 (6H, m), 7.69-7.74 (3H, m) MS (m/z): 508 (M-HCl—H)$^-$ (4) 4'-[2-[[(2R)-2-Hydroxy-2-phenylethyl]amino]ethoxy]-3-isopropoxy-4-biphenylcarboxylic acid hydrochloride NMR (DMSO-$d_6$, δ): 1.31 (6H, d, J=6.0 Hz), 3.0-3.3 (2H, m), 3.45 (2H, d, J=4.7 Hz), 4.38 (2H, t, J=4.8 Hz), 4.8-4.9 (1H, m), 4.9-5.0 (1H, m), 6.2 (1H, br), 7.1 (2H, d, J=8.8 Hz), 7.2-7.4 (7H, m), 7.67-7.74 (3H, m) MS (m/z): 434 (M-HCl—H)$^-$ (5) 4'-[2-[[(2R)-2-(3-Chlorophenyl)-2-hydroxyethyl]amino]-ethoxy]-3-isopropoxy-4-biphenylcarboxylic acid hydrochloride NMR (DMSO-$d_6$, δ): 1.31 (6H, d, J=6.0 Hz), 3.1-3.3 (2H, m), 3.4-3.5 (2H, m), 4.3-4.4 (2H, m), 4.8-4.9 (1H, m), 4.9-5.0 (1H, m), 6.3 (1H, br), 7.1 (2H, d, J=8.8 Hz), 7.2-7.5 (6H, m), 7.67-7.74 (3H, m) MS (m/z): 468 (M-HCl—H)$^-$ (6) 4'-[2-[[(2R)-2-Hydroxy-2-phenylethyl]amino]ethoxy]-3-isobutoxy-4-biphenylcarboxylic acid hydrochloride NMR (DMSO-$d_6$, δ): 1.02 (6H, d, J=6.7 Hz), 2.0-2.1 (1H, m), 3.0-3.3 (2H, m), 3.4-3.5 (2H, m), 3-0.92 (2H, d, J=6.4 Hz), 4.37 (2H, t, J=4.7 Hz), 5.0-5.1 (1H, m), 6.3 (1H, br), 7.1 (2H, d, J=88 Hz), 7.2-7.4 (7H, m), 7.7-7.8 (3H, m) MS (m/z): 448 (M-HCl—H)$^-$ (7) 4'-[2-[[(2R)-2-(3-Chlorophenyl)-2-hydroxyethyl]amino]-ethoxy]-3-isobutoxy-4-biphenylcarboxylic acid hydrochloride NMR (DMSO-$d_6$, δ): 1.02 (6H, d, J=6.6 Hz), 2.0-2.1 (1H, m), 3.0-3.2 (2H, m), 3.4-3.5 (2H, m), 3.92 (2H, d, J=6.4 Hz), 4.38 (2H, t, J=4.8 Hz), 4.9-5.0 (1H, m), 6.2 (1H, br), 7.1 (2H, d, J=8.8 Hz), 7.2-7.5 (6H, m), 7.7-7.8 (3H, m) MS (m/z): 482 (M-HCl—H)$^-$ (8) 3-Butoxy-4'-[2-[[(2R)-2-hydroxy-2-phenylethyl]amino]-ethoxy]-4-biphenylcarboxylic acid hydrochloride NMR (DMSO-$d_6$, δ): 0.94 (6H, d, J=7.2 Hz), 1.4-1.6 (2H, m), 1.7-1.8 (2H, m), 3.0-3.2 (2H, m), 3.4-3.5 (2H, m), 4.15 (2H, d, J=6.2 Hz), 4.37 (2H, t, J=4.7 Hz), 4.9-5.0 (1H, m), 6.2 (1H, br), 7.1 (2H, d, J=8.7 Hz), 7.2-7.4 (7H, m), 7.7-7.8 (3H, m) MS (m/z): 448 (M-HCl—H)$^-$ (9) 3-Butoxy-4'-[2-[[(2R)-2-(3-chlorophenyl)-2-hydroxyethyl]amino]ethoxy]-4-biphenylcarboxylic acid hydrochloride NMR (DMSO-$d_6$, δ): 0.94 (6H, d, J=7.2 Hz), 1.4-1.6 (2H, m), 1.7-1.8 (2H, m), 3.0-3.2 (2H, m), 3.4-3.5 (2H, m), 4.15 (2H, d, J=6.2 Hz), 4.37 (2H, t, J=4.7 Hz), 4.9-5.0 (1H, m), 6.2 (1H, br), 7.1 (2H, d, J=8.7 Hz), 7.2-7.5 (6H, m), 7.7-7.8 (3H, m) MS (m/z): 482 (M-HCl—H)$^-$

(10) 4'-[[2-[[(2R)-2-(3-Chlorophenyl)-2-hydroxyethyl]amino]-ethyl]amino]-4-biphenylcarboxylic acid hydrochloride NMR (DMSO-$d_6$, δ): 3.1-3.3 (4H, m), 3.4-3.5 (2H, m) 4.9-5.0 (1H, m), 6.77 (2H, d, J=8.6 Hz), 7.3-7.6 (7H, m), 7.56 (2H, d, J=8.6 Hz), 7.73-7.84 (2H, m), 8.33 (1H, s), 8.9 (1H, br), 9.2 (1H, br) MS (m/z): 409 (M-HCl—H)$^-$

(11) 4'-[[2-[[(2R)-2-(3-Chlorophenyl)-2-hydroxyethyl]amino]-ethyl]amino]-3-biphenylcarboxylic acid hydrochloride NMR (DMSO-$d_6$, δ): 3.0-3.3 (4H, m), 3.5-3.6 (2H, m), 4.9-5.0 (1H, m), 6.2 (1H, br), 6.76 (2H, d, J=8.6 Hz), 7.3-7.5 (4H, m), 7.56 (2H, d, J=8.6 Hz), 7.70 (2H, d, J=8.4 Hz), 7.92 (1H, s), 7.94 (2H, d, J=8.4 Hz), 8.8 (1H, br), 9.2 (1H, br) MS (m/z): 409 (M-HCl—H)$^-$

(12) 4'-[[2-[[(2R)-2-(3-Chlorophenyl)-2-hydroxyethyl]amino]-ethyl]amino]-3-propoxy-4-biphenylcarboxylic acid hydrochloride NMR (DMSO-$d_6$, δ): 1.02 (3H, d, J=7.3 Hz), 1.67-1.85 (2H, m), 3.0-3.3 (4H, m), 3.4-3.5 (2H, m), 4.09 (2H, t, J=6.3 Hz), 4.95-5.05 (1H, m), 6.77 (2H, d, J=8.6 Hz), 7.25 (1H, d, J=7.7 Hz), 7.29 (1H, s), 7.3-7.7 (7H, m), 8.9 (1H, br), 9.2 (1H, br) MS (m/z): 503 (M–H)$^-$

(13) 4'-[2-[[(2R)-2-(4-Chlorophenyl)-2-hydroxyethyl]amino]-ethoxy]-3-propoxy-4-biphenylcarboxylic acid hydrochloride NMR (DMSO-$d_6$, δ): 1.02 (3H, t, J=7.3 Hz), 1.67-1.85 (2H, m), 3.1-3.3 (2H, m), 3.4-3.5 (2H, m), 4.1 (2H, t, J=6.4 Hz), 4.3-4.4 (2H, m), 5.0-5.1 (1H, m), 6.3 (1H, br), 7.1 (2H, d, J=8.7 Hz), 7.2-7.3 (2H, m), 7.4-7.5 (4H, m), 7.7-7.8 (3H, m), 9.0 (2H, br) MS (m/z): 468 (M-HCl—H)$^-$

(14) 3-(Cyclohexylamino)-4'-[2-[[(2R)-2-hydroxy-2-phenylethyl]amino]ethoxy]-4-biphenylcarboxylic acid hydrochloride NMR (DMSO-$d_6$, δ): 1.2-1.7 (8H, m), 1.9-2.0 (2H, m), 3.1-3.3 (2H, m), 3.4-3.5 (2H, m), 3.6-3.7 (1H, m), 4.3-4.4 (2H, m), 5.0-5.1 (1H, m), 6.7-6.8 (1H, m), 6.9 (1H, s), 7.09 (2H, d, J=8.7 Hz), 7.3-7.4 (5H, m), 7.66 (2H, d, J=8.7 Hz), 7.83 (1H, d, J=8.3 Hz), 8.98 (1H, br), 9.23 (1H, br) MS (m/z): 473 (M–2HCl—H)$^-$

EXAMPLE 59

To a suspension of 4'-(2-aminoethoxy)-3-(cyclohexyloxy)-N-(methylsulfonyl)-4-biphenylcarboxamide hydrochloride (620 mg) in Methanol (6.2 ml) was added 1N aqueous sodium hydroxide solution (1.6 ml). The mixture was stirred at room temperature for 30 minutes and evaporated under reduced pressure. Under nitrogen at room temperature, to a mixture of the resultant solid in dimethyl sulfoxide (7 ml) was added bis(trimethylsilyl)urea (324 mg), and the mixture was stirred at 65° C. for 1 hour. To the mixture was added 2-chloro-5-[(2R)-2-oxiranyl]pyridine (310 mg) and the mixture was stirred at 65° C. for 18 hours. The resulting mixture was cooled to room temperature and 1N hydrochloric acid (6.0 ml) was added. After being stirred for 20 minutes, the mixture was neutralized with saturated aqueous sodium bicarbonate (6.0 ml) and the aqueous mixture was extracted with ethyl acetate. The organic layer was washed successively with water and brine, dried over anhydrous magnesium sulfate and evaporated under reduced pressure. To a solution of the product in tetrahydrofuran (10 ml) and water (8 ml) was added di-tert-butyl dicarbonate (580 mg) at room temperature. The pH was kept between 7 to 8 by using 1N aqueous sodium hydroxide solution. The mixture was stirred at room temperature for 1 hour. The mixture was partitioned between ethyl acetate and water. The organic layer was separated, washed with brine, dried over magnesium sulfate and evaporated under reduced pressure. The residue was purified by column chromatography on silica gel (hexane/ethyl acetate=6/4-5/5) to give tert-butyl [(2R)-2-(6-chloro-3-pyridyl)-2-hydroxyethyl][2-[[3'-(cyclohexyloxy)-4'-[[(methylsulfonyl)amino]carbonyl]-4-biphenylyl]oxy]-ethyl]carbamate (360 mg).

MS (m/z): 686 (M−H)−

EXAMPLE 60

The following compound was obtained according to a similar manner to that of Example 44.
(1) tert-Butyl [3-[3'-[cyclohexyloxy]-4'-[[(methylsulfonyl)amino]carbonyl]-4-biphenylyl]propyl]-[(2R)-2-hydroxy-2-phenylethyl]carbamate
(+)ESI-MS (m/z): 673 (M+Na)+
(2) tert-Butyl [3-[3'-ethoxy-4'-[[(methylsulfonyl)amino]-carbonyl]-4-biphenylyl]propyl][(2R)-2-hydroxy-2-phenylethyl]carbamate
(−)ESI-MS (m/z): 595 (M−H)−
(3) tert-Butyl [(2R)-2-hydroxy-2-phenylethyl][3-[3'-isobutyl-4'-[[(methylsulfonyl)amino]carbonyl]-4-biphenylyl]propyl]carbamate
(+)ESI-MS (m/z): 631 (M+Na)+
(4) tert-Butyl [3-[3'-cyclopentyl-4'-[[(methylsulfonyl)-amino]carbonyl]-4-biphenylyl]propyl][(2R)-2-hydroxy-2-phenylethyl]carbamate
(+)ESI-MS (m/z): 643 (M+Na)+
(5) Ethyl [4'-2-[(tert-butoxycarbonyl)[(2R)-2-hydroxy-2-phenylethyl]amino]ethyl]-3-cyclohexyloxy-4-biphenylyl]-acetate
(+)ESI-MS (m/z): 624 (M+Na)+
(6) Ethyl [4'-[2-[(tert-butoxycarbonyl)[(2R)-2-hydroxy-2-(3-pyridyl)ethyl]amino]ethyl]-3-(cyclohexyloxy-4-biphenylyl]acetate
(+)ESI-MS (m/z): 625 (M+Na)+
(7) tert-Butyl [(2R)-2-hydroxy-2-phenylethyl][3-[3'-isopropoxy-4'-[[(methylsulfonyl)amino]carbonyl]-4-biphenylyl]propyl]carbamate
(−)ESI-MS (m/z): 609 (M−H)−

EXAMPLE 61

The following compounds were obtained according to a similar manner to that of Example 1 followed by a similar manner to that of Example 52.
(1) 3-Cyclopentyl-4'-[2-[[(2R)-2-hydroxy-2-(3-pyridyl)ethyl]amino]ethyl]-N-(methylsulfonyl)-4-biphenylcarboxamide dihydrochloride NMR (DMSO-$d_6$, δ): 1.65-1.81 (6H, m), 1.99-2.05 (2H, m), 3.06-3.36 (7H, m), 3.40 (3H, s), 5.24-5.28 (1H, m), 7.37-7.71 (8H, m), 7.88-7.95 (1H, m), 8.38-8.42 (1H, m), 8.80 (1H, d, J=4.3 Hz), 8.86 (1H, s), 9.20 (1H, br), 9.33 (1H, br), 12.2 (1H, br) MS (m/z): 507 (M−2HCl—H)−
(2) 3-(Cyclohexylthio)-4'-[2-[[(2R)-2-hydroxy-2-(3-pyridyl)ethyl]amino]ethyl]-N-(methylsulfonyl)-4-biphenyl-carboxamide dihydrochloride NMR (DMSO-$d_6$, δ): 1.14-1.99 (10H, m), 3.06-3.46 (6H, m), 3.4 (3H, s), 5.21 (1H, d, J=6.2 Hz), 7.41 (2H, d, J=8.1 Hz), 7.56-7.86 (6H, m), 8.3 (1H, d, J=8 Hz), 8.76 (1H, d, J=4.9 Hz), 9.21 (1H, s) (−)ESI-MS (m/z): 552 (M−H)−
(3) 3-(Cyclohexylamino)-4'-[2-[[(2R)-2-hydroxy-2-(3-pyridyl)ethyl]amino]ethyl]-N-(methylsulfonyl)-4-biphenyl-carboxamide dihydrochloride NMR (DMSO-$d_6$, δ): 1.61-1.67 (8H, m), 1.91-1.99 (2H, m), 2.99-3.48 (6H, m), 3.55-3.72 (1H, m), 6.84 (1H, d, J=8.4 Hz), 6.97 (1H, s), 7.38 (2H, d, J=8.2 Hz), 7.69 (2H, d, J=8.1 Hz), 7.82 (1H, d, J=8.4 Hz), 8.08 (1H, dd, J=5.7, 8.1 Hz), 8.61 (1H, d, J=8.2 Hz), 8.89 (1H, d, J=5.5 Hz), 8.95 (1H, s), 9.34 (2H, br s) (−)ESI-MS (m/z): 535 (M−H)−
(4) 4'-[2-[[(2R)-2-Hydroxy-2-(3-pyridyl)ethyl]amino]-ethyl]-3-(isopropylthio)-N-(methylsulfonyl)-4-biphenyl-carboxamide dihydrochloride NMR (DMSO-$d_6$, δ): 1.26 (6H, d, J=6.6 Hz), 2.99-3.75 (10H, m), 4.93-5.08 (1H, m), 6.33 (1H, br s), 7.36-7.45 (4H, m), 7.58 (1H, s), 7.69 (3H, d, J=7.5 Hz), 8.01 (1H, d, J=8.4 Hz), 8.55 (1H, dd, J=1.5, 4.8 Hz), 8.62 (1H, d, J=1.7 Hz) (−)ESI-MS (m/z): 512 (M−H)−

EXAMPLE 62

To a solution of tert-butyl (3-(4-bromophenyl)propyl]-[(2R)-2-hydroxy-2-(4-nitorphenyl)ethyl]carbamate (206 mg), [3-[cyclohexyloxy]-4-[[(methylsulfonyl)amino]carbonyl]-phenyl]boronic acid (220 mg), [1,1'-bis(diphenylphosphino)ferrocene]dichloropalladium(II) (47.1 mg) and 1,1'-bis(diphenylphosphino)ferrocene (11.9 mg) in N,N-dimethylformamide was added 2.0M aqueous sodium carbonate solution (1.10 ml). The mixture was stirred at 90° C. for 2 hours. After cooling to room temperature, the reaction mixture was partitioned between ethyl acetate and 0.1N hydrochloric acid and the organic layer was separated, washed with water and brine and dried over magnesium sulfate. Filtration followed by evaporation under reduced pressure gave a crude product which was purified by column chromatography on silica gel (eluent: hedxane/ethyl acetate=1.5/1) to give tert-butyl [3-[3'-[cyclohexyloxy]-4'-[[(methylsulfonyl)amino]carbonyl]-4-biphenylyl]propyl] [(2R)-2-hydroxy-2-(4-nitrophenyl)ethyl]carbamate (205 mg) as a white solid (foam).

(−)ESI-MS (m/z): 694 (M−H)−

EXAMPLE 63

The following compounds were obtained according to a similar manner to that of Example 62.

(1) tert-Butyl [(2R)-2-hydroxy-2-(4-nitrophenyl)ethyl][3-[3'-isopropoxy-4'-[[(methylsulfonyl)amino]carbonyl]-4-biphenylyl]propyl]carbamate
(−)ESI-MS (m/z): 654 (M−H)⁻
(2) tert-Butyl [(2R)-2-hydroxy-2-(4-nitrophenyl)ethyl][3-[3'-isobutyl-4'-[[(methylsulfonyl)amino]carbonyl]-4-biphenylyl]propyl]carbamade
(−)ESI-MS (m/z): 652 (M−H)⁻
(3) tert-Butyl [3-[3'-cyclopentyl-4'-[[(methylsulfonyl)-amino]carbonyl]-4-biphenylyl]propyl][(2R)-2-hydroxy-2-(4-nitorphenyl)ethyl]carbamade
(−)ESI-MS (m/z): 664 (M−H)⁻

EXAMPLE 64

A mixture of tert-butyl [3-[3'-(cyclohexyloxy)-4'-[[(methylsulfonyl)amino]carbonyl]-4-biphenylyl]propyl][(2R)-2-hydroxy-2-(4-nitrophenyl)ethyl]carbamate (200 mg), iron powder (48.2 mg) and ammonium chloride (7.7 mg) in water (1.0 ml) and ethanol (3.0 ml) was stirred 80° C. for 1 hour. After cooling to room temperature, ethyl acetate (15 ml) was added to the reaction mixture and iron powder was removed by filtration through a Celite cake. The filtrate was washed with water and brine and dried over magnesium sulfate. Filtration followed by evaporation under reduced pressure gave a crude product which was purified by column chromatography on silica gel (eluent: hexane/ethyl acetate=1/1) to give tert-butyl [(2R)-2-(4-aminophenyl)-2-hydroxyethyl][3-[3'-[cyclohexyloxy]-4'-[[(methylsulfonyl)-amino]carbonyl]-4-biphenylyl]propyl]carbamate (129 mg) as a white solid (foam).
(−)ESI-MS (m/z): 664 (M−H)⁻

EXAMPLE 65

The following compounds were obtained according to a similar manner to that of Example 64.
(1) tert-Butyl [(2R)-2-(4-aminophenyl)-2-hydroxyethyl][3-[3'-isopropoxy-4'-[[(methylsulfonyl)amino]carbonyl]-4-biphenylyl]propyl]carbamate
(−)ESI-MS (m/z): 624 (M−H)⁻
(2) tert-Butyl [(2R)-2-(4-aminophenyl)-2-hydroxyethyl][3-[3'-isobutyl-4'-[[(methylsulfonyl)amino]carbonyl]-4-biphenylyl]propyl]carbamate
(−)ESI-MS (m/z): 622 (M−H)⁻
(3) tert-Butyl [(2R)-2-(4-aminophenyl)-2-hydroxyethyl][3-[3'-cyclopentyl-4'-[[(methylsulfonyl)amino]carbonyl]-4-biphenylyl]propyl]carbamate
(−)ESI-MS (m/z): 634 (M−H)⁻

EXAMPLE 66

The following compounds were obtained according to a similar manner to that of Example 1 followed by a similar manner to that of Example 4.
(1) 4'-[2-[[(2R)-2-Hydroxy-2-phenylethyl]amino]ethyl]-3-(tetrahydro-2H-pyran-4-yloxy)-4-biphenylcarboxylic acid hydrochloride
NMR (DMSO-d₆, δ): 1.55-1.71 (2H, m), 1.9-2.00 (2H, m), 3.0-3.54 (6H, m), 3.8-3.93 (2H, m), 4.8-5.0 (2H, m), 6.4 (1H, br), 7.26-7.41 (9H, m), 7.69-7.74 (3H, m), 8.9 (1H, br) MS (m/z): 460 (M-HCl—H)⁻
(2) 3-(Ethoxymethyl)-4'-[2-[[(2R)-2-hydroxy-2-phenylethyl]-amino]ethyl]-4-biphenylcarboxylic acid hydrochloride
NMR (DMSO-d₆, δ): 1.20 (3H, t, J=7.0 Hz), 3.05-3.39 (6H, m), 3.59 (2H, q, J=7.0 Hz), 4.96-5.00 (1H, m), 4.86 (2H, s), 6.21 (1H, br), 7.31-7.42 (7H, m), 7.63-7.7 (3H, m), 7.85-7.96 (2H, m) MS (m/z): 418 (M-HCl—H)⁻
(3) 4'-[2-[[(2R)-2-Hydroxy-2-phenylethyl]amino]ethyl]-3-vinyl-4-biphenylcarboxylic acid hydrochloride
NMR (DMSO-d₆, δ): 3.00-3.32 (6H, m), 4.96-5.00 (1H, m), 5.40 (1H, dd, J=12.2, 1.0 Hz), 5.89 (1H, dd, J=17.4, 1.0 Hz), 6.21 (1H, br), 7.30-7.93 (13H, m), 9.10 (1H, br) MS (m/z): 386 (M-HCl—H)⁻
(4) 4'-[2-[[(2R)-2-Hydroxy-2-phenylethyl]amino]ethyl]-3-(2-methyl-1-propen-1-yl)-4-biphenylcarboxylic acid hydrochloride
NMR (DMSO-d₆, δ): 1.40 (6H, s), 3.02-3.26 (6H, m), 4.96-5.00 (1H, m), 6.22 (1H, br), 7.31-7.34 (1H, m), 7.38-7.41 (7H, m), 7.68-7.76 (4H, m), 7.98-8.00 (1H, m), 8.9 (1H, br), 9.16 (1H, br) MS (m/z): 414 (M-HCl—H)⁻
(5) 4'-[2-[[(2R)-2-Hyxroxy-2-phenylethyl]amino]ethyl]-3-(trifluoromethyl)-4-biphenylcarboxylic acid hydrochloride
NMR (DMSO-d₆, δ): 3.0-3.3 (6H, m), 4.96-5.00 (1H, m), 6.22 (1H, br), 7.31-7.44 (7H, m), 7.78 (2H, d, J=8.1 Hz), 7.92 (1H, d, J=7.8 Hz), 8.05 (2H, d, J=7.7 Hz), 9.0 (1H, br) MS (m/z): 428 (M-HCl—H)⁻
(6) 4'-[2-[[(2R)-2-(3-Chlorophenyl)-2-hydroxyethyl]amino]-ethyl]-3-isobutyl-4-biphenylcarboxylic acid hydrochloride
NMR (DMSO-d₆, δ): 0.88 (6H, d, J=6.6 Hz), 1.79-1.92 (1H, m), 2.92 (2H, d, J=7.0 Hz), 3.02-3.32 (6H, m), 5.00 (1H, br), 6.34 (1H, br), 7.36-7.89 (11H, m), 9.0 (1H, br) MS (m/z): 450 (M-HCl—H)⁻
(7) 4'-[2-[[(2R)-2-(3-Chlorophenyl)-2-hydroxyethyl]amino]-ethyl]-3-vinyl-4-biphenylcarboxylic acid hydrochloride NMR (DMSO-d₆, δ): 3.01-3.32 (6H, m), 4.97-5.00 (1H, m), 5.40 (1H, dd, J=11.0, 1.0 Hz), 5.89 (1H, dd, J=17.4, 1.0 Hz), 6.34 (1H, br), 7.37-7.92 (13H, m), 9.10 (1H, br) MS (m/z): 420 (M-HCl—H)⁻
(8) 4'-[2-[[(2R)-2-(3-Chlorophenyl)-2-hydroxyethyl]amino]-ethyl]-3-(trifluoromethyl)-4-biphenylcarboxylic acid hydrochloride
NMR (DMSO-d₆, δ): 3.0-3.3 (6H, m), 4.9-5.0 (1H, m), 6.36 (1H, br), 7.35-7.47 (6H, m), 7.78 (2H, d, J=8.1 Hz), 7.91 (1H, d, J=7.9 Hz), 8.05 (2H, d, J=7.7 Hz), 9.0 (1H, br) MS (m/z): 462 (M-HCl—H)⁻
(9) 4'-[2-[[(2R)-2-(3-Chlorophenyl)-2-hydroxyethyl]amino]-ethyl]-2-ethyl-4-biphenylcarboxylic acid hydrochloride
NMR (DMSO-d₆, δ): 1.05 (3H, t, J=7.5 Hz), 2.60 (2H, q, J=7.5 Hz), 3.0-3.3 (6H, m), 4.98-5.02 (1H, m), 6.35 (1H, br), 7.23-7.48 (9H, m), 7.76-7.91 (2H, m) MS (m/z): 422 (M-HCl—H)⁻
(10) 4'-[2-[[(2R)-2-(3-Chlorophenyl)-2-hydroxyethyl]amino]-ethyl]-2-ethoxy-4-biphenylcarboxylic acid hydrochloride
NMR (DMSO-d₆, δ): 1.29 (3H, t, J=6.9 Hz), 3.0-3.3 (6H, m), 4.1 (2H, q, J=6.9 Hz), 4.9-5.0 (1H, m), 6.3 (1H, br), 7.30-7.63 (11H, m) MS (m/z): 438 (M-HCl—H)⁻
(11) 4'-[2-[[(2R)-2-(3-Chlorophenyl)-2-hydroxyethyl]amino]-ethyl]-2-propyl-4-biphenylcarboxylic acid hydrochloride
NMR (DMSO-d₆, δ): 0.75 (3H, t, J=7.1 Hz), 1.38-1.50 (2H, m), 2.58 (2H, t, J=7.2 Hz), 3.0-3.3 (6H, m), 4.96-5.00 (1H, m), 6.33 (1H, br), 7.23-7.48 (9H, m), 7.78-7.89 (2H, m) MS (m/z): 436 (M-HCl—H)⁻
(12) 4'-[2-[[(2R)-2-Hydroxy-2-phenylethyl]amino]ethyl]-2-propyl-4-biphenylcarboxylic acid hydrochloride

(13) 3-(2-Furyl)-4'-[2-[[(1S,2R)-2-hydroxy-1-methyl-2-phenylethyl]amino]ethyl]-4-biphenylcarboxylic acid hydrochloride NMR (DMSO-$d_6$, δ): 0.97 (3H, d, J=6.6 Hz), 3.07-3.14 (2H, m), 3.32-3.48 (3H, m), 5.20 (1H, br), 6.14 (1H, br), 6.60-6.63 (1H, m), 6.88 (1H, d, J=3.5 Hz), 7.26-7.46 (7H, m), 7.66-7.79 (5H, m), 7.89 (1H, br), 8.91 (1H, br) MS (m/z): 440 (M-HCl—H)$^-$

(14) 3-Ethoxy-4'-[2-[[(2R)-2-hydroxy-2-phenylethyl]amino]-ethyl]-2-methyl-4-biphenylcarboxylic acid hydrochloride NMR (DMSO-$d_6$, δ): 1.33 (3H, t, J=6.9 Hz), 2.13 (3H, s), 2.98-3.3 (6H, m), 3.96 (2H, q, J=6.9 Hz), 4.96-5.00 (1H, m), 6.22 (1H, br), 7.02 (1H, d, J=8.0 Hz), 7.30-7.42 (9H, m), 7.56 (1H, d, J=8.0 Hz) MS (m/z): 418 (M-HCl—H)$^-$

(15) 4'-[2-[[(2R)-2-Hydroxy-2-phenylethyl]amino]ethyl]-3-(2-pyridyl)-4-biphenylcarboxylic acid dihydrochloride NMR (DMSO-$d_6$, δ): 3.00-3.26 (6H, m), 4.93-5.0 (1H, m), 6.21 (1H, br), 7.1-7.5 (8H, m), 7.6-7.7 (1H, m), 7.7-8.0 (5H, m), 8.14 (1H, br), 8.73 (1H, br), 8.84 (1H, br), 9.08 (1H, br) MS (m/z): 437 (M—2HCl—H)$^-$

(16) 4'[3-[[(2R)-2-(3-Chlorophenyl)-2-hydroxyethyl]amino]-propyl]-3-propoxy-4-biphenylcarboxylic acid hydrochloride NMR (DMSO-$d_6$, δ): 1.02 (3H, t, J=7.3 Hz), 1.7-1.8 (2H, m), 1.9-2.1 (2H, m), 2.7 (2H, t, J=7.3 Hz), 2.9-3.2 (4H, m), 4.1 (2H, t, J=6.3 Hz), 4.9-5.0 (1H, m), 6.3 (1H, br), 7.2-7.5 (8H, m), 7.67-7.73 (3H, m), 8.9 (2H, br) MS (m/z): 466 (M-HCl—H)$^-$

(17) 4'-[2-[[(1S,2R)-2-Hydroxy-1-methyl-2-phenylethyl]-amino]ethoxy]-3-isopropoxy-4-biphenylcarboxylic acid hydrochloride NMR (DMSO-$d_6$, δ): 1.0 (3H, d, J=6.7Hz), 1.3 (6H, t, J=6.0 Hz), 3.4-3.6 (3H, m), 4.4 (2H, t, J=5.0 Hz), 4.7-4.9 (1H, m), 5.2 (1H, br), 6.1 (1H, br), 7.1-7.4 (9H, m), 7.7 (3H, t, J=8.3 Hz), 9.0 (2H, br) MS (m/z): 448 (M-HCl—H)$^-$

(18) 4'-[2-[[(1S,2R)-2-Hydroxy-1-methyl-2-phenylethyl]amino]ethoxy]-3-isobutyl-4-biphenylcarboxylic acid hydrochloride NMR (DMSO-$d_6$, δ): 0.88 (3H, d, J=6.6 Hz), 1.7-1.9 (1H, m), 2.91 (6H, d, J=6.9 Hz), 3.5-3.6 (2H, m), 4.4 (2H, t, J=5.0 Hz), 5.2 (1H, br), 6.1 (1H, br), 7.13 (2H, d, J=8.8 Hz), 7.2-7.4 (5H, m), 7.5-7.6 (2H, m), 7.72 (2H, d, J=8.8 Hz), 7.86 (1H, d, J=8.8 Hz), 8.9 (−2H, br) MS (m/z): 446 (M-HCl—H)$^-$

(19) 4'-[2-[[(2R)-2-Hydroxy-2-phenylethyl]amino]ethoxy]-3-isobutyl-4-biphenylcarboxylic acid hydrochloride NMR (DMSO-$d_6$, δ): 0.88 (6H, d, J=6.6 Hz), 1.8-1.9 (1H, m), 2.89 (2H, d, J=6.9 Hz), 3.04-3.25 (2H, m), 3.45 (2H, m), 4.3-4.4 (2H, m), 4.9-5.0 (1H, m), 6.2 (1H, br), 7.1 (2H, d, J=8.8 Hz), 7.3-7.6 (7H, m), 7.71 (2H, d, J=8.7 Hz), 7.85 (1H, d, J=8.1 Hz) MS (m/z): 432 (M-HCl—H)$^-$

(20) 4'-[2-[[(2R)-2-(3-Chlorophenyl)-2-hydroxyethyl]amino]-ethoxy]-3-isobutyl-4-biphenylcarboxylic acid hydrochloride NMR (DMSO-$d_6$, δ): 0.88 (6H, d, J=6.6 Hz), 1.8-1.9 (1H, m), 2.9 (2H, d, J=6.9 Hz), 3.0-3.2 (2H, m), 3.4-3.5 (2H, m), 4.3-4.4 (2H, m), 5.0-5.1 (1H, m), 6.35 (1H, br), 7.1 (2H, d, J=8.7 Hz), 7.3-7.6 (6H, m), 7.71 (2H, d, J=8.7 Hz), 7.85 (1H, d, J=8.1 Hz) MS (m/z): 466 (M-HCl—H)$^-$

(21) 3-Ethoxy-4'-[2-[[(1S,2R)-2-hydroxy-1-methyl-2-phenylethyl]amino]ethyl]-4-biphenylcarboxylic acid hydrochloride NMR (DMSO-$d_6$, δ): 0.96 (3H, d, J=6.6 Hz), 1.36 (3H, t, J=6.8 Hz), 3.0-3.7 (5H, m), 4.22 (2H, q, J=6.8 Hz), 5.19 (1H, m), 6.20 (1H, m), 7.1-7.8 (12H, m) MS (m/z): 420 (M+H)

(22) 4'-[2-[[(1S,2R)-2-Hydroxy-1-methyl-2-phenylethyl]amino]ethyl]-3-propoxy-4-biphenylcarboxylic acid hydrochloride NMR (DMSO-$d_6$, δ): 0.8-1.1 (6H, m), 1.6-1.9 (2H, m), 3.0-3.7 (5H, m), 4.11 (2H, q, J=6.8 Hz), 5.24 (1H, m), 6.16 (1H, m), 7.1-7.8 (12H, m) MS (m/z): 434 (M+H)

(23) 3-(2-Ethoxyethoxy)-4'-[2-[[(1S,2R)-2-hydroxy-1-methyl-2-phenylethyl]amino]ethyl]-4-biphenylcarboxylic acid hydrochloride NMR (DMSO-$d_6$, δ): 0.96 (3H, d, J=6.6 Hz), 1.24 (3H, t, J=5.6 Hz), 3.0-3.8 (9H, m), 4.22 (2H, q, J=6.8 Hz), 5.19 (1H, m), 6.20 (1H, m), 7.1-7.8 (12H, m) MS (m/z): 464 (M+H)

(24) 3-(Cyclohexyloxy)-4'-[(2S)-3-hydroxy-2-[[(2R)-2-hydroxy-2-phenylethyl]amino]propyl]-4-biphenylcarboxylic acid hydrochloride NMR (DMSO-$d_6$, δ): 1.1-2.2 (10H, m), 3.0-3.7 (5H, m), 4.62 (2H, m), 5.19 (1H, m), 6.20 (1H, m), 7.1-7.8 (12H, m) MS (m/z): 490 (M+H)

(25) 4'-[2-[[(2R)-2-Hydroxy-2-phenylethyl]amino]-2-methylpropyl]-3-isopropoxy-4-biphenylcarboxylic acid hydrochloride NMR (DMSO-$d_6$, δ): 1.2-1.4 (12H, m), 3.0-3.7 (4H, m), 4.82 (1H, m), 5.19 (1H, m), 6.20 (1H, m), 7.1-7.8 (12H, m) MS (m/z): 448 (M+H)

(26) 4'-[3-[[(2R)-2-Hydroxy-2-phenylethyl]amino]propyl]-3-isopropoxy-4-biphenylcarboxylic acid hydrochloride NMR (DMSO-$d_6$, δ): 1.29 (6H, d, J=6.0 Hz), 1.7-2.2 (2H, m), 2.7-3.4 (6H, m), 4.78 (1H, m), 4.93 (1H, m), 6.17 (1H, m), 7.1-7.8 (12H, m) MS (m/z): 434 (M+H)

(27) 4'[2-[[(1S,2R)-2-Hydroxy-2-(4-hydroxyphenyl)-1-methylethyl]amino]ethoxy]-3-isopropoxy-4-biphenylcarboxylic acid hydrochloride NMR (DMSO-$d_6$, δ): 1.09 (3H, d, J=6.2 Hz), 1.33 (3H, d, J=6.0 Hz), 3.0-3.4 (2H, m), 4.2-4.4 (2H, m), 4.81 (1H, m), 5.06 (1H, m), 5.98 (1H, m), 6.35 (2H, m, J=8.4 Hz), 7.0-7.5 (6H, m), 7.6-7.8 (3H, m) MS (m/z): 466 (M+H)

(28) 3-Ethoxy-4'-[2-[[(1S,2R)-2-hydroxy-2-(4-hydroxyphenyl)-1-methylethyl]amino]ethyl]-4-biphenylcarboxylic acid hydrochloride NMR (DMSO-$d_6$, δ): 1.00 (3H, d, J=6.6 Hz), 1.33 (3H, t, J=6.8 Hz), 3.0-3.7 (5H, m), 4.20 (2H, q, J=6.8 Hz), 5.12 (1H, m), 5.98 (1H, m), 6.79 (2H,d, J=8.4 Hz), 7.1-7.6 (6H, m), 7.7-7.9 (3H, m) MS (m/z): 436 (M+H)

(29) 4'-[2-[[(1S,2R)-2-Hydroxy-2-(4-hydroxyphenyl)-1-methylethyl]amino]ethyl]-3-propoxy-4-biphenylcarboxylic acid hydrochloride NMR (DMSO-$d_6$, δ): 0.8-1.1 (6H, m), 1.6-1.9 (2H, m), 3.0-3.7 (5H, m), 4.11 (2H, q, J=6.8 Hz), 5.10 (1H, m), 5.99 (1H, m), 6.72 (2H, d, J=8.4 Hz), 7.1-7.4 (6H, m), 7.5-7.8 (3H, m) MS (m/z): 449 (M+H)

(30) 4'-[2-[[(1S,2R)-2-Hydroxy-2-(4-hydroxyphenyl)-1-methylethyl]amino]ethyl]-3-isopropoxy-4-biphenylcarboxylic acid hydrochloride NMR (DMSO-$d_6$, δ): 0.96 (3H, d, J=6.6 Hz), 1.30 (6H, d, J=5.9 Hz), 3.0-3.7 (5H, m), 4.76 (1H, m), 5.08 (1H, m), 5.99 (1H, m), 6.72 (2H, d, J=8.4 Hz), 7.1-7.4 (6H, m), 7.6-7.8 (3H, m) MS (m/z) 450 (M+H)

(31) 4'-[2-[[(1S,2R)-2-Hydroxy-2-(4-hydroxyphenyl)-1-methylethyl]amino]ethyl]-3-isobutoxy-4-biphenylcarboxylic acid hydrochloride NMR (DMSO-$d_6$, δ): 0.96 (3H, d, J=6.6 Hz), 1.10 (6H, d, J=5.9 Hz), 2.0 (1H, m), 3.0-3.7 (5H, m), 3.99 (2H, m), 5.05 (1H, m), 5.99 (1H, m), 6.72 (2H, d, J=8.4 Hz), 7.1-7.4 (6H, m), 7.6-7.8 (3H, m) MS (m/z): 464 (M+H)

(32) 3-(Cyclohexyloxy)-4'-[2-[[(1S,2R)-2-hydroxy-2-(4-hydroxyphenyl)-1-methylethyl]amino]ethyl]-4-biphenylcarboxylic acid hydrochloride NMR (DMSO-$d_6$, δ): 1.2-2.0 (10H, m), 3.0-3.7 (5H, m), 4.64 (1H, m), 5.09 (1H, m), 5.99 (1H, m), 6.72 (2H, d, J=8.4 Hz), 7.1-7.4 (6H, m), 7.6-7.8 (3H, m) MS (m/z): 490 (M+H)

(33) 4'-[3-[[(2R)-2-Hydroxy-2-(3-pyridyl)ethyl]amino]-propyl]-3-propoxy-4-biphenylcarboxylic acid dihydrochloride NMR (DMSO-$d_6$, δ): 1.22 (3H, d, J=5.9 Hz), 1.8-2.1 (4H, m), 2.5-3.3 (6H, m), 4.08 (2H, t, J=7 Hz), 5.29 (1H, m), 6.9 (1H, m), 7.1-7.3 (4H, m), 7.6-7.8 (2H, m), 7.99 (1H, m), 8.5 (1H, m), 8.86 (1H, m), 9.2 (2H, m) MS (m/z): 435 (M+H)

(34) 3-(Cyclohexyloxy)-4'-[(2S)-3-hydroxy-2-[[(2R)-2-hydroxy-2-phenylethyl]amino]propyl]-N-(methylsulfonyl)-4-biphenylcarboxamide hydrochloride NMR (DMSO-$d_6$, δ): 1.1-2.1 (10H, m), 3.23 (3H, s), 2.8-3.7 (7H, m), 4.80 (1H, m), 5.09 (1H, m), 5.44 (1H, m), 6.20 (1H, m), 7.1-7.8 (12H, m) MS (m/z): 567 (M+H)

(35) 4'-[2-[[(2R)-2-Hydroxy-2-(3-pyridyl)ethyl]amino]ethyl]-N-(methylsulfonyl)-3-phenoxy-4-biphenylcarboxamide dihydrochloride NMR (DMSO-$d_6$, δ): 3.0-3.3 (6H, m), 3.33 (3H, s), 4.82 (1H, m), 5.10 (1H, m), 7.0-7.8 (13H, m), 8.0-8.2 (1H, m), 8.6-8.8 (2H, m) MS (m/z): 532 (M+H)

(36) 4'-[2-[[(2R)-2-Hydroxy-2-phenylethyl]amino]ethyl]-N-(methylsulfonyl)-3-phenoxy-4-biphenylcarboxamide hydrochloride NMR (DMSO-$d_6$, δ): 3.0-3.3 (6H, m), 3.33 (3H, s), 4.82 (1H, m), 5.02 (1H, m), 6.20 (1H, m), 7.1-7.5 (12H, m), 7.5-7.9 (5H, m) MS (m/z): 531 (M+H)

(37) 4'-[2-[[(2R)-2-[3-(Benzyloxy)phenyl]-2-hydroxyethyl]-(tert-butoxycarbonyl)amino]ethyl]-3-isopropoxy-4-biphenylcarboxylic acid methyl ester MS (m/z): 640 (M+H)

EXAMPLE 67

The following compound was obtained according to a similar manner to that of Example 1 followed by a similar manner to that of Example 54.

4'-[2-[[(2R)-2-Hydroxy-2-phenylethyl]amino]ethyl]-3-(3-pyridyloxy)-4-biphenylcarboxylic acid dihydrochloride NMR (DMSO-$d_6$, δ): 3.0-3.2 (6H, m), 4.95-5.2 (1H, m), 7.3-7.4 (7H, m), 7.6-7.8 (6H, m), 7.7-8.0 (5H, m), 8.03 (1H, d, J=8.2 Hz), 8.42-8.51 (2H, m), 8.89 (1H, br), 9.22 (1H, br) MS (m/z): 453 (M−2HCl—H)−

EXAMPLE 68

To a mixture of tert-butyl [3-(4-bromophenyl)propyl]-[(2R)-2-hydroxy-2-(3-pyridyl)ethyl]carbamate (312 mg), [3-isobutoxy-4-(methoxycarbonyl)phenyl]boronic acid (207 mg), [1,1'-bis(diphenylphosphino)ferrocene]palladium(II) dichloride (58.4 mg) and 1,1'-bis(diphenylphosphino)ferrocene (7.93 mg) in N,N-dimethylformamide (3.12 ml) was added 2.0M aqueous sodium carbonate solution (1.25 ml) and the mixture was stirred at 90° C. for 2.5 hours. After cooling to room temperature, palladium was removed by filtration through a Celite cake. The mixture was extracted with ethyl acetate and the extract was washed with water and brine and dried over magnesium sulfate. Filtration followed by evaporation under reduced pressure gave a crude product which was purified by column chromatography on silica gel (hexane/ethyl acetate=1/1) to give methyl 4'-[3-[(tert-butoxycarbonyl)[(2R)-2-hydroxy-2-(3-pyridyl)ethyl]amino]-propyl]-3-isobutoxy-4-biphenylcarboxylate (374 mg) as a yellow solid (foam).

(+)ESI-MS (m/z): 563 (M+H)+, 585 (M+Na)+

EXAMPLE 69

The following compound was obtained according to a similar manner to that of Example 68.

Methyl 4'-[2-[(tert-butoxycarbonyl)[(2R)-2-hydroxy-2-(3-pyridyl)ethyl]amino]ethyl]-3-isobutoxy-4-biphenylcarboxylate (+)ESI-MS (m/z): 563 (M+H)+, 585 (M+Na)+

EXAMPLE 70

To a solution of methyl 4'-[2-[[tert-butoxycarbonyl]-[(2R)-2-hydroxy-2-(3-pyridyl)ethyl]amino]ethyl]-3-isobutoxy-4-biphenylcarboxylate (511 mg) in methanol (5.11 ml) and tetrahydrofuran (1.53 ml) was added 1N sodium hydroxide (2.79 ml) and the mixture was stirred at room temperature for 36 hours. Methanol and tetrahydrofuran were removed by evaporation under reduced pressure and the pH was adjusted to 5.9 with 0.1N hydrochloric acid. The mixture was extracted with ethyl acetate (twice) and the extract was washed with water and brine and dried over magnesium sulfate. Filtration followed by evaporation under reduced pressure gave 4'-[2-[[tert-butoxycarbonyl][(2R)-2-hydroxy-2-(3-pyridyl)ethyl]amino]ethyl]-3-isobutoxy-4-biphenylcarboxylic acid (494 mg) as a brown solid (foam).

(−)ESI-MS (m/z): 533 (M−H)−

EXAMPLE 71

The following compound was obtained according to a similar manner to that of Example 70.

4-[3-[[tert-Butoxycarbonyl][(2R)-2-hydroxy-2-(3-pyridyl)ethyl]amino]propyl]-3-isobutoxy-4-biphenylcarboxylic acid (−)ESI-MS (m/z): 547 (M−H)−

EXAMPLE 72

To a solution of 4'-[2-[[tert-butoxycarbonyl][(2R)-2-hydroxy-2-(3-pyridyl)ethyl]amino]ethyl]-3-isobutoxy-4-biphenylcarboxylic acid (170 mg) in N,N-dimethylformamide (1.70 ml) was added 1,1'-carbonylbis(1H-imidazole) (61.7 mg) and the mixture was stirred at room temperature for 1 hour under nitrogen atmosphere. To the reaction mixture were added methanesulfonamide (36.3 mg) and 2,3,4,6,7,8,9,10-octahydropyrimido[1,2-a]azepine (0.057 ml) and the mixture was stirred at 120° C. for 12 hours. After cooling to room temperature, to the reaction mixture was added water (10 ml) and the pH was adjusted to 5.98 with 0.1N hydrochloric acid. The mixture was extracted with ethyl acetate (twice), washed with water and brine and dried over magnesium sulfate. Filtration followed by evaporation under reduced pressure gave a crude produce which was purified by column chromatography on silica gel (eluent: hexane/ethyl acetate=1/1.5) and further purification by column chromatography on silica gel (eluent: chloroform/methanol=100/0 to 99/1) gave tert-butyl [(2R)-2-hydroxy-2-(3-pyridyl)ethyl][2-

[3'-isobutoxy-4'-[[(methylsulfonyl)amino]carbonyl]-4-biphenylyl]ethyl]carbamate (63 mg) as a white foam.

(−)ESI-MS (m/z): 610 (M−H)⁻

EXAMPLE 73

The following compound was obtained according to a similar manner to that of Example 72.

tert-Butyl [(2R)-2-hydroxy-2-(3-pyridyl)ethyl][3-[3'-isobutoxy-4'-[[(methylsulfonyl)amino]carbonyl]-4-biphenylyl]propyl]carbamate (−)ESI-MS (m/z): 624 (M−H)⁻

EXAMPLE 74

To a mixture of tert-butyl [2-(4-bromophenyl)ethyl]-[(2R)-2-hydroxy-2-(3-pyridyl)ethyl]carbamate (500 mg), [3-isobutyl-4-(methoxycarbonyl)phenyl]boronic acid (336 mg), [1,1'-bis(diphenylphosphino)feffocene]palladium(II) dichloride (48.5 mg) and 1,1'-bis(diphenylphosphino)ferrocene (16.4 mg) in N,N-dimethylformamide (3.75 ml) was added 2.0M aqueous sodium carbonate solution (2.08 ml) and the mixture was stirred at 90° C. for 3 hours. After cooling to room temperature, the mixture was partitioned between ethyl acetate (30 ml) and water (30 ml). The organic layer was separated, washed with brine (30 ml) and dried over magnesium sulfate. Filtration followed by evaporation under reduced pressure gave a crude product which was purified by column chromatography on silica gel (hexane/ethyl acetate=1/1 to 1/3) to give methyl 4'-[2-[[tert-butoxycarbonyl]-[(2R)-2-hydroxy-2-(3-pyridyl)ethyl]amino]ethyl]-3-isobutyl-4-biphenylcarboxylate (395 mg) as a yellow solid (foam).

(+)ESI-MS (m/z): 533 (M+H)⁺, 555 (M+Na)⁺, 571 (M+K)⁺

EXAMPLE 75

To a solution of methyl 4'-[2-[[tert-butoxycarbonyl]-[(2R)-2-hydroxy-2-(3-pyridyl)ethyl]amino]ethyl]-3-isobutyl-4-biphenylcarboxylate (390 mg) in methanol (3.90 ml) and tetrahydrofuran (1.56 ml) was added 1N aqueous sodium hydroxide solution (2.20 ml) and the mixture was stirred at room temperature for 2 days. Methanol and tetrahydrofuran were removed by evaporation under reduced pressure and to the mixture was added ethyl acetate (20 ml). The pH was adjusted to 4.3 with 1N hydrochloric acid and the organic layer was separated, washed with water (20 ml) and brine (20 ml) and dried over magnesium sulfate. Filtration followed by evaporation under reduced pressure gave a crude product which was purified by column chromatography on silica gel (eluent: hexane/ethyl acetate=1/2) to give 4'-[2-[[tert-butoxycarbonyl][(2R)-2-hydroxy-2-(3-pyridyl)ethyl]amino]-ethyl]-3-isobutyl-4-biphenylcarboxylic acid (291 mg) as a white solid (foam).

(−)ESI-MS (m/z): 517 (M−H)⁻

EXAMPLE 76

The following compounds were obtained according to a similar manner to that of Preparation 14.
(1) ((2R)-2-Hydroxy-2-phenylethyl)[2-[4'-[[(methanesulfonyl)amino)carbonyl]-3'-(2-methoxyethoxy)-4-biphenylyl]ethyl]carbamic acid tert-butyl ester NMR (CDCl₃, δ): 1.25 (9H, s), 2.6-3.0 (2H, m), 3.2-3.5 (4H, m), 3.41 (3H, s), 3.51 (3H, s), 3.81-3.86 (2H, m), 4.35-3.39 (2H, m), 4.9-4.93 (1H, m), 7.13-7.4 (11H, m), 8.2 (1H, d, J=8 Hz), 10.5 (1H, s)
(2) ((2R)-2-Hydroxy-2-phenylethyl)[2-[4'-[[(methanesulfonyl)amino]carbonyl]-3'-(2,2,2-trifluoroethoxy)-4-biphenylyl)ethyl]carbamic acid tert-butyl ester (+)ESI-MS (m/z): 637 (M+H)⁺

EXAMPLE 77

To a solution of tert-butyl [2-(4-bromophenyl)ethyl]-[(2R)-2-hydroxy-2-phenyl]carbamate (260 mg) in toluene (3.0 ml) and ethanol (780 μl) were added [3-(2-fluoroethoxy)-4-[[(methylsulfonyl)amino]carbonyl]phenyl]boronic acid (245 mg), [1,1'-bis(diphenylphosphino)ferrocene]-dichloropalladium(II) (45.3 mg) 1,1'-bis(diphenylphosphino)ferrocene (34.3 mg) and aqueous solution of sodium carbonate (2M, 990 μl), and the mixture was stirred at 95° C. for 2.5 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=55/45) to give [2-[3'-(2-fluoroethoxy)-4'-[[(methanesulfonyl)amino]carbonyl]-4-biphenylyl]ethyl][(2R)-2-hydroxy-2-phenylethyl]carbamic acid tert-butyl ester (150 mg).

(+)ESI-MS (m/z): 601 (M+H)⁺

EXAMPLE 78

The following compounds were obtained according to a similar manner to that of Example 77.
(1) tert-Butyl [(1S,2R)-2-hydroxy-1-methyl-2-phenylethyl]-[2-[4'-[[(methylsulfonyl)amino]carbonyl]-3'-(2,2,2-trifluoroethoxy)-4-biphenylyl]ethyl]carbamate (+)ESI-MS (m/z): 651 (M+H)⁺
(2) tert-Butyl [(2R)-2-hydroxy-2-(3-pyridyl)ethyl][2-[4'-[[(methylsulfonyl)amino]carbonyl]-3'-(2,2,2-trifluoroethoxy)-4-biphenylyl]ethyl]carbamade (+)ESI-MS (m/z): 638 (M+H)⁺
(3) tert-Butyl [2-[3'-(3-fluoropropoxy)-4'-[[(methylsulfonyl)amino]carbonyl]-4-biphenylyl]ethyl]-[(2R)-2-hydroxy-2-phenylethyl]carbamaate (+)ESI-MS (m/z): 615 (M+H)⁺
(4) tert-Butyl [2-[3'-(3-fluoropropoxy)-4'-[[(methylsulfonyl)amino]carbonyl]-4-biphenylyl]ethyl]-[(1S,2R)-2-hydroxy-1-methyl-2-phenylethyl]carbamate (+)ESI-MS (m/z): 629 (M+H)⁺

EXAMPLE 79

N-Isopropyl-2-propanamine was added to a solution of 4'-(2-bromoethyl)-3-isopropoxy-N-(methylsulfonyl)-4-biphenylcarboxamide (87.6 mg) and 4-(1R,2S)-2-amino-1-hydroxypropyl]phenol (59.8 mg) in N,N-dimethylformamide (876 μl) at room temperature. After stirring for 1 hour at 135° C., the product was extracted with ethyl acetate. The water layer was evaporated under reduced pressure. The residue was purified column chromatography to give 4'-[2-[[(1S,2R)-2-hydroxy-2-(4-hydroxyphenyl)-1-methylethyl]amino]ethyl]-3-isopropoxy-N-(methylsulfonyl)-4-biphenylcarboxamide hydrochloride (23.1 mg).

NMR (DMSO-d₆, δ): 0.98 (3H, d, J=6.7 Hz), 1.37 (3H, s), 1.38 (3H, s), 3.08 (21H, t, J=8.1 Hz), 3.15-3.44 (3H, m), 3.44 (3H, s), 4.94-5 (1H, m), 5.07 (1H, br s), 5.99 (1H, d, J=4.1 Hz), 6.76 (2H, d, J=8.6 Hz), 7.17 (2H, d, J=8.6 Hz), 7.36-7.43

(4H, m), 7.74-7.78 (3H, m), 8.78 (1H, br s), 9.42 (1H, s) (+)ESI-MS (m/z): 527 (M+H)⁺ (free)

EXAMPLE 80

To a solution of ethyl [4'-[2-[(tert-butoxycarbonyl)-[(2R)-2-hydroxy-2-phenylethyl]amino]ethyl]-3-cyclohexyloxy-4-biphenylyl]acetate (441 mg) in ethanol (4.4 ml) was added 1N sodium hydroxide (1.83 ml) at room temperature, and the mixture was stirred at the same temperature for 8 hours. To the resulting mixture was added 1N hydrochloric acid (1.83 ml), and ethanol was removed by evaporation under reduced pressure. To the aqueous mixture was added ethyl acetate and water. After separation, the organic layer was dried over anhydrous magnesium sulfate and evaporated under reduced pressure. The residue was purified by column chromatography on silica gel (chloroform/methanol=100:1 to 20:1) to give [4'-[2-[(tert-butoxycarbonyl)[(2R)-2-hydroxy-2-phenylethyl]amino]ethyl]-3-cyclohexyloxy-4-biphenylyl]-acetic acid (359 mg).

(−)ESI-MS (m/z): 572 (M−H)⁻

EXAMPLE 81

The following compound was obtained according to a similar manner to that of Example 80.

[4'-[2-[(tert-Butoxycarbonyl)[(2R)-2-hydroxy-2-(3-pyridyl)ethyl]amino]ethyl]-3-(cyclohexyloxy)-4-biphenylyl]acetic acid (−)ESI-MS (m/z): 574 (M−H)⁻

EXAMPLE 82

To a solution of [4'-[2-[(tert-butoxycarbonyl)[(2R)-2-hydroxy-2-phenylethyl]amino]ethyl]-3-(cyclohexyloxy)-4-biphenylyl]acetic acid (228 mg) in N,N-dimethylformamide (2.5 ml) was added 1,1'-carbonyldiimidazole (77 mg) at room temperature under nitrogen, and the mixture was stirred at the same temperature for 1.5 hours. To this one were added methanesulfonamide (76 mg) and 1,8-diazabicyclo[5.4.0]-7-undecene (91 mg) at 5° C., and the mixture was stirred at the same temperature for 5 hours. The resulting mixture was poured into 1N hydrochloric acid and the aqueous layer was extracted with ethyl acetate. The organic layer was washed successively with 1N hydrochloric acid (twice) and brine, dried over anhydrous magnesium sulfate and evaporated under reduced pressure. The residue was purified by column chromatography on silica gel (chloroform/ethyl acetate=10:1 to 5:1) to give tert-butyl [2-(3'-(cyclohexyloxy)-4'-[2-[(methylsulfonyl)amino]-2-oxoethyl]-4-biphenylyl]ethyl]-[(2R)-2-hydroxy-2-phenylethyl]carbamate (61 mg).

(+)ESI-MS (m/z): 673 (M+Na)⁺

EXAMPLE 83

The following compound was obtained according to a similar manner to that of Example 82.

tert-Butyl [2-[3'-(cyclohexyloxy)-4'-[2-[(methylsulfonyl)amino]-2-oxoethyl]-4-biphenylyl]ethyl]-[(2R)-2-hydroxy-2-(3-pyridyl)ethyl]carbamate (+)ESI-MS (m/z): 652 (M+H)⁺

EXAMPLE 84

The following compound was obtained according to a similar manner to that of Example 42.

4'-[2-[[(2R)-2-Hydroxy-2-[4-hydroxy-3-[(methylsulfonyl)amino]phenyl]ethyl]amino]ethyl]-3-isopropoxy-4-biphenylcarboxylic acid hydrochloride NMR (DMSO-d₆, δ): 1.31 (6H, d, J=6 Hz), 2.95 (3H, s), 2.83-3.34 (6H, m), 4.76-4.88 (2H, m), 6.11 (1H, br s), 6.92 (1H, d, J=8.2 Hz), 7.07 (1H, dd, J=1.7, 8.4 Hz), 7.25-7.39 (5H, m), 7.68-7.72 (3H, m), 8.81 (1H, br s), 10.03 (1H, br s) (−)ESI-MS (m/z): 527 (M−H)⁻

EXAMPLE 85

The following compounds were obtained according to a similar manner to that of Example 6.

(1) 4'-[2-[[(2R)-2-Hydroxy-2-phenylethyl]amino]ethoxy]-3-isopropoxy-N-(methylsulfonyl)-4-biphenylcarboxamide hydrochloride NMR (DMSO-d₆, δ): 1.38 (6H, d, J=5.9 Hz), 3.1 (1H, dd, J=10.6, 12.4 Hz), 3.25-3.32 (1H, m), 3.38 (3H, s), 3.44-3.46 (2H, m), 4.34-4.40 (2H, m), 4.95-5.01 (2H, m), 6.20 (1H, d, J=3.3 Hz) 7.11 (2H, d, J=8.8 Hz), 7.31-7.42 (7H, m), 7.76-7.78 (3H, m), 9.07 (3H, br) (−)ESI-MS (m/z): 511 (M−H)⁻

(2) 4'-[2-[[(2R)-2-Hydroxy-2-phenylethyl]amino]ethoxy]-N-(methylsulfonyl)-3-propoxy-4-biphenylcarboxamide hydrochloride NMR (DMSO-d₆, δ): 1.05 (3H, t, J=7.3 Hz), 1.83 (2H, sextuplet, J=7.3 Hz), 3.11 (1H, dd, J=10.6, 12.4 Hz), 3.28 (1H, d, J=12.1 Hz), 3.37 (3H, s), 3.45 (2H, t, J=5.1 Hz), 4.21 (2H, t, J=6.6 Hz), 4.35-4.41 (2H, m), 5.01 (1H, dt, J=10.6, 3.3 Hz), 6.22 (1H, d, J=3.3 Hz), 7.11 (2H, d, J=8.8 Hz), 7.31-7.42 (7H, m), 7.74 (1H, d, J=8.1 Hz), 7.78 (2H, d, J=8.8 Hz), 9.07 (2H, br), 11.1 (1H, br) (−)ESI-MS (m/z): 511 (M−H)⁻

(3) 3-(Cyclopentyloxy)-4'-[2-[[(2R)-2-hydroxy-2-phenylethyl]amino]ethoxy]-N-(methylsulfonyl)-4-biphenylcarboxamide hydrochloride NMR (DMSO-d₆, δ): 1.60-2.02 (8H, m), 3.11 (1H, dd, J=10.6, 12.4 Hz), 3.25-3.29 (1H, m), 3.38 (3H, s), 3.44-3.47 (2H, m), 4.35-4.42 (2H, m), 5.00-5.04 (1H, m), 5.22-5.26 (1H, m), 6.22 (1H, d, J=3.7 Hz), 7.12 (2H, d, J=8.8 Hz), 7.31-7.43 (7H, m), 7.75-7.78 (3H, m), 9.22 (3H, br) (−)ESI-MS (m/z): 537 (M−H)⁻

(4) 3-(Cyclohexyloxy)-4'-[2-[[(2R)-2-hydroxy-2-phenylethyl]amino)ethoxy]-N-(methylsulfonyl)-4-biphenylcarboxamide hydrochloride NMR (DMSO-d₆, δ): 1.34-1.64 (6H, m), 1.69-1.78 (2H, m), 1.93-2.01 (2H, m), 3.11 (1H, dd, J=10.6, 12.4 Hz), 3.25-3.29 (1H, m), 3.39 (3H, s), 3.46 (2H, t, J=5.1 Hz), 4.37-4.41 (2H, m), 4.80-4.86 (1H, m), 5.01-5.05 (1H, m), 6.23 (1H, d, J=3.7 Hz), 7.12 (2H, d, J=8.8 Hz), 7.31-7.43 (7H, m), 7.75-7.79 (3H, m), 9.19 (2H, br), 11.1 (1H, br) (−)ESI-MS (m/z): 551 (M−H)⁻

(5) 3-(Cycloheptyloxy)-4'-[2-[[(2R)-2-hydrox-2-phenylethyl]amino]ethoxy]-N-(methylsulfonyl)-4-biphenylcarboxamide hydrochloride NMR (DMSO-d₆, δ): 1.46-1.72 (8H, m), 1.77-1.86 (2H, m), 2.02-2.10 (2H, m), 3.11 (1H, dd, J=10.6, 12.4 Hz), 3.25-3.29 (1H, m), 3.39 (3H, s), 3.45 (2H, t, J=5.1 Hz), 4.34-4.43 (2H, m), 4.95-5.04 (2H, m), 6.22 (1H, d, J=3.3 Hz), 7.12 (2H, d, J=8.8 Hz), 7.31-7.43 (7H, m), 7.75-7.79 (3H, m), 9.20 (2H, br), 10.9 (1H, br) (−)ESI-MS (m/z): 565 (M−H)⁻

(6) 4'-[2-[[(2R)-2-Hydroxy-2-phenylethyl]amino]ethoxy]-N-(methylsulfonyl)-3-(pentyloxy)-4-biphenylcarboxamide hydrochloride NMR (DMSO-$d_6$, δ): 0.92 (3H, t, J=7.3 Hz), 1.33-1.51 (4H, m), 1.78-1.84 (2H, m), 3.11 (1H, dd, J=10.6, 12.4 Hz), 3.27 (1H, dd, J=1.8, 12.4 Hz), 3.37 (3H, s), 3.45 (2H, t, J=5.1 Hz), 4.24 (2H, t, J=6.6 Hz), 4.36-4.42 (2H, m), 5.03 (1H, dt, J=10.6, 3.3 Hz), 6.22 (1H, d, J=3.3 Hz), 7.11 (2H, d, J=8.8 Hz), 7.31-7.43 (7H, m), 7.74 (1H, d, J=8.1 Hz), 7.78 (2H, d, J=8.8 Hz), 9.32 (3H, br) (−)ESI-MS (m/z): 539 (M−H)⁻

(7) 4'-[2-[[(2R)-2-Hydroxy-2-phenylethyl]amino]ethoxy]-3-isobutyl-N-(methylsulfonyl)-4-biphenylcarboxamide hydrochloride NMR (DMSO-$d_6$, δ): 0.87 (6H, d, J=6.6 Hz), 1.84 (1H, heptupulet, J=6.6 Hz), 2.74 (2H, d, J=7.0 Hz), 3.08-3.30 (2H, m), 3.36 (3H, s), 3.44-3.47 (2H, m), 4.32-4.41 (2H, m), 5.00 (1H, dt, J=10.3, 3.3 Hz), 6.22 (1H, d, J=3.3 Hz), 7.11 (2H, d, J=8.8 Hz), 7.31-7.43 (5H, m), 7.52-7.58 (3H, m), 7.71 (2H, d, J=8.8 Hz), 8.95 (2H, br), 12.2 (1H, br) (−)ESI-MS (m/z): 509 (M−H)⁻

(8) 3-Cyclopentyl-4'-[2-[[(2R)-2-hydroxy-2-phenylethyl]amino]ethoxy]-N-(methylsulfonyl)-4-biphenylcarboxamide hydrochloride NMR (DMSO-$d_6$, δ): 1.58-2.10 (8H, m), 3.03-3.28 (3H, m), 3.39 (3H, s), 3.46 (2H, br), 4.34-4.39 (2H, m), 4.96-5.05 (1H, m), 6.22 (1H, d, J=3.5 Hz), 7.10 (2H, d, J=9.0 Hz), 7.33-7.73 (10H, m), 9.02 (2H, br), 12.2 (1H, br) (−)ESI-MS (m/z): 521 (M−H)⁻

(9) 4'-[2-[[(2R)-2-(4-Aminophenyl)-2-hydroxyethyl]amino]-ethyl]-3-(cyclohexyloxy)-N-(methylsulfonyl)-4-biphenylcarboxamide dihydrochloride NMR (DMSO-$d_6$, δ): 1.31-1.64 (6H, m), 1.69-1.77 (2H, m), 1.92-1.98 (2H, m), 3.01-3.26 (6H, m), 3.39 (3H, s), 4.79-4.84 (1H, m), 4.99 (1H, dd, J=2.2, 10.3 Hz), 7.25 (2H, d, J=7.7 Hz), 7.35-7.45 (6H, m), 7.74 (1H, d, J=8.1 Hz), 7.78 (1H, d, J=8.1 Hz), 8.91 (1H, br), 9.25 (1H, br), 9.74 (1H, br), 11.2 (1H, br) (−)ESI-MS (m/z): 550 (M−H)⁻

(10) 4'-[2-[[(2R)-2-(4-Aminophenyl)-2-hydroxyethyl]amino]-ethyl]-3-cyclopentyl-N-(methylsulfonyl)-4-biphenylcarboxamide dihydrochloride NMR (DMSO-$d_6$, δ): 1.59-2.09 (8H, m), 3.00-3.36 (7H, m), 3.40 (3H, s), 5.00 (1H, d, J=9.9 Hz), 6.28 (1H, br), 7.24-7.30 (2H, m), 7.38 (2H, d, J=8.1 Hz), 7.45 (2H, d, J=7.3 Hz), 7.49 (1H, d, J=8.1 Hz), 7.56 (1H, dd, J=1.8, 8.1 Hz), 7.64 (1H, d, J=1.8 Hz), 7.69 (2H, d, J=8.1 Hz), 8.92 (1H, br), 9.26 (1H, br), 9.85 (2H, br), 12.2 (1H, br) (−)ESI-MS (m/z): 520 (M−H)⁻

(11) 4'-[2-[[(2R)-2-(4-Aminophenyl)-2-hydroxyethyl]amino]-ethyl]-3-isobutyl-N-(methylsulfonyl)-4-biphenylcarboxamide dihydrochloride NMR (DMSO-$d_6$, δ): 0.87 (6H, d, J=6.6 Hz), 1.84 (1H, heptuplet, J=7.0 Hz), 2.74 (2H, d, J=7.0 Hz), 3.00-3.24 (6H, m), 3.38 (3H, s), 5.00 (1H, dd, J=1.5, 9.9 Hz), 6.27 (1H, br), 7.27 (2H, d, J=8.4 Hz), 7.38 (2H, d, J=8.4 Hz), 7.44 (2H, d, J=8.4 Hz), 7.54-7.61 (3H, m), 7.70 (2H, d, J=8.4 Hz), 8.91 (1H, br), 9.23 (1H, br), 9.83 (2H, br), 1.22 (1H, br) (−)ESI-MS (m/z): 508 (M−H)⁻

(12) 4'-[2-[[(2R)-2-(4-Aminophenyl)-2-hydroxyethyl]amino]-ethoxy]-3-isobutyl-N-(methylsulfonyl)-4-biphenylcarboxamide dihydrochloride NMR (DMSO-$d_6$, δ): 0.87 (6H, d, J=6.6 Hz), 1.83 (1H, heptuplet, J=7.0 Hz), 2.73 (2H, d, J=7.0 Hz), 3.06-3.29 (2H, m), 3.38 (3H, s), 3.42-3.48 (2H, m), 4.34-4.42 (1H, m), 6.28 (1H, br), 7.11 (2H, d, J=8.4 Hz), 7.29 (2H, d, J=8.4 Hz), 7.46 (2H, d, J=8.4 Hz), 7.52-7.59 (3H, m), 7.71 (2H, d, J=8.4 Hz), 9.01 (1H, br), 9.27 (1H, br), 9.88 (2H, br), 12.2 (1H, br) (−)ESI-MS (m/z): 524 (M−H)⁻

(13) 4'-[2-[[(2R)-2-(4-Aminophenyl)-2-hydroxyethyl]amino]-ethoxy]-3-cyclopentyl-N-(methylsulfonyl)-4-biphenylcarboxamide dihydrochloride NMR (DMSO-$d_6$, δ): 1.59-2.09 (8H, m), 3.06-3.36 (3H, m), 3.39 (3H, s), 3.42-3.48 (2H, m), 4.33-4.42 (2H, m), 5.03 (1H, dd, J=2.2, 10.3 Hz), 6.27 (1H, br), 7.11 (2H, d, J=8.8 Hz), 7.28 (2H, d, J=8.1 Hz), 7.44-7.48 (3H, m), 7.53 (1H, dd, J=1.5, 8.1 Hz), 7.62 (1H, d, J=1.5 Hz), 7.70 (1H, d, J=8.8 Hz), 9.02 (1H, br), 9.28 (1H, br), 9.81 (2H, br), 12.2 (1H, br) (−)ESI-MS (m/z): 536 (M−H)⁻

(14) 3-(Cyclohexyloxy)-4'-[3-[[(2R)-2-hydroxy-2-phenylethyl]amino]propyl]-N-(propylsulfonyl)-4-biphenylcarboxamide hydrochloride NMR (DMSO-$d_6$, δ): 1.02 (3H, t, J=7.3 Hz), 1.28-1.62 (6H, m), 1.68-1.81 (4H, m), 1.91-2.07 (4H, m), 2.71 (2H, t, J=7.3 Hz), 2.96-3.03 (3H, m), 3.13-3.18 (1H, m), 3.48-3.52 (2H, m), 4.77-4.83 (1H, m), 4.93 (1H, dd, J=10.3, 3.3 Hz), 6.18 (1H, d, J=3.3 Hz), 7.30-7.42 (9H, m), 7.65-7.72 (3H, m), 8.81 (2H, br), 11.1 (1H, br) (−)ESI-MS (m/z): 577 (M−H)⁻

EXAMPLE 86

The following compounds were obtained according to a similar manner to that of Example 45.

(1) tert-Butyl [(2R)-2-hydroxy-2-phenylethyl][2-[[4'-[[(methylsulfonyl)amino]carbonyl]-3'-propoxy-4-biphenylyl]oxy)ethyl]carbamate (−)ESI-MS (m/z): 611 (M−H)⁻

(2) tert-Butyl [(2R)-2-hydroxy-2-phenylethyl][2-[[3'-isobutyl-4'-[[(methylsulfonyl)amino]carbonyl]-4-biphenylyl]oxy]ethyl]carbamate (−)ESI-MS (m/z): 609 (M−H)⁻

(3) tert-Butyl [2-[[3'-cyclopentyl-4'-[[(methylsulfonyl)amino]carbonyl]-4-biphenylyl]oxy]ethyl][(2R)-2-hydroxy-2-phenylethyl]carbamate (−)ESI-MS (m/z): 621 (M−H)⁻

EXAMPLE 87

The following compounds were obtained according to a similar manner to that of Example 44.

(1) tert-Butyl [(2R)-2-hydroxy-2-phenylethyl][2-[[4'-[[(methylsulfonyl)amino]carbonyl]-3'-(pentyloxy)-4-biphenylyl]oxy]ethyl]carbamate (−)ESI-MS (m/z): 639 (M−H)⁻

(2) tert-Butyl [2-[[3'-(cyclopentyloxy)-4'-[[(methylsulfonyl)amino]carbonyl]-4-biphenylyl]oxy]-ethyl][(2R)-2-hydroxy-2-phenylethyl]carbamate (−)ESI-MS (m/z): 637 (M−H)⁻

(3) tert-Butyl [2-[[3'-(cyclohexyloxy)-4'-[[(methylsulfonyl)amino]carbonyl]-4-biphenylyl]oxy]-ethyl][(2R)-2-hydroxy-2-phenylethyl]carbamate (−)ESI-MS (m/z): 651 (M−H)⁻

(4) tert-Butyl [2-[[3'-(cycloheptyloxy)-4'-[[(methylsulfonyl)amino]carbonyl]-4-biphenylyl]oxy]-ethyl][(2R)-2-hydroxy-2-phenylethyl]carbamate (−)ESI-MS (m/z): 665 (M−H)⁻

(5) tert-Butyl [2-[3'-(cyclohexyloxy)-4'-[[(methylsulfonyl)amino]carbonyl]-4-biphenylyl]ethyl]-[(2R)-2-hydroxy-2-(4-nitrophenyl)ethyl]carbamate (−)ESI-MS (m/z): 680 (M−H)⁻

(6) tert-Butyl [2-[3'-cyclopentyl-4'-[[(methylsulfonyl)amino)carbonyl]-4-biphenylyl]ethyl][(2R)-2-hydroxy-2-(4-nitrophenyl)ethyl]carbamate (−)ESI-MS (m/z): 650 (M−H)⁻

(7) tert-Butyl [(2R)-2-hydroxy-2-(4-nitrophenyl)ethyl][2-[3'-isobutyl-4'-[[(methylsulfonyl)amino]carbonyl]-4-biphenylyl]ethyl]carbamate
(−)ESI-MS (m/z): 638 (M−H)⁻

(8) tert-Butyl [(2R)-2-hydroxy-2-(4-nitrophenyl)ethyl][2-[[3'-isopropoxy-4'-[[(methylsulfonyl)amino]carbonyl]-4-biphenylyl]oxy]ethyl]carbamate
(−)ESI-MS (m/z): 656 (M−H)⁻

(9) tert-Butyl [2-[[3'-(cyclohexyloxy)-4'-[[(methylsulfonyl)amino]carbonyl]-4-biphenylyl]oxy]-ethyl][(−2R)-2-hydroxy-2-(4-nitrophenyl)ethyl]carbamate
(−)ESI-MS (m/z): 696 (M−H)⁻

(10) tert-Butyl [(2R)-2-hydroxy-2-(4-nitrophenyl)ethyl](2-[[3'-isobutyl-4'-[[(methylsulfonyl)amino]carbonyl]-4-biphenylyl]oxy]ethyl]carbamate
(−)ESI-MS (m/z): 654 (M−H)⁻

(11) tert-Butyl [2-[[3'-cyclopentyl-4'-[[(methylsulfonyl)amino]carbonyl]-4-biphenylyl]oxy]ethyl][(2R)-2-hydroxy-2-(4-nitrophenyl)ethyl]carbamate
(−)ESI-MS (m/z): 666 (M−H)⁻

(12) tert-Butyl [2-[3'-(cyclohexyloxy)-4'-[[(methylsulfonyl)amino]carbonyl]-4-biphenylyl]ethyl]-[(2R)-2-hydroxy-2-(3-nitrophenyl)ethyl]carbamate
(−)ESI-MS (m/z): 680 (M−H)⁻

(13) Methyl 4'-[3-[(tert-butoxycarbonyl)[(2R)-2-hydroxy-2-phenylethyl]amino]propyl]-3-(cyclohexyloxy)-4-biphenylcarboxylate
(+)ESI-MS (m/z): 610 (M+Na)⁺

EXAMPLE 88

The following compounds were obtained according to a similar manner to that of Example 46.
(1) tert-Butyl [(2R)-2-(4-aminophenyl)-2-hydroxyethyl][2-[3'-cyclopentyl-4'-[[(methylsulfonyl)amino]carbonyl]-4-biphenylyl]ethyl]carbamate
(−)ESI-MS (m/z): 524 (M−H)⁻

(2) tert-Butyl [(2R)-2-(4-aminophenyl)-2-hydroxyethyl][2-[3'-isobutyl-4'-[[(methylsulfonyl)amino]carbonyl]-4-biphenylyl]ethyl]carbamate
(−)ESI-MS (m/z): 608 (M−H)⁻

(3) tert-Butyl [(2R)-2-(4-aminophenyl)-2-hydroxyethyl][2-[[3'-isopropoxy-4'-[[(methylsulfonyl)amino]carbonyl]-4-biphenylyl]oxy]ethyl]carbamate
(−)ESI-MS (m/z): 626 (M−H)⁻

(4) tert-Butyl [(2R)-2-(4-aminophenyl)-2-hydroxyethyl][2-[[3'-(cyclohexyloxy)-4'-[[(methylsulfonyl)amino]-carbonyl]-4-biphenylyl]oxy]ethyl]carbamate
(−)ESI-MS (m/z): 666 (M−H)⁻

(5) tert-Butyl [(2R)-2-(4-aminophenyl)-2-hydroxyethyl][2-[[3'-isobutyl-4'-[[(methylsulfonyl)amino]carbonyl]-4-biphenylyl]oxy]ethyl]carbamate
(−)ESI-MS (m/z): 624 (M−H)⁻

(6) tert-Butyl [(2R)-2-(4-aminophenyl)-2-hydroxyethyl][2-[[3'-cyclopentyl-4'-[[(methylsulfonyl)amino]carbonyl]-4-biphenylyl]oxy]ethyl]carbamate
(−)ESI-MS (m/z): 636 (M−H)⁻

(7) tert-Butyl [(2R)-2-(3-aminophenyl)-2-hydroxyethyl][2-[3'-(cyclohexyloxy)-4'-[[(methylsulfonyl)amino]-carbonyl]-4-biphenylyl]ethyl]carbamate
(−)ESI-MS (m/z): 650 (M−H)⁻

(8) tert-Butyl [(2R)-2-(4-aminophenyl)-2-hydroxyethyl][2-[3'-(isopropylthio)-4'-[[(methylsulfonyl)amino]-carbonyl]-4-biphenylyl]ethyl]carbamate
(−)ESI-MS (m/z): 626 (M−H)⁻

EXAMPLE 89

The following compounds were obtained according to a similar manner to that of Example 48.
(1) 4'-[2-[[(2R)-2-(6-Amino-3-pyridyl)-2-hydroxyethyl]-amino]ethyl]-3-(cyclohexyloxy)-N-(methylsulfonyl)-4-biphenylcarboxamide
NMR (DMSO-d$_6$, δ): 1.27-1.37 (3H, m), 1.43-1.58 (3H, m), 1.70-1.79 (2H, m), 1.82-1.91 (2H, m), 2.86-2.97 (2H, m), 2.99 (3H, s), 3.00-3.17 (4H, m), 4.47-4.53 (1H, m), 4.65-4.68 (1H, m), 5.73 (1H, br), 5.92 (2H, br s), 6.44 (1H, d, J=8.4 Hz), 7.18-7.21 (2H, m), 7.32 (2H, d, J=8.4 Hz), 7.37 (2H, dd, J=2.2, 8.4 Hz), 7.46 (1H, d, J=8.4 Hz), 7.63 (2H, d, J=8.4 Hz), 7.88 (1H, d, J=2.2 HZ), 8.21 (2H, br) (−)ESI-MS (m/z): 551 (M−H)⁻

(2) 4'-[2-[[(2R)-2-(6-Amino-3-pyridyl)-2-hydroxyethyl]-amino]ethyl]-3-(cyclohexyloxy)-4-biphenylcarboxylic acid
NMR (DMSO-d$_6$, δ): 1.28-1.61 (6H, m), 1.69-1.78 (2H, m), 1.82-1.91 (2H, m), 2.72-2.98 (6H, m), 4.52-4.65 (2H, m), 5.82 (2H, br s), 6.41 (1H, d, J=8.1 Hz), 7.21-7.38 (5H, m), 7.61-7.66 (3H, m), 7.85 (1H, br) (−)ESI-MS (m/z): 474 (M−H)⁻

(3) 4'-[2-[[(2R)-2-(6-Amino-3-pyridyl)-2-hydroxyethyl]-amino]ethyl]-3-(cycloheptyloxy)-4-biphenylcarboxylic acid dihydrochloride
NMR (DMSO-d$_6$, δ): 1.41-1.49 (2H, m), 1.53-1.59 (4H, m), 1.65-1.84 (4H, m), 1.90-1.98 (2H, m), 3.02-3.26 (6H, m), 4.77-4.82 (1H, m), 4.97 (1H, d, J=8.8 Hz), 6.44 (1H, br s), 7.02 (1H, d, J=9.9 Hz), 7.25 (1H, dd, J=1.5, 8.1 Hz), 7.28 (1H, d, J=1.5 Hz), 7.38 (2H, d, J=8.4 Hz), 7.69 (1H, d, J=8.1 Hz), 7.70 (2H, d, J=8.4 Hz), 7.93-7.96 (2H, m), 8.11 (2H, br), 9.04 (1H, br), 9.18 (1H, br), 12.5 (1H, br), 14.0 (1H, br) (−)ESI-MS (m/z): 488 (M−H)⁻

EXAMPLE 90

The following compounds were obtained according to a similar manner to that of Example 4.
(1) 2-Amino-4'-[2-[[(2R)-2-hydroxy-2-phenylethyl]amino]-ethyl]-4-biphenylcarboxylic acid dihydrochloride
NMR (DMSO-d$_6$, δ): 3.06-3.24 (6H, m), 4.77 (2H, br), 4.98-5.04 (1H, m), 7.22-7.66 (12H, m), 8.9 (1H, br), 9.3 (1H, br) MS (m/z): 375 (M−2HCl—H)⁻

(2) 2-Dimethylamino-4'-[2-[[(2R)-2-hydroxy-2-phenylethyl]-amino]ethyl]-4-biphenylcarboxylic acid dihydrochloride
NMR (DMSO-d$_6$, δ): 2.55 (6H, s), 3.05-3.22 (6H, m), 4.98-5.04 (1H, m), 7.22-7.66 (12H, m), 8.9 (1H, br), 9.3 (1H, br) MS (m/z): 403 (M−2HCl—H)⁻

(3) 4'-[2-[[(2R)-2-Hydroxy-2-phenylethyl]amino]ethyl]-2-(methylamino)-4-biphenylcarboxylic acid dihydrochloride
NMR (DMSO-d$_6$, δ): 2.70 (3H, s), 3.06-3.24 (6H, m), 4.98-5.04 (1H, m), 7.06-7.42 (12H, m), 8.9 (1H, br), 9.3 (1H, br) MS (m/z): 389 (M−2HCl—H)⁻

EXAMPLE 91

The following compounds were obtained according to a similar manner to that of Example 1 followed by a similar manner to that of Example 6.
(1) 3-Butyl-4'-[2-[[(2R)-2-hydroxy-2-phenylethyl]amino]-ethyl]-N-(methylsulfonyl)-4-biphenylcarboxamide hydrochloride
NMR (DMSO-d$_6$, δ): 0.89 (3H, t, J=7.1 Hz), 1.27-1.38 (2H, m), 1.53-1.60 (2H, m), 2.81 (3H, t, J=7.2 Hz), 3.04-3.40

(6H, m), 3.37 (3H, s), 4.97-5.02 (1H, m), 6.22 (1H, d, J=3.8 Hz), 7.28-7.42 (7H, m), 7.55-7.60 (3H, m), 7.70 (2H, d, J=8.1 Hz), 8.86 (1H, br), 9.09 (1H, br) MS (m/z): 493 (M−HCl−H)⁻

(2) 3-(Cyclohexylmethyl)-4'-[2-[[(2R)-2-hydroxy-2-phenylethyl]amino]ethyl]-N-(methylsulfonyl)-4-biphenylcarboxamide hydrochloride NMR (DMSO-d$_6$, δ): 0.91-1.17 (5H, m), 1.53-1.72 (6H, m), 2.74 (2H, d, J=6.3 Hz), 3.05-3.31 (6H, m), 3.37 (3H, s), 4.93-5.00 (1H, m), 6.22 (1H, d, J=3.8 Hz), 7.28-7.42 (7H, m), 7.51-7.61 (3H, m), 7.69 (2H, d, J=8.1 Hz), 8.90 (1H, br), 9.22 (1H, br) MS (m/z): 533 (M-HCl—H)⁻

(3) 4'-[2-[[(2R)-2-Hydroxy-2-phenylethyl]amino]ethyl]-3-(isobutylamino)-N-(methylsulfonyl)-4-biphenylcarboxamide dihydrochloride NMR (DMSO-d$_6$, δ): 0.99 (6H, d, J=6.7 Hz), 1.91-2.00 (1H, m), 2.83-3.30 (8H, m), 3.37 (3H, s), 4.96-5.02 (1H, m), 6.83-6.93 (2H, m), 7.31-7.42 (7H, m), 7.70 (2H, d, J=8.2 Hz), 7.82 (1H, d, J=8.4 Hz), 8.88 (1H, br), 9.20 (1H, br), 9.85 (1H, br) MS (m/z): 508 (M−2HCl—H)⁻

(4) 3-Cyclopentyl-4'-[2-[[(2R)-2-hydroxy-2-phenylethyl]amino]ethyl]-N-(methylsulfonyl)-4-biphenylcarboxamide hydrochloride NMR (DMSO-d$_6$, δ): 1.65-1.81 (6H, m), 1.99-2.05 (2H, m), 3.04-3.33 (7H, m), 3.38 (3H, s), 4.95-5.00 (1H, m), 6.22 (1H, d, J=3.8 Hz), 7.31-7.42 (7H, m), 7.46-7.58 (2H, m), 7.67 (1H, d, J=7.3 Hz), 7.69 (2H, d, J=8.1 Hz), 8.86 (1H, br), 9.10 (1H, br), 12.21 (1H, br) MS (m/z): 505 (M-HCl—H)⁻

(5) 3-Cyclohexyl-4'-[2-[[(2R)-2-hydroxy-2-phenylethyl]amino]ethyl]-N-(methylsulfonyl)-4-biphenylcarboxamide hydrochloride NMR (DMSO-d$_6$, δ): 1.28-1.84 (10H, m), 2.84-2.95 (2H, m), 3.04-3.24 (6H, m), 3.38 (3H, s), 4.95-5.00 (1H, m), 6.23 (1H, d, J=3.8 Hz), 7.31-7.40 (7H, m), 7.42-7.71 (5H, m), 8.86 (1H, br), 9.10 (1H, br), 12.2 (1H, br) MS (m/z): 519 (M-HCl—H)⁻

(6) 3-Cyclopentyl-4'-[2-[[(1S,2R)-2-hydroxy-1-methyl-2-phenylethyl]amino]ethyl]-N-(methylsulfonyl)-4-biphenylcarboxamide hydrochloride NMR (DMSO-d$_6$, δ): 0.97 (3H, d, J=6.7 Hz), 1.66-1.91 (6H, m), 2.03-2.06 (2H, m), 3.05-3.44 (7H, m), 3.38 (3H, s), 5.19 (1H, br), 6.16 (1H, d, J=4.2 Hz), 7.24-7.73 (12H, m), 8.86 (2H, br), 12.2 (1H, br) MS (m/z): 519 (M-HCl—H)⁻

(7) 4'-[(2R)-2-[[(2R)-2-Hydroxy-2-phenylethyl]amino]-propyl]-3-isobutyl-N-(methylsulfonyl)-4-biphenylcarboxamide hydrochloride NMR (DMSO-d$_6$, δ): 0.87 (6H, d, J=6.6 Hz), 1.15 (3H, d, J=6.0 Hz), 1.77-1.90 (1H, m), 2.73-2.85 (3H, m), 3.02-3.16 (2H, m), 3.37 (3H, s), 3.51-3.67 (2H, m), 4.98-5.03 (1H, m), 6.23 (1H, d, J=3.8 Hz), 7.31-7.73 (12H, m), 7.99 (1H, br), 8.79 (1H, br), 9.11 (1H, br), 12.2 (1H, br) MS (m/z): 507 (M-HCl—H)⁻

(8) 4'-[3-[[(2R)-2-Hydroxy-2-phenylethyl]amino]propyl]-3-(isopropylthio)-N-(methylsulfonyl)-4-biphenylcarboxamide hydrochloride NMR (DMSO-d$_6$, δ): 1.26 (6H, d, J=6.6 Hz), 1.9-2.0 (2H, m), 2.6-2.8 (2H, m), 3.0-3.1 (2H, m), 3.1-3.3 (2H, m), 3.36 (3H, s), 3.6-3.7 (1H, m), 4.9-5.0 (1H, m), 6.2 (1H, br), 7.3-7.7 (12H, m), 8.8-9.0 (2H, br) MS (m/z): 525 (M-HCl—H)⁻

(9) 4'-[3-[[(2R)-2-(3-Chlorophenyl)-2-hydroxyethyl]amino]-propyl]-3-(ispropylthio)-N-(methylsulfonyl)-4-biphenylcarboxamide hydrochloride NMR (DMSO-d$_6$, δ): 1.26 (6H, d, J=6.6 Hz), 1.9-2.0 (2H, m), 2.6-2.8 (2H, m), 3.1 (2H, br), 3.1-3.3 (2H, m), 3.37 (3H, s), 3.6-3.7 (1H, m), 4.9-5.0 (1H, m), 6.3 (1H, br), 7.3-7.7 (11H, m), 8.7-9.0 (2H, br) MS (m/z): 561 (M-HCl+H)⁺

(10) 4'[2-[[(2R)-2-(3-Chlorophenyl)-2-hydroxyethyl]amino]-ethoxy]-3-(isopropylthio)-N-(methylsulfonyl)-4-biphenylcarboxamide hydrochloride NMR (DMSO-d$_6$, δ): 1.26 (6H, d, J=6.6 Hz), 3.1-3.2 (2H, m), 3.36 (3H, s), 3.4-3.5 (2H, m), 3.65 (1H, td, J=6.6 Hz), 4.3-4.4 (2H, m), 5.0-5.1 (1H, m), 6.3 (1H, br), 7.12 (2H, d, J=8.7 Hz), 7.3-7.6 (9H, m), 9.0 (2H, br) MS (m/z): 561 (M-HCl—H)⁻

(11) 4'-[2-[[(2R)-2-Hydroxy-2-phenylethyl]amino]ethoxy]-3-(isopropylthio)-N-(methylsulfonyl)-4-biphenylcarboxamide hydrochloride NMR (DMSO-d$_6$, δ): 1.26 (6H, d, J=6.6 Hz), 3.1-3.2 (2H, m), 3.36 (3H, s), 3.4-3.5 (2H, m), 3.65 (1H, td, J=6.6 Hz), 4.3-4.4 (2H, m), 4.9-5.0 (1H, m), 6.3 (1H, br), 7.12 (2H, d, J=8.7 Hz), 7.3-7.6 (10H, m), 9.0 (2H, br) MS (m/z): 527 (M-HCl—H)⁻

EXAMPLE 92

The following compound was obtained according to a similar manner to that of Example 39.

4'-[2-[[(2R)-2-Hydroxy-2-phenylethyl]amino]ethyl]-3-(methylsulfonyl)-4-biphenylcarboxylic acid hydrochloride NMR (DMSO-d$_6$, δ): 3.05-3.36 (6H, m), 3.46 (3H, s), 4.98 (1H, d, J=5 Hz), 6.23 (1H, br s), 7.32-7.41 (5H, m), 7.44 (2H, d, J=4.1 Hz), 7.76 (2H, d, J=4.1 Hz), 7.83 (1H, d, J=4 Hz), 8.09 (1H, dd, J=0.9, 4 Hz), 8.19 (1H, d, J=0.9 Hz), 8.87 (1H, br s), 9.15 (1H, br s), 13.8 (1H, br s) (−)ESI-MS (m/z): 438 (M−H)⁻

EXAMPLE 93

The following compound was obtained according to a similar manner to that of Example 56.

4'-[2-[[(2R)-2-Hydroxy-2-phenylethyl]amino]-2-methylpropyl]-3-(isopropylthio)-4-biphenylcarboxylic acid hydrochloride NMR (DMSO-d$_6$, δ): 1.28 (6H, s), 1.31 (6H, d, J=6.6 Hz), 3.01-3.6 (4H, m), 3.7-3.83 (1H, m), 5.04 (1H, d, J=7.8 Hz), 7.3-7.52 (8H, m), 7.63 (1H, s), 7.72 (2H, d, J=8 Hz), 7.9 (1H, d, J=8.1 Hz) (−)ESI-MS (m/z): 462 (M−H)⁻

EXAMPLE 94

The following compounds were obtained according to a similar manner to that of Example 44 followed by a similar manner to that of Example 46 and then a similar manner to that of Example 14.

(1) 4'-[2-[[(2R)-2-(4-Aminophenyl)-2-hydroxyethyl]amino]-ethyl]-3-isopropoxy-4-biphenylcarboxylic acid dihydrochloride NMR (DMSO-d$_6$, δ): 1.31 (6H, d, J=6.0 Hz), 3.0-3.3 (6H, m), 4.82 (1H, m), 5.02 (1H, m), 7.1-7.5 (8H, m), 7.6-7.9 (3H, m), 8.9 (1H, m), 9.2 (1H, m) MS (m/z): 435 (M+H)

(2) 4'-[2-[[(2R)-2-(4-Aminophenyl)-2-hydroxyethyl]amino]-ethyl]-3-propoxy-4-biphenylcarboxylic acid dihydrochloride NMR (DMSO-d$_6$, δ): 1.09 (3H, t, J=7.2 Hz), 1.7-2.0 (2H, m), 3.0-3.3 (6H, m), 4.11 (2H, t, J=7.2 Hz), 5.02 (1H, m), 7.1-7.5 (8H, m), 7.6-7.9 (3H, m), 8.9 (1H, m), 9.2 (1H, m) MS (m/z): 435 (M+H)

(3) 4'-[2-[[(2R)-2-(4-Aminophenyl)-2-hydroxyethyl]amino]-ethyl]-3-isopropoxy-N-(methylsulfonyl)-4-biphenylcarboxamide dihydrochloride
NMR (DMSO-d$_6$, δ) 1.31 (6H, d, J=6.0 Hz), 3.0-3.3 (6H, m), 3.34 (3H, s), 5.02 (1H, m), 7.1-7.5 (8H, m), 7.6-7.9 (3H, m), 8.9 (1H, m), 9.2 (1H, m) MS (m/z): 512 (M+H)
(4) 4'-[2-[[(2R)-2-(4-Aminophenyl)-2-hydroxyethyl]amino]-ethyl]-N-(methylsulfonyl)-3-propoxy-4-biphenylcarboxamide dihydrochloride
NMR (DMSO-d$_6$, δ): 1.04 (3h, t, J=7.2 Hz), 1.7-2.0 (2H, m), 3.0-3.3 (6H, m), 3.37 (3H, s), 4.19 (2H, t, J=7.2 Hz), 5.02 (1H, m), 7.1-7.5 (8H, m), 7.6-7.9 (3H, m), 8.9 (1H, m), 9.2 (1H, m) MS (m/z): 512 (M+H)
(5) 4'-[2-[[(2R)-2-(3-Aminophenyl)-2-hydroxyethyl]amino]-ethoxy]-3-isopropoxy-4-biphenylcarboxylic acid dihydrochloride
NMR (DMSO-d$_6$, δ): 1.31 (6H, d, J=6.0 Hz), 3.0-4.2 (6H, m), 4.87 (1H, m), 5.07 (1H, m), 7.0-7.6 (8H, m), 7.7-7.9 (3H, m), 8.9-9.4 (2H, m) MS (m/z): 451 (M+H)
(6) 4'-[2-[[(2R)-2-(4-Aminophenyl)-2-hydroxyethyl]amino]-ethoxy]-3-isopropoxy-4-biphenylcarboxylic acid dihydrochloride
NMR (DMSO-d$_6$, δ): 1.30 (6H, d, J=6.0 Hz), 3.0-4.2 (6H, m), 4.87 (1H, m), 5.07 (1H, m), 7.0-7.7 (8H, m), 7.7-7.9 (3H, m), 8.9-9.4 (2H, m) MS (m/z): 451 (M+H)
(7) 4'-[2-[[(2R)-2-(3-Aminophenyl)-2-hydroxyethyl](tert-butoxycarbonyl)amino]ethyl]-3-isopropoxy-4-biphenylcarboxylic acid methyl ester
MS (m/z): 549 (M+H)
(8) 4'-[2-[[(2R)-2-(3-Aminophenyl)-2-hydroxyethyl]amino]-ethyl]-3-isopropoxy-N-(methylsulfonyl)-4-biphenylcarboxamide dihydrochloride
NMR (DMSO-d$_6$, δ): 1.36 (6H, d, J=5.9 Hz), 2.9-3.5 (6H, m), 3.29 (3H, s), 4.9 (2H, m), 6.21 (1H, m), 6.6-6.9 (3H, m), 7.0-7.3 (6H, m), 7.7-7.9 (2H, m) MS (m/z): 512 (M+H)

EXAMPLE 95

The following compounds were obtained according to a similar manner to that of Example 1.
(1) tert-Butyl [(2R)-2-hydroxy-2-phenylethyl][2-[4'-[[(methylsulfonyl)amino]carbonyl]-3'-(propylamino)-4-biphenylyl]ethyl]carbamate
(−)ESI-MS (m/z): 594 (M−H)⁻
(2) tert-Butyl [2-[3'-[(2-ethoxyethyl)amino]-4'-[[(methylsulfonyl)amino]carbonyl]-4-biphenylyl]ethyl]-[(2R)-2-hydroxy-2-phenylethyl]carbamate
(−)ESI-MS (m/z): 624 (M−H)⁻
(3) tert-Butyl [(1S,2R)-2-hydroxy-1-methyl-2-phenylethyl]-[2-[3'-(isopropylamino)-4'-[[(methylsulfonyl)amino]-carbonyl]-4-biphenylyl]ethyl]carbamate
(−)ESI-MS (m/z): 608 (M−H)⁻
(4) tert-Butyl [(2R)-2-hydroxy-2-phenylethyl][2-[[3'-(isopropylamino)-4'-[[(methylsulfonyl)amino]carbonyl]-4-biphenylyl]oxy]ethyl]carbamate
(−)ESI-MS (m/z): 610 (M−H)⁻
(5) tert-Butyl (2-[[3'-(cyclohexylamino)-4'-[[(methylsulfonyl)amino]carbonyl]-4-biphenylyl]-oxy]ethyl][(2R)-2-hydroxy-2-phenylethyl]carbamate
(−)ESI-MS (m/z): 650 (M−H)⁻
(6) tert-Butyl [(2R)-2-hydroxy-2-phenylethyl][2-[[4'-[[(methylsulfonyl)amino]carbonyl]-3'-(propylamino)-4-biphenylyl]oxy]ethyl]carbamate
(−)ESI-MS (m/z): 610 (M−H)⁻
(7) tert-Butyl (2-[[3'-[(2-ethoxyethyl)amino]-4'-[[(methylsulfonyl)amino]carbonyl]-4-biphenylyl]oxy]-ethyl][(2R)-2-hydroxy-2-phenylethyl]carbamate
(−)ESI-MS (m/z): 640 (M−H)⁻
(8) tert-Butyl [(1S)-2-hydroxy-1-[[3'-(isopropylthio)-4'-[[(methylsulfonyl)amino]carbonyl]-4-biphenylyl]methyl]-ethyl][(2R)-2-hydroxy-2-phenylethyl]carbamate
(−)ESI-MS (m/z): 641 (M−H)⁻
(9) tert-Butyl [(2R)-2-hydroxy-2-(4-nitrophenyl)ethyl][2-[3'-(isopropylthio)-4'-[[(methylsulfonyl)amino]-carbonyl]-4-biphenylyl]ethyl]carbamate
(−)ESI-MS (m/z): 656 (M−H)⁻
(10) Methyl 4'-[2-[(tert-butoxycarbonyl)[(2R)-2-hydroxy-2-(3-pyridyl)ethyl]amino]ethyl]-3-(isopropylthio)-4-biphenylcarboxylate
(+)ESI-MS (m/z): 551 (M+H)⁺

EXAMPLE 96

The following compound was obtained according to a similar manner to that of Example 11.

4'-[2-[(tert-Butoxycarbonyl)[(2R)-2-hydroxy-2-(3-pyridyl)ethyl]amino]ethyl]-3-(isopropylthio)-4-biphenylcarboxylic acid (−)ESI-MS (m/z): 535 (M−H)⁻

EXAMPLE 97

The following compound was obtained according to a similar manner to that of Example 59.

tert-Butyl [(2R)-2-(6-chloro-3-pyridyl)-2-hydroxyethyl][2-[3'-(isopropylamino)-4'-[[(methylsulfonyl)amino]carbonyl]-4-biphenylyl]ethyl]carbamate (−)ESI-MS (m/z): 629 (M−H)⁻

EXAMPLE 98

To a solution of tert-butyl [(2R)-2-(6-chloro-3-pyridyl)-2-hydroxyethyl][2-[3'-(isopropylamino)-4'-[[(methylsulfonyl)amino]carbonyl]-4-biphenylyl]ethyl]-carbamate (132 mg) in methanol (3.0 ml) and water (0.30 ml) were added ammonium formate (66 mg) and palladium on carbon (66 mg) at room temperature. The mixture was stirred under reflux for 1 hour. The suspension was cooled to room temperature, diluted with chloroform and filtrated. The filtrate was concentrated in vacuo and the residue was dissolved with chloroform, methanol and water. The organic layer was separated, and the aqueous layer was extracted with chloroform and methanol twice. The combined organic layer was washed with brine, dried over magnesium sulfate and concentrated in vacuo to give tert-butyl [(2R)-2-hydroxy-2-(3-pyridyl)ethyl][2-[3'-(isopropylamino)-4'-[[(methylsulfonyl)amino]carbonyl]-4-biphenylyl]ethyl]-carbamate (123 mg).
(−)ESI-MS (m/z): 595 (M−H)⁻

EXAMPLE 99

To a solution of 4-[(1R,2S)-2-amino-1-hydroxypropyl]-phenol (96.6 mg) in N,N-dimethylformamide (1.00 ml) were added diisopropylamine (156 µl) and 4'-(2-bromoethoxy)-3-(isopropylthio)-N-(methylsulfonyl)-4-biphenylcarboxamide (210 mg) at room temperature and stirred at 100° C. for 5 hours. To the reaction mixture was added hydrogen chloride 1,4-dioxane solution (4M, 464 µl) and stirred at 0° C. The mixture was filtrated and the filtrate was concentrated in vacuo. The residue was washed with ethyl ether three times, dried and purified with reverse phase silica gel column chromatography. To the resulting solution was added hydrogen chloride ethyl acetate solution (4M, 111 μl) and concentrated in vacuo to give 4'-[2-[[(1S,2R)-2-hydroxy-2-(4-hydroxyphenyl)-1-methylethyl]amino]ethoxy]-3-(isopropylthio)-N-(methylsulfonyl)-4-biphenylcarboxamide hydrochloride (108 mg).

NMR (DMSO-$d_6$, δ): 1.01 (3H, d, J=6.5 Hz), 1.26 (6H, d, J=6.5 Hz), 3.38 (3H, s), 3.25-3.58 (3H, m), 3.58-3.75 (1H, m), 4.32-4.49 (2H, m), 5.13 (1H, s), 5.98 (1H, br s), 6.78 (2H, d, J=8.5 Hz), 7.13 (2H, d, J=8.5 Hz), 7.19 (2H, d, J=8.5 Hz), 7.59 (2H, s), 7.72-7.77 (3H, m), 8.95 (1H, br s), 9.44 (1H, s), 12.18 (1H, br s) (−)ESI-MS (m/z): 557 (M−H)−

EXAMPLE 100

To a solution of 4-[(1R,2S)-2-amino-1-hydroxypropyl]phenol (75.4 mg) in N,N-dimethylformamide (1 ml) were added diisopropylamine (72.9 μl) and methyl 4'-(2-bromoethoxy)-3-(isopropylthio)-4-biphenylcarboxylate (142 mg) in N,N-dimethylformamide (0.4 ml) at room temperature and stirred at 100° C. for 4 hours. The reaction mixture was diluted with ethyl acetate and washed with saturated sodium bicarbonate aqueous solution, water and brine, dried over magnesium sulfate and concentrated in vacuo. The residue was purified with silica gel column chromatography to give methyl 4'-[2-[[(1S,2R)-2-hydroxy-2-(4-hydroxyphenyl)-1-methylethyl]-amino]ethoxy]-3-(isopropylthio)-4-biphenylcarboxylate (113 mg).

(+)ESI-MS (m/z): 496 (M+H)+

EXAMPLE 101

To a solution of methyl 4'-[2-[[(1S,2R)-2-hydroxy-2-(4-hydroxyphenyl)-1-methylethyl]amino]ethoxy]-3-(isopropylthio)-4-biphenylcarboxylate (110 mg) in methanol (1.65 ml) was added sodium hydroxide aqueous solution (1N 1.11 ml) and stirred at room temperature overnight. To the mixture was added hydrochloric acid aqueous solution (1N, 1.22 ml) and concentrated in vacuo. The residue was solved with methanol, added hydrogen chloride 1,4-dioxane solution (4M), concentrated in vacuo and dried to give 4'-[2-[[(1S,2R)-2-hydroxy-2-(4-hydroxyphenyl)-1-methylethyl]-amino] ethoxy]-3-(isopropylthio)-4-biphenylcarboxylic acid hydrochloride (97 mg).

NMR (DMSO-$d_6$, δ): 1.04 (3H, d, J=6.0 Hz), 1.32 (6H, d, J=6.5 Hz), 3.37-3.52 (3H, m), 3.69-3.83 (1H, m), 4.35-4.46 (2H, m), 5.12 (1H, br s), 5.98 (1H, br s), 6.77 (2H, d, J=8.5 Hz), 7.14 (2H, d, J=9.0 Hz), 7.19 (2H, d, J=8.5 Hz), 7.47 (1H, dd, J=1.5, 8.0 Hz), 7.58 (1H, s), 7.74 (2H, d, J=9.0 Hz), 7.89 (1H, d, J=8.0 Hz), 8.93 (1H, br s), 9.43 (1H, s) (−)ESI-MS (m/z): 480 (M−H)−

EXAMPLE 102

The following compounds were obtained according to a similar manner to that of Example 42.

(1) 3-Ethoxy-4'-[2-[[(2R)-2-hydroxy-2-(3-hydroxyphenyl)-ethyl]amino]ethoxy]-4-biphenylcarboxylic acid hydrochloride NMR (DMSO-$d_6$, δ): 1.36 (3H, t, J=7.0 Hz), 3.0-3.9 (4H, m), 4.10 (2H, t, J=7.0 Hz), 4.2-4.4 (2H, m), 4.8-5.0 (1H, m), 6.14 (1H, m), 6.7-6.9 (3H, m), 7.0-7.4 (5H, m), 7.7-7.9 (3H, m) MS (m/z): 438 (M+H)

(2) 4'-[2-[[(2R)-2-Hydroxy-2-(3-hydroxyphenyl)ethyl]-amino]ethoxy]-3-propoxy-4-biphenylcarboxylic acid hydrochloride NMR (DMSO-$d_6$, δ): 1.2 (3H, t, J=7.0 Hz), 1.6-1.9 (2H, m), 3.0-3.9 (4H, m), 4.11 (2H, t, J=7.0 Hz), 4.2-4.4 (2H, m), 4.8-5.0 (1H, m), 6.14 (1H, m), 6.7-6.9 (3H, m), 7.0-7.4 (5H, m), 7.7-7.9 (3H, m) MS (m/z): 452 (M+H)

(3) 4'-[2-[[(2R)-2-Hydroxy-2-(3-hydroxyphenyl)ethyl]-amino]ethoxy]-3-isopropoxy-4-biphenylcarboxylic acid NMR (DMSO-$d_6$, δ): 1.31 (6H, m), 3.0-3.9 (4H, m), 4.2-4.4 (2H, m), 4.8-5.0 (2H, m), 6.15 (1H, m), 6.7-6.9 (3H, m), 7.0-7.4 (5H, m), 7.7-7.9 (3H, m) MS (m/z): 452 (M+H)

(4) 3-(2-Ethoxyethoxy)-4'-[2-[[(2R)-2-hydroxy-2-(3-hydroxyphenyl)ethyl]amino]ethoxy]-4-biphenylcarboxylic acid hydrochloride NMR (DMSO-$d_6$, δ): 1.11 (3H, t, J=7.0 Hz), 3.2-3.8 (4H, m), 4.2-4.4 (4H, m), 4.8-5.0 (1H, m), 6.15 (1H, m), 6.7-6.9 (3H, m), 7.0-7.4 (5H, m), 7.7-7.9 (3H, m) MS (m/z) 482 (M+H)

(5) 4'-[2-[[(2R)-2-Hydroxy-2-(3-hydroxyphenyl)ethyl] amino]-ethoxy]-3-isopropoxy-N-(methylsulfonyl)-4-biphenylcarboxamide hydrochloride NMR (DMSO-$d_6$, δ): 1.32 (6H, d, J=6.0 Hz), 3.0-3.8 (4H, m), 3.43 (3H, s), 4.3 (2H, m), 4.8-5.0 (2H, m), 6.15 (1H, m), 6.7-7.7 (8H, m), 7.7-7.9 (3H, m) MS (m/z): 529 (M+H)

(6) 4'-[2-[[(2R)-2-Hydroxy-2-(3-hydroxyphenyl)ethyl] amino]-ethyl]-3-isopropoxy-N-(methylsulfonyl)-4-biphenylcarboxamide hydrochloride NMR (DMSO-$d_6$, δ): 1.29 (6H, d, J=5.9 Hz), 2.8-3.5 (6H, m), 3.34 (3H, s), 4.9 (2H, m), 6.21 (1H, m), 6.6-6.9 (3H, m), 7.0-7.3 (6H, m), 7.7-7.9 (2H, m) MS (m/z): 512 (M+H)

EXAMPLE 103

The following compound was obtained according to a similar manner to that of Example 4.

4'-[2-[[(2R)-2-Hydroxy-2-(3-hydroxyphenyl)ethyl] amino]-ethyl]-3-isopropoxy-4-biphenylcarboxylic acid hydrochloride NMR (DMSO-$d_6$, δ): 1.26 (6H, d, J=5.9 Hz), 2.8-3.5 (6H, m), 4.76 (1H, m), 4.94 (1H, m), 6.15 (1H, m), 6.6-7.8 (11H, m) MS (m/z): 436 (M+H)

EXAMPLE 104

The following compound was obtained according to a similar manner to that of Example 1 followed by a similar manner to that of Example 59.

4'-[2-[[(2R)-2-hydroxy-2-(3-pyridyl)ethyl]amino]-ethyl]-3-(isopropylamino)-N-(methylsulfonyl)-4-biphenylcarboxamide trihydrochloride NMR (DMSO-$d_6$, δ): 1.24 (6H, d, J=3.1 Hz), 3.07-3.11 (2H, m), 3.18-3.31 (3H, m), 3.37 (3H, s), 3.37-3.43 (1H, m), 3.9-3.93 (1H, m), 5.35 (1H, dd, J=1.5, 4.4 Hz), 6.86 (1H, d, J=4.2 Hz), 6.97 (1H, s), 7.38 (2H, d, J=4.1 Hz), 7.7 (2H, d, J=4.1 Hz), 7.83 (1H, d, J=4.2 Hz), 8.08 (1H, dd, J=2.8, 4 Hz), 8.6 (1H, d, J=4 Hz), 8.89 (1H, d, J=2.8 Hz), 8.95 (1H, s), 9.34 (1H, br s), 9.44 (1H, br s) (−)ESI-MS (m/z): 495 (M−H)−

EXAMPLE 105

The following compound was obtained according to a similar manner to that of Preparation 11 followed by similar manner to those of Example 8 and then Example 9.

Methyl 2-amino-4'-[2-[(tert-butoxycarbonyl)[(2R)-2-hydroxy-2-phenylethyl]amino]ethyl]-4-biphenylcarboxylate NMR (DMSO-d$_6$, δ): 1.34 (9H, s), 2.7-2.9 (2H, m), 3.2-3.4 (4H, m), 3.8 (3H, s), 4.7 (1H, br), 5.05 (2H, br), 5.45 (1H, br), 7.04-7.41 (12H, m) MS (m/z): 491 (M+H)$^+$

EXAMPLE 106

The following compound was obtained according to a similar manner to that of Example 4.

4'-[2-[[(2R)-2-Hydroxy-2-(3-methoxyphenyl)ethyl]amino]-ethyl]-3-isopropoxy-4-biphenylcarboxylic acid hydrochloride NMR (DMSO-d$_6$, δ): 1.29 (6H, d, J=5.9 Hz), 2.8-3.5 (6H, m), 3.33 (3H, s), 4.81 (1H, m), 4.94 (1H, m), 6.21 (1H, m), 6.6-7.8 (11H, m) MS (m/z): 450 (M+H)

EXAMPLE 107

The following compound was obtained according to a similar manner to that of Example 12 followed by a similar manner to that of Example 14.

4'-[2-[[(2R)-2-[3-[(Methanesulfonyl)amino]phenyl]-2-hydroxyethyl]amino]ethyl]-3-isopropoxy-4-biphenylcarboxylic acid dihydrochloride NMR (DMSO-d$_6$, δ): 1.25 (6H, d, J=5.9 Hz), 2.8-3.5 (6H, m), 4.89 (1H, m), 4.94 (1H, m), 6.15 (1H, m), 7.0-7.8 (11H, m) MS (m/z): 513 (M+H)

EXAMPLE 108

The following compound was obtained according to a similar manner to that of Example 13 followed by a similar manner to that of Example 14.

4'-[2-[[(2R)-2-[3-[(Methanesulfonyl)amino]phenyl]-2-hydroxyethyl]amino]ethyl]-3-isopropoxy-N-(methylsulfonyl)-4biphenylcarboxamide dihydrochloride NMR (DMSO-d$_6$, δ): 1.25 (6H, d, J=5.9 Hz), 2.8-3.5 (6H, m), 4.89 (1H, m), 4.94 (1H, m), 6.15 (1H, m), 7.0-7.8 (11H, m) MS (m/z): 590 (M+H)

The invention claimed is:

1. A compound of the formula [I]:

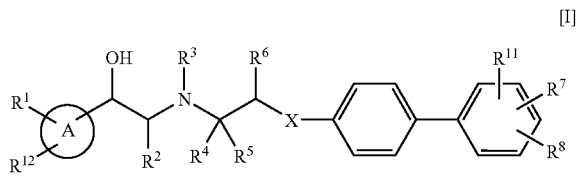

wherein

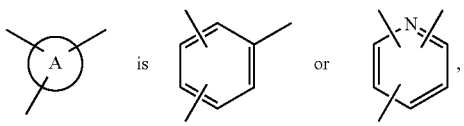

X is a bond, —CH$_2$—, —O—, or —NH—,

R$^1$ and R$^{12}$ are each independently hydrogen, halogen, lower alkyl, hydroxy, lower alkoxy, benzyloxy, nitro, amino, or (lower alkylsulfonyl)amino, R$^2$ is hydrogen or optionally substituted lower alkyl, R$^3$ is hydrogen or an amino protective group, R$^4$, R$^5$, and R$^6$ are each independently hydrogen or optionally substituted lower alkyl, R$^7$ is -Z-R$^{13}$, in which Z is a bond or —(CH$_2$)$_n$— (in which n is 1), and R$^{13}$ is (lower alkylsulfonyl)carbamoyl or lower alkanoylsulfamoyl, R$^8$ is —Y—R$^9$, in which Y is a bond, —CH$_2$—, —O—, —S—, —SO—, —SO$_2$—, —NH—, or

in which R$^{10}$ is lower alkyl, cyclo(lower)alkyl, or aryl), and

R$^9$ is hydrogen, lower alkyl, cyclo(lower)alkyl, mono(or di or tri)halo(lower)alkyl, lower alkanoyl, lower alkenyl, lower alkoxy(lower)alkyl, nitro, aryl, or a heterocyclic group, and R$^{11}$ is hydrogen, lower alkyl, lower alkoxy, amino or mono (or di)lower(alkyl)amino, or a salt thereof.

2. A compound of claim 1, which is 4'-[2-[[(2R)-2-hydroxy-2-phenylethyl]amino]ethyl]-3-(3-methylbutyl)-N-(methylsulfonyl)-4-biphenylcarboxamide or a pharmaceutically acceptable salt thereof.

3. A compound of claim 1, which is 4'-[2-[[(2R)-2-hydroxy-2-phenylethyl]amino]ethyl]-3-isobutyl-N-(methylsulfonyl)-4-biphenylcarboxamide or a pharmaceutically acceptable salt thereof.

4. A compound of claim 1, which is 4'-[2-[[(1S,2R)-2-hydroxy-1-methyl-2-phenylethyl]amino]ethyl]-3-isobutyl-N-(methylsulfonyl)-4-biphenylcarboxamide or a pharmaceutically acceptable salt thereof.

5. A compound of claim 1, which is 4'-[2-[[(2R)-2-hydroxy-2-phenylethyl]amino]ethyl]-3-(isopropylthio)-N-(methylsulfonyl)-4-biphenylcarboxamide or a pharmaceutically acceptable salt thereof.

6. A compound of claim 1, which is 3-(cyclohexyloxy)-4'-[2-[[(2R)-2-hydroxy-2-phenylethyl]amino]ethyl]-N-(methylsulfonyl)-4-biphenylcarboxamide or a pharmaceutically acceptable salt thereof.

7. A compound of claim 1, which is 3-(cyclohexyloxy)-4'-[2-[[(2R)-2-hydroxy-2-(3-pyridyl)ethyl]amino]ethyl]-N-(methylsulfonyl)-4-biphenylcarboxamide or a pharmaceutically acceptable salt thereof.

8. A compound of claim 1, which is 2-[3-(cyclohexyloxy)-4'-[2-[[(2R)-2-hydroxy-2-phenylethyl]amino]ethyl]-4-biphenylyl]-N-(methylsulfonyl)acetamide or a pharmaceutically acceptable salt thereof.

9. A compound of claim 1, which is N-[[3-(cyclohexyloxy)-4'-[2-[[(2R)-2-hydroxy-2-phenylethyl]amino]ethyl]-4-biphenylyl]sulfonyl]acetamide or a pharmaceutically acceptable salt thereof.

10. A compound of claim 1, which is N-[[3-(cyclohexyloxy)-4'-[2-[[(2R)-2-hydroxy-2-phenylethyl]amino]ethyl]-4-biphenylyl]sulfonyl]butanamide or a pharmaceutically acceptable salt thereof.

11. A compound of claim 1, which is 3-(cyclohexylamino)-4'-[2-[[(2R)-2-hydroxy-2-phenylethyl]amino]ethyl]-N-(methylsulfonyl)-4-biphenylcarboxamide or a pharmaceutically acceptable salt thereof.

12. A compound of claim 1, which is 4'-[2-[[(2R)-2-hydroxy-2-phenylethyl]amino]ethyl]-3-(isopropylamino)-N-(methylsulfonyl)-4-biphenylcarboxamide or a pharmaceutically acceptable salt thereof.

13. A compound of claim 1, wherein

X is bond, $R^1$ and $R^{12}$ are each independently hydrogen or halogen, $R^3$ is hydrogen, $R^4$ is hydrogen, $R^8$ is —Y—$R^9$, in which Y is a bond, —$CH_2$—, —O—, —S— or NH—, and $R^9$ is lower alkyl or cyclo(lower)alkyl, and $R^{11}$ is hydrogen.

14. A compound of claim 13, which is selected from the group consisting of

4'-[2-[[(2R)-2-Hydroxy-2-phenylethyl]amino]ethyl]-3-(3-methylbutyl)-N-(methylsulfonyl)-4-biphenylcarboxamide, 4'-[2-[[(2R)-2-Hydroxy-2-phenylethyl]amino]ethyl]-3-isobutyl-N-(methylsulfonyl)-4-biphenylcarboxamide, 4'-[2-[[(1S,2R)-2-Hydroxy-1-methyl-2-phenylethyl]amino]ethyl]-3-isobutyl-N-(methylsulfonyl)-4-biphenylcarboxamide, 4'-[2-[[(2R)-2-Hydroxy-2-phenylethyl]amino]ethyl]-3-(isopropylthio)-N-(methylsulfonyl)-4-biphenylcarboxamide, 3-(Cyclohexyloxy)-4'-[2-[[(2R)-2-hydroxy-2-phenylethyl]amino]ethyl]-N-(methylsulfonyl)-4-biphenylcarboxamide, 3-(Cyclohexyloxy)-4'-[2-[[(2R)-2-hydroxy-2-(3-pyridyl)ethyl]amino]ethyl]-N-(methylsulfonyl)-4-biphenylcarboxamide, 2-[3-(Cyclohexyloxy)-4'-[2-[[(2R)-2-hydroxy-2-phenylethyl]amino]ethyl]-4-biphenylyl]-N-(methylsulfonyl)acetamide, 2-[3-(Cyclohexyloxy)-4'-[2-[[(2R)-2-hydroxy-2-(3-pyridyl)ethyl]amino]-ethyl]-4-biphenylyl]-N-(methylsulfonyl)acetamide, N-[[3-(Cyclohexyloxy)-4'-[2-[[(2R)-2-hydroxy-2-phenylethyl]amino]ethyl]-4-biphenylyl]sulfonyl]acetamide, N-[[3-(Cyclohexyloxy)-4'-[2-[[(2R)-2-hydroxy-2-phenylethyl]amino]ethyl]-4-biphenylyl]sulfonyl]butanamide, 3-(Cyclohexylamino)-4'-[2-[[(2R)-2-hydroxy-2-phenylethyl]amino]ethyl]-N-(methylsulfonyl)-4-biphenylcarboxamide, and 4'-[2-[[(2R)-2-Hydroxy-2-phenylethyl]amino]ethyl]-3-(isopropylamino)-N-(methylsulfonyl)-4-biphenylcarboxamide, or a pharmaceutically acceptable salt thereof.

15. A compound of claim 13, which is 2-[3-(cyclohexyloxy)-4'-[2-[[(2R)-2-hydroxy-2-(3-pyridyl)ethyl]amino]ethyl]-4-biphenylyl]-N-methylsulfonyl)-acetamide or a pharmaceutically acceptable salt thereof.

16. A pharmaceutical composition which comprises, as an active ingredient, a compound of claim 1 or a pharmaceutically acceptable salt thereof in admixture with at least one pharmaceutically acceptable carrier or excipient.

* * * * *